US012708675B2

(12) United States Patent
Weng et al.

(10) Patent No.: US 12,708,675 B2
(45) **Date of Patent: *Aug. 18, 2026**

(54) NITROGEN-BRANCHED NON-LINEAR PEGYLATED LIPID CONTAINING A TERTIARY AMINE AND APPLICATION THEREOF

(71) Applicant: XIAMEN SINOPEG BIOTECH CO., LTD., Xiamen (CN)

(72) Inventors: Wengui Weng, Xiamen (CN); Chao Liu, Xiamen (CN); Dandan Chen, Xiamen (CN); Sheng Lin, Xiamen (CN); Ailan Wang, Xiamen (CN); Guohua Wei, Xiamen (CN); Congming Lin, Xiamen (CN); Qi Zhu, Xiamen (CN)

(73) Assignee: XIAMEN SINOPEG BIOTECH CO., LTD., Xiamen (CN)

( * ) Notice: Subject to any disclaimer, the term of this patent is extended or adjusted under 35 U.S.C. 154(b) by 159 days.

This patent is subject to a terminal disclaimer.

(21) Appl. No.: 18/839,174

(22) PCT Filed: Apr. 11, 2023

(86) PCT No.: PCT/CN2023/087702

§ 371 (c)(1),
(2) Date: Aug. 16, 2024

(87) PCT Pub. No.: WO2023/198085

PCT Pub. Date: Oct. 19, 2023

(65) Prior Publication Data

US 2025/0152512 A1 May 15, 2025

(30) Foreign Application Priority Data

Apr. 12, 2022 (CN) ........................ 202210380598.6

(51) Int. Cl.
*A61K 48/00* (2006.01)
*A61K 9/1271* (2025.01)
(Continued)

(52) U.S. Cl.
CPC ........ *A61K 48/0041* (2013.01); *A61K 9/1271* (2013.01); *A61K 9/1272* (2013.01);
(Continued)

(58) Field of Classification Search
CPC .... A61K 48/00; A61K 9/1271; A61K 9/1272; A61K 9/51; A61K 31/7105;
(Continued)

(56) References Cited

U.S. PATENT DOCUMENTS

2005/0180946 A1 8/2005 Ji et al.
2014/0200257 A1 7/2014 Rajeev et al.

FOREIGN PATENT DOCUMENTS

AU 2014200910 A1 3/2014
CN 1243779 C 3/2006
(Continued)

OTHER PUBLICATIONS

Jun. 8, 2023 International Search Report issued in International Patent Application No. PCT/CN2023/087702.
(Continued)

*Primary Examiner* — Trevor Love
(74) *Attorney, Agent, or Firm* — Oliff PLC

(57) ABSTRACT

A nitrogen-branched non-linear PEGylated lipid containing a tertiary amine, which is represented by the Formula (1); wherein, $B_1$ and $B_2$ are linking bonds or alkylene groups; $L_1$, $L_2$, $L_d$ and $L_x$ are linking bonds or divalent linking groups L; $R_1$ and $R_2$ are $C_{1-50}$ aliphatic hydrocarbon groups or $C_{1-50}$ residues of aliphatic hydrocarbon derivative, each containing 0-10 heteroatoms; $N_{core}$ is a multivalent group of valence
(Continued)

y+1 and contains a trivalent nitrogen-atom branching core connected to $L_d$; y is 2, 3, 4, 5, 6, 7, 8, 9, or ≥10; XPEG are polyethylene glycol components. Compared with linear PEGylated lipids, the nitrogen-branched PEGylated lipid herein can realize better surface modification of LNP. The present invention also provides a lipid pharmaceutical composition and its formulation containing the PEGylated lipid, which can enhance the targeting ability of drugs and improve the transfection efficiency of nucleic acid drugs.

(1)

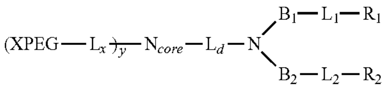

11 Claims, 1 Drawing Sheet

(51) Int. Cl.

| | |
|---|---|
| ***A61K 9/1272*** | (2025.01) |
| ***A61K 9/51*** | (2006.01) |
| ***A61K 31/7105*** | (2006.01) |
| ***A61K 31/711*** | (2006.01) |
| ***A61K 39/385*** | (2006.01) |
| ***A61K 45/06*** | (2006.01) |
| ***A61K 47/10*** | (2017.01) |
| ***A61K 47/18*** | (2017.01) |
| ***A61K 47/22*** | (2006.01) |
| ***A61K 47/24*** | (2006.01) |
| ***A61K 47/34*** | (2017.01) |
| ***C07C 217/18*** | (2006.01) |
| ***C07C 219/04*** | (2006.01) |
| ***C07C 235/08*** | (2006.01) |
| ***C07C 235/10*** | (2006.01) |
| ***C07C 235/12*** | (2006.01) |
| ***C07C 271/20*** | (2006.01) |
| ***C07D 209/88*** | (2006.01) |
| ***C07D 255/02*** | (2006.01) |
| ***C07D 487/04*** | (2006.01) |
| ***C08G 65/48*** | (2006.01) |

(52) U.S. Cl.

CPC ........ *A61K 9/5123* (2013.01); *A61K 31/7105* (2013.01); *A61K 31/711* (2013.01); *A61K 39/385* (2013.01); *A61K 45/06* (2013.01); *A61K 47/10* (2013.01); *A61K 47/183* (2013.01); *A61K 47/22* (2013.01); *A61K 47/24* (2013.01); *A61K 47/34* (2013.01); *C07C 217/18* (2013.01); *C07C 219/04* (2013.01); *C07C 235/08* (2013.01); *C07C 235/10* (2013.01); *C07C 235/12* (2013.01); *C07C 271/20* (2013.01); *C07D 209/88* (2013.01); *C07D 255/02* (2013.01); *C07D 487/04* (2013.01); *C08G 65/48* (2013.01); *C07C 2601/16* (2017.05)

(58) Field of Classification Search

CPC .... A61K 31/711; A61K 39/385; A61K 45/06; A61K 47/10; A61K 47/22; A61K 47/24; A61K 47/34; C07C 217/18; C07C 219/04; C07C 235/08; C07C 235/10; C07C 235/12; C07C 271/20; C07D 209/88; C07D 255/02; C07D 487/04; C08G 65/48

See application file for complete search history.

(56) References Cited

FOREIGN PATENT DOCUMENTS

| | | | |
|---|---|---|---|
| CN | 101029131 | A | 9/2007 |
| CN | 104109235 | A | 10/2014 |
| CN | 104530415 | A | 4/2015 |
| CN | 104530417 | A | 4/2015 |
| CN | 104725628 | A | 6/2015 |
| CN | 104877127 | A | 9/2015 |
| CN | 106967213 | A | 7/2017 |
| CN | 108530617 | A | 9/2018 |
| CN | 108530637 | A | 9/2018 |
| CN | 108659227 | A | 10/2018 |
| CN | 110591079 | A | 12/2019 |
| CN | 108530617 | B | 11/2020 |
| CN | 108530637 | B | 3/2021 |
| CN | 112694608 | A | 4/2021 |
| CN | 113402405 | A | 9/2021 |
| CN | 113429559 | A | 9/2021 |
| WO | 2016/206540 | A1 | 12/2016 |

OTHER PUBLICATIONS

Veronese et al., "The Impact of PEGylation on Biological Therapies", BioDrugs, 2008, vol. 22, pp. 315-329.

Mastrotto et al., "In Vitro and in Vivo Behavior of Liposomes Decorated with PEGs with Different Chemical Features", Mol. Pharmaceutics, 2020, vol. 17, pp. 472-487.

Hassett et al., "Impact of lipid nanoparticle size on mRNA vaccine immunogenicity", Journal of Controlled Release, 2021, vol. 335, pp. 237-246.

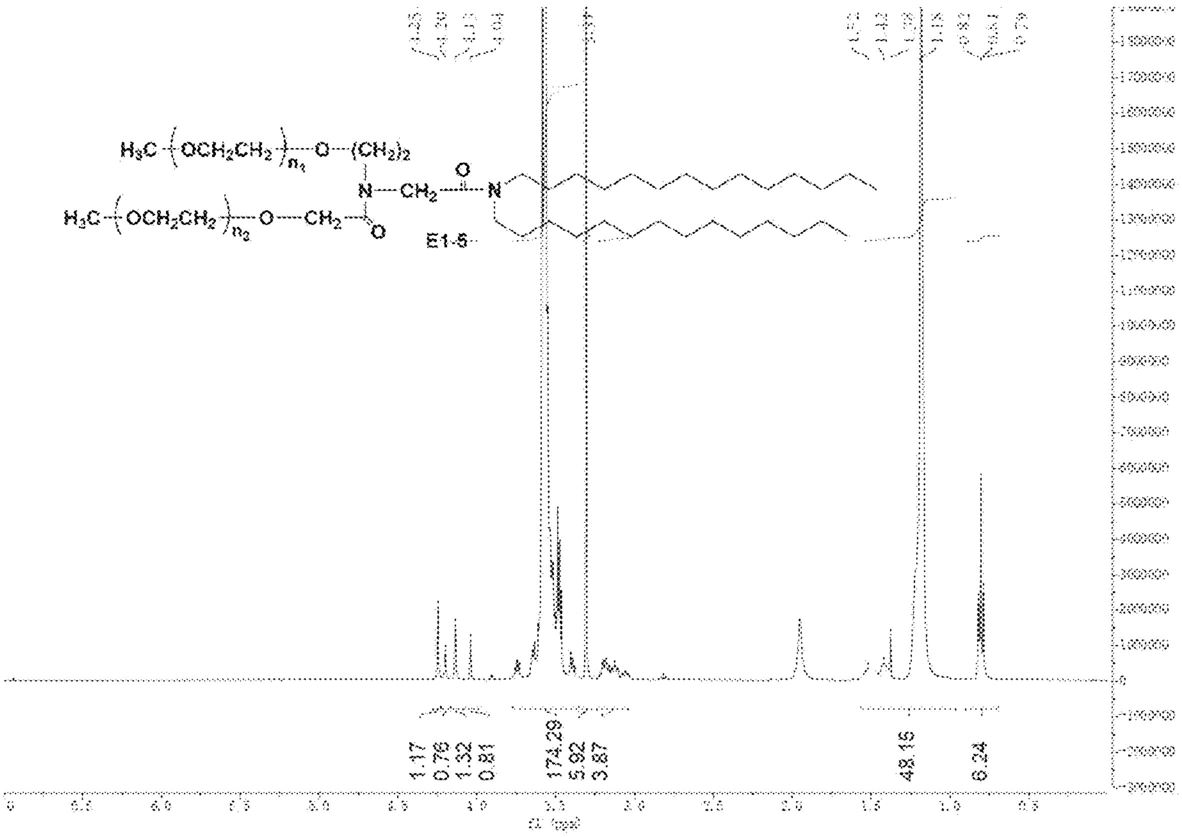
E1-5

NITROGEN-BRANCHED NON-LINEAR PEGYLATED LIPID CONTAINING A TERTIARY AMINE AND APPLICATION THEREOF

CROSS-REFERENCE TO RELATED APPLICATIONS

This application is a U.S. National Phase Application of International Application No. PCT/CN2023/087702, filed Apr. 11, 2023 which claims priority to Chinese Application No. CN202210380598.6, filed Apr. 12, 2022. All of the aforementioned patent applications are hereby incorporated by reference in their entireties.

TECHNICAL FIELD

The present invention belongs to the field of drug delivery, and overall relates to a PEGylated lipid; specifically, it relates to a tertiary amine-containing nitrogen-branched non-linear PEGylated lipid that can be used as a component for drug carriers. The present invention also relates to a lipid composition and a lipid pharmaceutical composition, both containing the lipid, and formulation and application thereof.

BACKGROUND OF THE INVENTION

Liposomes are widely used for delivering nucleic acid drugs, genetic vaccines, anti-neoplastic drugs, small molecule drugs, peptide drugs, or protein drugs; wherein, the lipid nanoparticle (LNP) has become a popular delivery technology due to the development of vaccines against coronavirus. An LNP can contain not only negatively charged mRNA, but also four types of components including cationic lipids, neutral lipids, steroid lipids, and PEGylated lipids; wherein, cationic lipids electrostatically interact with the negatively charged mRNA; neutral lipids are usually phospholipids that prevent lipids from oxidation, or attach ligands to the surface of liposome or LNP, or reduce the aggregation of lipid particles; steroid lipids have stronger membrane fusogenic properties that facilitate cellular uptake and cytosolic entry of mRNA; PEGylated lipids are located at the surface of lipid nanoparticles to improve hydrophilicity, avoid rapid clearance by the immune system, prevent particle aggregation, and increase stability.

Cationic lipids and PEGylated lipids are particularly crucial components of LNP. Cationic lipids include permanent cationic lipids and ionizable cationic lipids, wherein the permanent cationic lipids can easily cause interference and even damage to biofilms in the systemic circulation while the ionizable cationic lipids can be non-ionized or slightly ionized under physiological conditions to reduce toxicity. After the cellular uptake, the ionizable cationic lipids can be ionized under acidic conditions inside the endosomal lumen to carry a partial positive charge, increasing membrane permeability. Meanwhile, the LNPs are degraded or reorganized, promoting the escape of mRNA from endosomes. The mRNA released into the cytoplasm can be further translated, and thus completes the delivery and transfection of mRNA molecules.

Cationic liposomes or LNPs without surface modifications generally lack sufficient stability in the systematic circulation. Adding PEGylated lipids in a liposome or LNP formulation can achieve the effect of covalently binding polyethylene glycols to the surface of liposome or LNP and, therefore, reduce the nonspecific cellular uptake in the process of drug delivery, realize the stealth effect of liposome or LNP, and improve the efficacy of pharmaceutical formulations thereof.

At present, the PEGylated lipids that have been applied and studied in a wider scope are basically modified with linear polyethylene glycols, with typical examples including DMG-PEG2000 (PEG2k-DMG) and ALC-0159, whereas non-linear PEGylated lipids are rarely used. Polyethylene glycol modification can improve the stability and safety of the modified substances in vivo, but at the same time also reduce the cellular uptake efficiency of drugs. Conventional PEGylated lipids are modified with linear polyethylene glycols which, if replaced by non-linear polyethylene glycols of comparable molecular weight, will cause a reduction of the cellular uptake efficiency of the modified substances due to the higher protection ability of its umbrella-like shape (Veronese et al., *BioDrugs*. 2008, 22, 315-329). Moreover, many studies have revealed the phenomenon that PEGylated lipids can gradually detach from the surface of liposomes or LNPs and, therefore, cause the liposomes or LNPs to partially or completely lose the stealth properties, and such phenomenon becomes more pronounced under the presence of serum proteins and the shear forces in the bloodstream. With the single-chain length being comparable to that of a linear PEGylated lipid, the non-linear PEGylated lipid is easier to detach due to the greater shear forces attributed to the higher molecular weight of the polyethylene glycol moiety in a single lipid molecule (Mastrotto et al., *Mol. Pharmaceutics* 2020, 17, 472-487).

To solve the aforementioned problems, it is necessary to develop a novel type of non-linear PEGylated lipid.

SUMMARY OF THE INVENTION

The present invention provides a novel non-linear PEGylated lipid, in particular a tertiary amine-containing nitrogen-branched non-linear PEGylated lipid, which can be used in the preparation of lipid nanoparticles and pharmaceutical formulations thereof, leading to advantages such as excellent protection, stability in systematic circulation, better cellular uptake efficiency, high biocompatibility, low toxicity, high encapsulation efficiency, and high delivery efficiency.

The above-mentioned purpose of the present invention is achieved through the technical solution as follows.

(1)

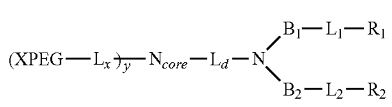

In One Embodiment of the Present Invention provided herein is a nitrogen-branched PEGylated lipid having the structure represented by the general formula (1):

(1)

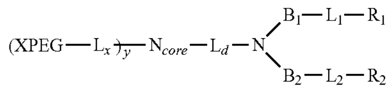

wherein, $B_1$ and $B_2$ are each independently a linking bond or an alkylene group;

$L_1$, $L_2$, $L_d$ and y instances $L_x$ are each independently a linking bond or the divalent linking group L;

$R_1$ and $R_2$ are each independently a $C_{1-50}$ aliphatic hydrocarbon group or a $C_{1-50}$ residue of aliphatic hydrocarbon derivative, containing 0-10 heteroatoms; the heteroatom is B, O, N, Si, P or S;

$N_{core}$ is a multivalent group having a valence of y+1; $N_{core}$ contains a trivalent nitrogen-atom branching core connected to $L_d$;

y is 2, 3, 4, 5, 6, 7, 8 or 9, or y≥10, preferably 2 or 3;

XPEG are polyethylene glycol components.

Another embodiment of the present invention is provided herein:

A lipid composition containing the PEGylated lipid having the structure represented by the general formula (1).

Another embodiment of the present invention is provided herein:

A lipid pharmaceutical composition containing the aforementioned lipid composition and drugs.

Another embodiment of the present invention is provided herein:

A formulation of lipid pharmaceutical composition containing the aforementioned lipid pharmaceutical composition and pharmaceutically acceptable diluents or excipients.

Compared with the Prior Art, the Present Invention Brings the Following Beneficial Effects:

The present invention provides tertiary amine-containing nitrogen-branched non-linear PEGylated lipid compounds (referred to as nitrogen-branched PEGylated lipid), as well as lipid compositions and lipid pharmaceutical compositions containing the nitrogen-branched PEGylated lipid and formulations and applications thereof. Compared with linear PEGylated lipids, the nitrogen-branched PEGylated lipids of the present invention can, with lower molar amounts and/or shorter PEG chains, achieve better effects of modification on the LNP surface, provide better protection, prolong the systematic circulation time, and reduce the biotoxicity of LNP by a greater degree. In particular, by coupling targeting groups at the ends of polyethylene glycols, the LNP of the present invention can be used as a carrier for targeted delivery of one or more bioactive agents. In particular, by introducing degradable groups at suitable locations in the structure of a nitrogen-branched PEGylated lipid, the cationic lipid nanoparticles carrying nucleic acid drugs can have better cellular uptake efficiency and/or transfection efficiency. The present invention also provides lipid pharmaceutical compositions containing the nitrogen-branched PEGylated lipid and formulations thereof, with better efficacy including improved drug targeting properties and elevated transfection efficiency of nucleic acid drugs.

BRIEF DESCRIPTION OF DRAWINGS

FIG. 1 shows the NMR spectrum ($^1H$ NMR) of the nitrogen-branched PEGylated lipid (E1-5) prepared in the Example 1.5 of the present invention.

1. DETAILED DESCRIPTION OF THE INVENTION

The present invention has provided a detailed description of the specific embodiments; however, it should be understood that, it is only provided in an illustrative manner rather than a restrictive manner. Any changes and modifications within the scope of the present invention will be obvious to those skilled in the art.

If a reference cited herein has a description different from the description in the present invention, the present invention shall prevail. This principle applies to all references cited throughout the specification.

1.1. Terminology

In the present invention, unless otherwise described, all technical and scientific terms used herein have the same meaning as is commonly understood by one of ordinary skill in the art. The disclosures of all patents and other publications cited herein are incorporated by reference in their entireties. In the event that any description or interpretation of a term herein conflicts with any document incorporated herein by reference, the following description or interpretation of the term shall prevail. Unless otherwise specified, each term has the following meaning.

In the present invention, unless otherwise specified, the terms "selected from"/"preferably selected from" for any two objects are independent from each other. When multiple levels are available for the selections or preferred selections, those selected or preferably selected for any two objects can be of the same or different levels. For example, the statement "$L_A$ and $L_B$ are each independently selected from A, B, and C" implies that both $L_A$ and $L_B$ can be A, or that $L_A$ is A while $L_B$ is $B_1$ ($B_1$ is a subclass of B). For example, the statement "$L_A$ is preferably A (level 1 preferred selection), more preferably selected from $A_1$~$A_3$ (level 2 preferred selection), and most preferably selected from $A_{11}$~$A_{13}$ (level 3 preferred selection); $L_B$ is preferably B (level 1 preferred selection), more preferably selected from $B_1$~$B_3$ (level 2 preferred selection), and most preferably selected from $B_{11}$~$B_{13}$ (level 3 preferred selection)" implies that the preferred selections can be, that A is selected from $A_1$~$A_3$ (level 2 preferred selection) while B is selected from $B_1$~$B_{13}$ (level 3 preferred selection), or that A and B are both selected from their own level 3 preferred selections.

In the present invention, the terms "each independently", "each independently selected from", and "preferably, each independently selected from" mean that different objects can be each independently, or each independently selected from, or preferably, each independently selected from any option within the definitions, which can also be applied to the same object at different locations or occurrences. For example, provided that "a divalent group is selected from the group consisting of $—NR_cC(=O)—$, $—C(=O)NR_c—$, $—NR_cC(=O)NR_c—$, $—OC(=O)NR_c—$, $—NR_cC(=O)O—$, $—SC(=O)NR_c—$, $—NR_cC(=O)S—$, $—C(R_c)=N—NR_c—$, and $—NR_c—N=C(R_c)—$; wherein, $R_c$ is, at each occurrence, independently H or a $C_{1-12}$ alkyl group", such description indicates that the two $R_c$ groups can be the same or different in "$—NR_c—N=C(R_c)—$" (e.g., one $R_c$ is a methyl group while the other $R_c$ is a hydrogen atom or an ethyl group), and that any $R_c$ in "$—NR_cC(=O)NR_c—$" can be the same as or different from the $R_c$ in "$—NR_cC(=O)O—$".

In the present invention, when at least two items are listed, the "combination" of the listed items is composed of any two or more of the aforementioned listed items; wherein, the number of an item is not limited, and the number of any item can be one or greater than one; when the number of an item is greater than 1, any two of the items can appear in the same or different specific forms. For example, provided that "a divalent linking group is selected from the group consisting of $—CH_2—$, $—O—$, $—S—$, $—C(=O)—$, $—NR_c—$, and combinations thereof; wherein, $R_c$ is, at each occurrence, independently a hydrogen atom or a $C_{1-5}$ alkyl group", the divalent linking group can be $—CH_2—$, —O—, —S—, —C(═O)— or $—NR_c—$, or a combination, e.g., $—CH_2—NH—CH_2—$ (wherein, the number of $—CH_2—$ is 2, and the number of $—NR_c—$ is 1), $—(CH_2)_2—NH—(CH_2)_4—N(CH_3)—$ (wherein, the number of $—CH_2—$ is 6, and the number of $—NR_c—$ is 2 with unidentical specific forms), or $—(CH_2)_2—NHC(═O)—$ (wherein, the number of $—CH_2—$ is 2, the number of $—NR_c—$ is 1, and the number of —C(═O)— is 1), etc. Particularly, a combination composed of a linking bond and any linking group is still the linking group itself. In the present invention, a "linking group" contains at least one atom by default.

In the present invention, unless otherwise specified, the terms "include", "contain", "cover" and similar expressions in the specification and claims herein shall be interpreted as "include(s) but is/are not limited to" or "include(s) without limitation" in an open and inclusive manner.

In the present invention, the term "include(s) but is/are not limited to" followed by a certain range means that the items within the range are selectable but the selections are not limited to the range. Not all structures within the range are applicable, and especially, the items explicitly excluded by the present invention are not for consideration. The basic principle is to use the successful implementation of the present invention as a screening criterion.

In the present invention, the interpretation of numerical intervals includes a numerical interval indicated by a dash (e.g., 1-6), a numerical interval indicated by a wavy line (e.g., 1-6), and a numerical interval indicated by "to" (e.g., 1 to 6). Unless otherwise specified, an interval in the form of a range can represent a group consisting of all integers and non-integers within the range including two endpoints. For example, provided that an average number of EO units is selected from 22~100, the range of selections is not limited to integers but also any non-integers within the interval. For example, the "integer in the range of 1-3" represents a group consisting of 1, 2, and 3. For example, $—(CH_2)_{1-4}—$ represents a group consisting of $—CH_2—$, $—(CH_2)_2—$, $—(CH_2)_3—$, and $—(CH_2)_4—$. For example,

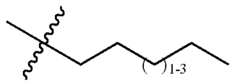

represents a group consisting of

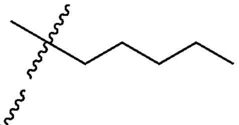,

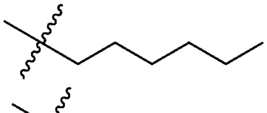, and

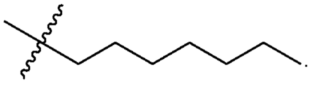.

The numerical intervals in the present invention, including but not limited to the numerical intervals represented by integers, non-integers, percentages and fractions, all include two endpoints unless otherwise specified.

In the present invention, with respect to the molecular weight of polymers, the terms "about" and "approximately" generally suggest a ±10% numerical range which in some cases can be increased to ±15% but no greater than ±20%, with the preset value as the base value. For example, the deviations of 11 kDa and 12 kDa relative to 10 kDa are 10% and 20%, respectively; therefore, "approximately 10 kDa" includes but is not limited to 11 kDa and 12 kDa. For example, provided that the molecular weight of a PEG component of a general formula is about 5 kDa, the corresponding molecular weight or number average molecular weight is allowed to be 5 kDa±10%, i.e., variable in the range of 4500~5500 Da.

In the present invention, with respect to percentages, the terms "about" and "approximately" generally suggest a $\pm(0.5*0.1^N)\%$ numerical range when the given value (without "%") is accurate to the Nth decimal place. For example, approximately 1% means $1\pm(0.5*0.1^0)\%$ (i.e., the range of 0.5%-1.5%), approximately 2.2% means $2.2\pm(0.5*0.1^1)\%$ (i.e., the range of 2.15%-2.25%), and approximately 2.33% means $2.33\pm(0.5*0.1^2)\%$ (i.e., the range of 2.335%-2.325%).

In the present invention, the degree of polymerization of a polyethylene glycol chain is represented by $n_i$, wherein i is an integer selected from 1, 2, 3, . . . ; unless otherwise specified, "≈" is used to indicate sameness or equality between degrees of polymerization. With respect to monodisperse polymers, "=" can also be used to indicate sameness or equality. $n_i$ of the same value in the same structure can interchangeably represent each other; for example, when $n_2 \approx n_3$, $n_2$ can be represented by $n_3$ and $n_3$ can also be represented by $n_2$.

In the present invention, unless otherwise specified, a divalent linking group can be connected to another group using either one of its two connecting ends. For example, when an amide bond is used as a divalent linking group between GroupA and GroupB, both GroupA-C(═O)NH-GroupB and GroupA-NHC(═O)-GroupB are allowable.

With respect to the structural representation in the present invention, when it comes to the ownership problem of atoms of connected groups, "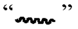" is used to indicate the linking bond. For example,

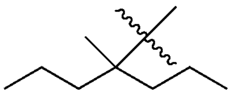 [SMILES: *C(C)(CCC)CCC]

represents the structure of a group; specifically,

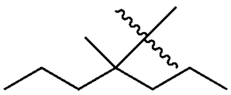 [SMILES: *C(C)(CCC)CCC]

represents $—CCH_3(CH_2CH_2CH_3)_2$ and

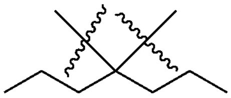 [SMILES: *C(*)(CCC)CCC]

represents —$C(CH_2CH_2CH_3)_2$—, while

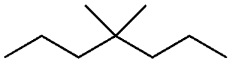

in the non-group form represents $(CH_3)_2C(CH_2CH_2CH_3)_2$.

In the present invention, with respect to a linking bond or group extending out from a cyclic structure, when the connecting end points to the inside of the ring instead of marking any specific ring atom, it means that the linking bond or group can be connected to any appropriate ring atom. Moreover, when the ring is part of a fused ring system, the linking bond or group can be connected to any ring atom of the fused ring system. For example, the structure represented by

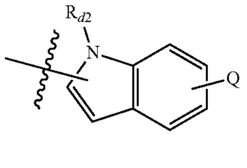

includes but is not limited to

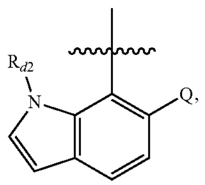,

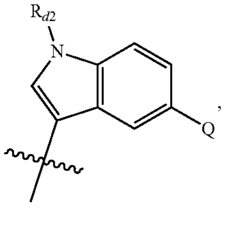

etc.

In the present invention, the range of the number of carbon atoms of a group can be represented in the form of a subscript at the subscript position of "C", and unless otherwise specified, the number of carbon atoms includes no contribution from substituents. For example, $C_{1-12}$ means "having 1 to 12 carbon atoms". For example, a $C_{1-10}$ alkylene group represents any alkylene group having the number of carbon atoms in the range indicated by the subscript, i.e., any one selected from the group consisting of $C_1$, $C_2$, $C_3$, $C_4$, $C_5$, $C_6$, $C_7$, $C_8$, $C_9$, and $C_{10}$ alkylene groups, including but not limited to a linear $C_{1-10}$ alkylene group (e.g., —$(CH_2)_6$—) and a branched $C_{1-10}$ alkylene group (e.g., —$(CH_2)_3$—$CH(CH_3)$—$(CH_2)_3$—). For example, a "substituted $C_{1-12}$ alkyl group" is selected from the group consisting of $C_1$, $C_2$, $C_3$, $C_4$, $C_5$, $C_6$, $C_7$, $C_8$, $C_9$, $C_{10}$, $C_{11}$ and $C_{12}$ alkyl groups, each having at least one hydrogen atom substituted with a substituent, without particular restriction on the number of carbon atoms or heteroatoms in the substituent.

In the present invention, when a structure involved has isomers, unless otherwise specified, it can be any of the isomers. For example, with respect to a structure having both cis- and trans-isomers, it can be either a cis structure or a trans structure; with respect to a structure having E/Z isomers, it can be either an (E)-structure or a (Z)-structure; and, when optical activity is involved, a structure can be either levo or dextro.

In the present invention, if a structural representation is inconsistent with the name of the structure, then the structural representation shall be prioritized.

In the present invention, the molecular weight of polyethylene glycol and its derivatives refers to the average molecular weight by default. Unless otherwise specified, the "average molecular weight" generally refers to the "number average molecular weight" ($M_n$). As for the number average molecular weight, it can be used as not only the molecular weight of polydisperse blocks or substances but also the molecular weight of monodisperse blocks or substances. Unless otherwise specified, the unit of measurement for molecular weight is dalton (Da). The molecular weight of polyethylene glycol chain can also be measured by the "degree of polymerization" which is, specifically, the number of repeat units (oxyethylene units). Accordingly, the average value and the number average value of the number of repeat units are preferably represented by "average degree of polymerization" and "number average degree of polymerization", respectively.

In the present invention, the term "any appropriate" in "any appropriate linking group", "any appropriate reactive group", etc., indicates that the structures follow the basic rule of chemical structures and can facilitate the successful implementation of the preparation methods in the present invention. Chemical structures described in this manner can be regarded as having a clear and defined scope.

In the present invention, the terms "stable" and "degradable" regarding a group are a pair of opposing concepts.

In the present invention, the term "degradable" means that a chemical bond in the present invention can be cleaved to obtain at least two independent residues. If a linking group with its structure altered after chemical changes still remains a complete linking group, then it is still within the scope of being "stable". The conditions for degradation are not particularly limited, which can be physiological conditions in vivo, simulated physiological environments in vitro, or other conditions, preferably physiological conditions in vivo or simulated physiological environments in vitro. Said physiological conditions are not particularly limited, which can be intracellular or in the extracellular matrix, in normal physiological tissues or in pathologic tissues (e.g., tumor, inflamed tissue, etc.), and in body parts including but not limited to serum, heart, liver, spleen, lung, kidney, bone, muscle, fat, brain, lymph node, small intestine, gonad, etc. Said simulated physiological environment in vitro is not particularly limited, including but not limited to physiological saline, buffer, culture medium, etc. The degradation is not particularly limited with respect to the rate, which can be, for example, rapid degradation via enzymolysis or slow hydrolysis under physiological conditions, etc. Said physiological conditions in vivo include physiological conditions during treatment, such as ultraviolet radiation, thermal therapy, etc. The conditions for degradation include but are not limited to light, heat, low temperature, enzyme, oxidation-reduction, acidity, basicity, physiological condition, simulated physiological environment in vitro, etc., preferably light, heat, enzyme, oxidation-reduction, acidity, basicity, etc. The degradation can occur under stimulation by any above-mentioned condition. Said light condition includes but is not limited to visible light, ultraviolet light, infrared light, near-infrared light, mid-infrared light, etc. Said heat condition refers to a temperature higher than the normal physiological temperature, which is generally above 37° C. and below 45° C., preferably below 42° C. Said low temperature condition refers to a temperature below the physiological temperature of human body, preferably below 25° C., and more preferably ≤10° C., with specific examples such as refrigeration temperature, freezer temperature, temperature for liquid nitrogen treatment, 2~10° C., 4~8° C., 4°

C., 0° C., −20±5° C., etc. Said enzyme is not particularly limited, and all enzymes that can be physiologically generated are included, e.g., peptidases, proteases, lyases, etc. Said oxidation-reduction is not particularly limited, e.g., oxidation-reduction transformation between a mercapto group and a disulfide bond, and hydrogenation-reduction transformation. Said acidic and basic conditions mainly refer to the pH conditions of internal body parts such as normal tissues, pathologic tissues, organs or tissues in treatment, etc.; for example, the stomach has an acidic condition, and tumor sites tend to be acidic as well. The degradation described herein can occur through metabolism in vivo (e.g., physiological effects, enzymes, oxidation-reduction, etc.), or under microenvironment stimulations (e.g., acidity and basicity) in specific in vivo sites, or under clinical therapeutic stimulations (e.g., light, heat, low temperature), etc. It should be noted that some conditions in organic chemistry that are extreme for living organisms, for example, strong acidity, strong basicity, high temperature (e.g., above 100° C.), etc., under which conditions a bond can be cleaved, are not considered to be within the scope of degradation conditions. For example, although an ether bond can be cleaved under strongly acidic conditions such as hydrobromic acid, it is always classified as a stable linking group in the present invention.

In the present invention, the term “stable” indicates that a linking group can keep existing as a complete linking group (i.e., a linking group which is stably and covalently connected to adjacent groups) and therefore it is defined as “stable”, allowing chemical changes without compromising the wholeness of the linking group. Said chemical changes are not particularly limited, including but not limited to isomerization, oxidation, reduction, ionization, protonation, deprotonation, substitution, etc. The conditions for stable existence are not particularly limited, including but not limited to light, heat, low temperature, enzyme, oxidation-reduction, neutrality, acidity, basicity, physiological condition, simulated physiological environment in vitro, etc., preferably light, heat, enzyme, oxidation-reduction, acidity, basicity, etc. The stable existence described herein indicates that, without particular stimulation (e.g., pH conditions in particular areas, and light, heat, low temperature in treatment, etc.), the stable connections can be maintained in the metabolic cycle in vivo and the molecular weight is not reduced by bond cleavage (as long as the structural integrity is maintained).

In the present invention, “stable” is not an absolute concept with respect to a specific linking group. For example, an amide bond is much more stable than an ester bond under acidic or basic conditions, and the “stable” linking group of the present invention includes the amide bond. However, the peptide bond, for example, is a kind of amide bond formed via the dehydration condensation of an α-carboxyl group of an amino acid molecule with an α-amino group of another amino acid molecule, which can be cleaved under specific enzymatic conditions and, therefore, is also classified as a “degradable” linking group. Similarly, carbamate group, thiocarbamate group, etc., are linking groups which can be stable or degradable. More commonly, carbamate group, thiocarbamate group, etc., tend to degrade slowly, while non-peptide amide bonds can remain stable in the metabolic cycle in vivo. As another example, a common ester bond can degrade under acidic or basic conditions, while an ester bond contained in a special structure can also degrade under UV exposure. As another example, even though some chemical bonds can degrade under specific enzymatic conditions, they can still be regarded as stable if their circulation in clinical use (e.g., site-directed administration) does not or basically not go through the specific enzymatic conditions.

In the present invention, all compounds of general formula should be regarded as including salts thereof. The term “salt” is selected from the group consisting of acid addition salts formed by the compounds and inorganic and/or organic acids, base addition salts formed by the compounds and inorganic and/or organic bases, and combinations of any two or more thereof. When a compound of general formula contains both a basic moiety (such as, but not limited to, a pyridine or imidazole) and an acidic moiety (such as, but not limited to, a carboxylic acid), a zwitterion (“inner salt”) can be formed and included in the term “salt”. The “salt” can be pharmaceutically acceptable (i.e., non-toxic, physiologically acceptable) or otherwise. Salts of compounds of general formula can be formed by reacting the compounds with an amount (e.g., an equivalent) of acid or base in a medium such as one in which the salt precipitates or in an aqueous medium followed by lyophilization. Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates, tartrates, thiocyanates, toluenesulfonates, undecanoates, etc. Exemplary base addition salts include ammonium salts, alkali metal salts (e.g., sodium, lithium, and potassium salts), alkaline earth metal salts (e.g., calcium and magnesium salts), salts with organic bases (e.g., organic amines), and salts with amino acids (e.g., arginine, lysine). Basic nitrogen-containing groups may be quaternized with agents such as lower alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, tetradecyl, and stearyl chlorides, bromides, and iodides), aralkyl halides (e.g., benzyl and phenethyl bromides), etc. Said acid addition salts and base addition salts are both preferably pharmaceutically acceptable salts, and should be regarded as equivalent to the free forms of corresponding compounds of general formula for the purpose of this disclosure.

In the present invention, heteroatoms are not particularly limited, including but not limited to O, S, N, P, Si, F, Cl, Br, I, B, etc.

In the present invention, relative to a compound, a group formed after losing part of atoms or groups of the compound is also termed a residue.

In the present invention, groups having a valence greater than or equal to 2 are collectively referred to as “linking groups”. A linking group may have only one atom, such as an ether group (—O—) and a thioether group (—S—). Particularly, when the definition of a group includes a “linking bond”, it means that the group may contain no atoms but only act as a linker.

In the present invention, regarding the valence of a group, the term “multivalent” indicates that the valence is at least 3.

In the present invention, unless otherwise specified, a “linking bond” only acts as a linker and does not contain any atoms.

In the present invention, the term "group" for divalent groups can be replaced by the term "bond", without changing the meanings. For example, a divalent ether group can be termed an ether bond (—O—), a divalent ester group can be termed an ester bond (—OC(=O)— or —C(=O)O—), and a divalent carbamate group can be termed a carbamate bond (—OC(=O)NH— or —NHC(=O)O—). Particularly, the "linking group" can not be termed the "linking bond".

In the present invention, when the number of atoms in a substituent is 1, the substituent can also be termed a "substituent atom".

In the present invention, when a compound or group is "substituted", it means that the compound or group contains one or more substituents.

In the present invention, unless otherwise specified, the term "amine group" can be used interchangeably with "amino group", including monovalent, divalent, trivalent, and quadrivalent neutral or cationic groups, substituted or unsubstituted. For example, the $—NH_2$ in $CH_3—NH_2$ can be termed an "amino group", "amine group", or "primary amine group". As another example, the —NH— in $CH_3—NH—CH_3$ can be termed a "secondary amine group" or "secondary amino group", wherein the $—NH—CH_3$ can also be interpreted as a methyl-substituted amine group.

In the present invention, the term "amine group" includes but is not limited to primary amine groups, secondary amine groups, tertiary amine groups, and quaternary ammonium ions.

Exemplary amine groups include $—NR_tR_t$ and $—N^+R_tR_tR_1$, wherein each $R_t$ is independently a hydrogen atom or any hydrocarbon group.

In the present invention, when the valence is undefined, a "hydrocarbon group" could be a monovalent, divalent, trivalent, . . . , or n-valent hydrocarbon group, wherein n is the highest possible valence of the hydrocarbon group.

In the present invention, a "hydrocarbylene group" is a divalent hydrocarbon group.

In the present invention, the secondary amine bond and the hydrazine bond are "—NH—" and "—NH—NH—", respectively, both capped by hydrocarbon groups at both ends, e.g., $—CH_2—NH—CH_2—$ and $—CH_2—NH—NH—CH_2—$. As a counterexample, —C(=O)—NH— is termed an amide bond, instead of being considered to contain a secondary amine bond.

In the present invention, a "group with functionality" is also termed a "functional group", which is preferably a reactive group, a protected reactive group, or a precursor of a reactive group, etc. The term "poly" indicates that the number of functional groups is at least 3; for example, a polyol is a compound having at least 3 hydroxyl groups, a polythiol is a compound having at least 3 thiol groups, etc. What should be noted is that heterofunctional groups of other types are also allowed. For example, tris(hydroxymethyl)aminomethane is a triol containing also an amino group, and citric acid is a tricarboxylic acid containing also a hydroxyl group.

With respect to the preparation methods in the present invention, unless otherwise specified, reactive groups also include protected forms thereof, and the protected forms may be deprotected in any appropriate step in the actual preparation process to obtain the corresponding reactive forms.

In the present invention, ring atoms are the atoms that together constitute the ring skeleton.

In the present invention, the source of an amino acid is not particularly limited unless otherwise specified, which can be a natural source, a non-natural source, or a mix of both. The structural type of an amino acid in the present invention is not particularly limited unless otherwise specified, which can be L-type, D-type, or a mix of both.

In the present invention, the definitions and illustrations of the skeletons of amino acids, the skeletons of amino acid derivatives, and the skeletons of cyclic monosaccharides in documents including CN104877127A, WO/2016/206540A, CN106967213A, CN108530637A, CN108530617A and all cited documents, are hereby incorporated by reference. Unless otherwise specified, the skeletons are also residues. Wherein, an amino acid residue includes the amino acid with a hydrogen atom removed from its amino group and/or a hydroxyl group removed from its carboxyl group and/or a hydrogen atom removed from its thiol group and/or its amino group being protected and/or its carboxyl group being protected and/or its thiol group being protected. Imprecisely, an amino acid residue can also be termed an amino acid. Specific examples include residues formed by losing a carboxylic hydroxyl group (including every carboxylic hydroxyl group at the C-terminus as well as the carboxylic hydroxyl group in the pendant group of aspartic acid or glutamic acid), a hydrogen atom in a hydroxyl group, a hydrogen atom in a phenolic hydroxyl group (e.g., tyrosine), a hydrogen atom in a thiol group (e.g., cysteine), a hydrogen atom at a nitrogen atom (including every hydrogen atom at the N-terminus as well as the hydrogen atom in an amino group of a pendant group such as the hydrogen atom in the F-amino group of lysine or ornithine and the hydrogen atom in the amino group of the pendant ring of histidine or tryptophan), an amino group in an amide (e.g., asparagine, glutamine), an amino group in a pendant group of a guanidine, or a hydrogen atom in an amino group. Besides having the essential characteristics of an amino acid, a residue of amino acid derivative also has atomic or group moieties with the essential characteristics of a non-amino acid.

In the present invention, the term "bio-related substance" includes but is not limited to the substances described, listed, or referred to in documents including CN104877127A, WO/2016/206540A, CN106967213A, CN108530637A, CN108530617A and all cited documents. In general, bio-related substances include but are not limited to the following substances: drugs, proteins, polypeptides, oligopeptides, protein mimics, fragments and analogs, enzymes, antigens, antibodies and their fragments, receptors, small molecule drugs, nucleosides, nucleotides, oligonucleotides, antisense oligonucleotides, polynucleotides, nucleic acids, aptamers, polysaccharides, proteoglycans, glycoproteins, steroids, steroid compounds, lipid compounds, hormones, vitamins, phospholipids, glycolipids, dyes, fluorescent substances, targeting factors, targeting molecules, cytokines, neurotransmitters, extracellular matrix substances, plant or animal extracts, viruses, vaccines, cells, vesicles, liposomes, micelles, etc. Said bio-related substances refer to not only themselves but also their precursors, activated states, derivatives, isomers, mutants, analogs, mimics, polymorphs, pharmaceutically acceptable salts, fusion proteins, chemically modified substances, genetically recombined substances, and also the corresponding agonists, activating agents, activators, inhibitors, antagonists, modulators, receptors, ligands or ligand groups, antibodies and fragments thereof, acting enzymes (e.g., kinases, hydrolases, lyases, oxoreductases, isomerases, transferases, deaminases, deiminases, invertases, synthetases, etc.), enzyme substrates (e.g., coagulation cascade protease substrates, etc.), etc. Said derivatives include but are not limited to the derivatives of glycosides, nucleosides, amino acids, and polypeptides. Chemically modified products with newly formed reactive groups, i.e., modified products obtained by changing the types of reactive groups via modification or by introducing extra structures such as functional groups, reactive groups, amino acids or derivatives thereof, polypeptides, etc., are all within the scope of chemically modified substances of bio-related substances. Before or after bio-related substances combine with functionalized compounds, it is allowed that there are target molecules to be combined with, appendages, or delivery vectors to form modified bio-related substances or complex bio-related substances. Wherein, the pharmaceutically acceptable salts can be inorganic salts such as hydrochlorides, sulfates, and phosphates, or organic salts such as oxalates, malates, citrates, etc. Wherein, "drugs" in the present invention include any agents, compounds, compositions, and mixtures with physiological or pharmacological effects in vivo or in vitro, and the effects are usually beneficial. Said drugs are not particularly limited with respect to the type, including but not limited to pharmaceuticals, vaccines, antibodies, vitamins, food, food additives, nutritional supplements, nutraceuticals, and other agents providing beneficial effects. Said "drugs" are not particularly limited with respect to the range of physiological or pharmacological effects in vivo, which can be effective for the whole body or only at local sites. Said "drugs" are not particularly limited with respect to the activity, mainly the active substances capable of interacting with other substances or the inert substances which are non-interactive; however, the inert substances can be transformed into active forms by in vivo effects or certain stimulations. Wherein, "small molecule drugs" are bio-related substances with molecular weight not exceeding 1000 Da, or small molecule mimics or active fragments of any bio-related substance.

In the present invention, the term "oligopeptide" refers to a peptide-type molecule formed by two or more amino acids, wherein the number of amino acid residues constituting the oligopeptide is preferably 2 to 20. An "oligopeptide residue" can be monovalent, divalent, trivalent or higher valent.

In the present invention, unless otherwise specified, the term "monosaccharide group" refers to the residue of monosaccharide, i.e., the skeleton of monosaccharide, including open-chain monosaccharide groups and cyclic monosaccharide groups (e.g., furanose ring and pyranose ring).

Monosaccharide groups in the present invention can be selected from the residues of compounds including but not limited to monosaccharides, sugar alcohols, deoxy sugars, amino sugars, amino sugar derivatives (e.g., amide derivatives), sugar acids, and glycosides, with open-chain or cyclic structures. Examples include the amino residue formed by removing an amino hydrogen atom of an amino sugar, the acyl group formed by removing a carboxylic hydroxyl group of a sugar acid, etc. Said monosaccharides include but are not limited to aldoses (polyhydroxy aldehydes) and ketoses (polyhydroxy ketones). Examples also include alkyl ether derivatives, specifically, e.g., methyl ether derivatives, and more specifically, e.g., quebrachitol. Monosaccharide groups in the present invention are not particularly limited with respect to the number of carbon atoms, including but not limited to tetroses, pentoses, hexoses, and heptoses, preferably pentoses and hexoses. Wherein, exemplary tetroses, pentoses, hexoses, heptoses, sugar alcohols, deoxy sugars, amino sugars, amide derivatives of amino sugars, sugar acids, glycosides, etc., include but are not limited to the structures disclosed in CN106967213A.

In the present invention, the "micro-modification" refers to a chemical modification process that can be realized by simple chemical reactions. Said simple chemical reactions mainly include protection, deprotection, salt complexation, decomplexation, ionization, protonation, deprotonation, changing leaving groups, etc.

In the present invention, the "micro-modified form" corresponds to the "micro-modification", referring to a structural form that can be transformed into the target reactive group after simple chemical reactions such as protection, deprotection, salt complexation, decomplexation, ionization, protonation, deprotonation or changing leaving groups, etc. Said changing leaving groups, i.e., transformation of leaving groups, includes but is not limited to the transformation of an ester form to an acyl chloride form.

In some specific embodiments of the present invention, the reaction process also involves "protection" and "deprotection" of relevant groups. To avoid the influence of a certain reactive group on the reaction, the reactive group is usually protected. In some specific embodiments of the present invention, when 2 or more reactive groups are present, the target reactive group should be selectively used for the reaction, and therefore the other reactive groups should be protected. The protecting groups not only remain stable during the target reaction process but can also, as needed, be removed by conventional technical means in the art.

In the present invention, the "protection" of a reactive group refers to a strategy for reversibly transforming the reactive group in need of protection to an inert group (i.e., non-reactive group) using particular reagents. Within a protected group, the moiety that distinguishes the protected form from the unprotected form is regarded as the "protecting group". For example, —OTBS is a protected form of hydroxyl group (—OH), wherein the -TBS group is the hydroxyl protecting group.

In the present invention, the terms "deprotection" and "removal of protection" have the same meaning, both referring to the process of transforming a protected group to its unprotected form.

In the present invention, the term "hydroxyl protecting group" includes all the groups that can be used as common hydroxyl protecting groups, preferably alkanoyl (e.g., acetyl, butyryl), aromatic alkanoyl (e.g., benzoyl), benzyl, triphenylmethyl, trimethylsilyl, t-butyldimethylsilyl, allyl, acetal, or ketal groups. The removal of acetyl groups is generally carried out under basic conditions, most commonly by the ammonolysis with $NH_3$/MeOH or by the methanolysis catalyzed by methanol anions. Benzyl groups can be easily removed via palladium-catalyzed hydrogenolysis in a neutral solution at room temperature, or via reduction reaction with metallic sodium in ethanol or liquid ammonia. Triphenylmethyl groups are generally removed via catalytic hydrogenolysis. Trimethylsilyl groups are generally removed using reagents containing fluoride ions (e.g., tetrabutylammonium fluoride/anhydrous THF, etc.). The t-butyldimethylsilyl ether is relatively stable, which can withstand ester hydrolysis conditions with alcoholic potassium hydroxide as well as mild reduction conditions (e.g., $Zn/CH_3OH$, etc.), but can be removed by fluoride ions (e.g., $Bu_4N^+F^-$) in a tetrahydrofuran solution or by aqueous acetic acid at room temperature. The protection of diols preferably forms dioxolanes, dioxanes, cyclic carbonates, or cyclic borates.

In the present invention, the term "thiol protecting group" includes all the groups that can be used as common thiol protecting groups. Similar to hydroxyl groups, thiol groups can be protected in the form of thioethers or thioesters. Thiol protecting groups are preferably tert-butyl, benzyl, substituted benzyl, benzhydryl, substituted benzhydryl, trityl, acetyl, benzoyl, tert-butoxycarbonyl, benzyloxycarbonyl, thioacetal, or thioketal groups. The deprotection of thioethers can be realized by acid-catalyzed reduction using $Na/NH_3$, or by reactions with heavy metal ions (e.g., $Ag^+$, $Hg^+$) followed by treating with hydrogen sulfide. Some groups such as hemi-thioacetals containing S-diphenylmethyl, S-triphenylmethyl thioether, S-2-tetrahydropyranyl, or S-isobutoxymethyl groups can be oxidized to disulfides by $(SCN)_2$, iodine, or thionyl chloride, and further reduced to thiols. The formation of thioester and the corresponding deprotection methods are the same as those of carboxylates.

In the present invention, the term "carboxyl protecting group" refers to a protecting group that can be transformed into a carboxyl group via hydrolysis or via the deprotection of the carboxyl protecting group. A carboxyl protecting group is preferably an alkyl (e.g., methyl, ethyl, and butyl) or aralkyl (e.g., benzyl) group, and more preferably a butyl (tBu), methyl (Me), or ethyl (Et) group. In the present invention, the "protected carboxyl group" is a group formed by protecting a carboxyl group with an appropriate carboxyl protecting group, preferably a methoxycarbonyl group, an ethoxycarbonyl group, a t-butyloxycarbonyl group, or a benzyloxycarbonyl group. Said carboxyl protecting groups can be removed through hydrolysis catalyzed by acids or alkalis, or through pyrolysis reactions occasionally. For example, t-butyl groups can be removed under mild acidic conditions, and benzyl groups can be removed by hydrogenolysis. The reagent used for the removal of a carboxyl protecting group is selected from the group consisting of TFA, $H_2O$, LiOH, NaOH, KOH, MeOH, EtOH, and combinations thereof, preferably the combination of TFA and $H_2O$, the combination of LiOH and MeOH, or the combination of LiOH and EtOH. The deprotection of a protected carboxyl group can produce the corresponding free acid, which could be carried out in the presence of an alkali that forms pharmaceutically acceptable salts with the free acid generated during the deprotection.

In the present invention, the term "amino protecting group" is equivalent to "amine protecting group", including all the groups that can be used as common amino/amine protecting groups, such as aryl $C_{1-6}$ alkyl groups, $C_{1-6}$ alkoxy $C_{1-6}$ alkyl groups, $C_{1-6}$ alkoxycarbonyl groups, aryloxycarbonyl groups, $C_{1-6}$ alkylsulfonyl groups, arylsulfonyl groups, methylsilyl groups, etc. An amino protecting group is preferably selected from the group consisting of a t-butoxycarbonyl (Boc) group, a p-methoxybenzyloxycarbonyl (Moz) group, and a 9-fluorenylmethoxycarbonyl (Fmoc) group. The reagent used for the removal of an amino protecting group includes but is not limited to TFA, $H_2O$, LiOH, MeOH, EtOH, and combinations thereof, preferably the combination of TFA and $H_2O$, the combination of LiOH and MeOH, or the combination of LiOH and EtOH. The reagent used for the removal of Boc can be TFA or HCl/EA, preferably TFA. The reagent used for the removal of Fmoc can be the solution of 20% piperidine in N,N-dimethylformamide (DMF).

In the present invention, the term "alkynyl protecting group" includes all the groups that can be used as common alkynyl protecting groups, preferably a trimethylsilyl (TMS), triethylsilyl, tert-butyldimethylsilyl (TBS), or biphenyldimethylsilyl group. The TMS-protected alkynyl groups can be easily deprotected under basic conditions, for example, $K_2CO_3$/MeOH or KOH/MeOH. The TBS-protected alkynyl groups can be deprotected in the solution of tetra-n-butylammonium fluoride in tetrahydrofuran (TBAF/THF).

In the present invention, hydroxyl groups that can be protected by hydroxyl protecting groups are not particularly limited, e.g., alcoholic hydroxyl groups and phenolic hydroxyl groups. Amino/amine groups that can be protected by amino protecting groups are not particularly limited, e.g., amino groups of primary amines, secondary amines, hydrazines, and amides. Amine groups in the present invention are not particularly limited, including but not limited to primary amine groups, secondary amine groups, tertiary amine groups, and quaternary ammonium ions.

In the present invention, the deprotection of protected hydroxyl groups is related to the type of hydroxyl protecting group. Said type of hydroxyl protecting group is not particularly limited; for example, benzyl, silyl ether, acetal, or tert-butyl groups can be used to protect terminal hydroxyl groups, and the corresponding deprotection methods include but are not limited to the following:

A: Removal of Benzyl Groups

The removal of benzyl groups can be achieved via hydrogenation using hydrogenation reducing agents and hydrogen donors. The water content in this reaction system should be less than 1% so that the reaction can proceed smoothly.

The catalyst for hydrogenation reduction is not particularly limited, preferably palladium or nickel. The catalyst support is not particularly limited, preferably aluminum oxide or carbon, and more preferably carbon. The amount of palladium used is 1 to 100 wt % relative to the compounds containing protected hydroxyl groups, preferably 1 to 20 wt % relative to the compounds containing protected hydroxyl groups.

The reaction solvent is not particularly limited, as long as it can dissolve both the starting materials and the products, but is preferably methanol, ethanol, ethyl acetate, tetrahydrofuran, or acetic acid, more preferably methanol. The hydrogen donor is not particularly limited, but is preferably gaseous hydrogen, cyclohexene, 2-propanol, or ammonium formate, etc. The reaction temperature is preferably in the range of 25 to 40° C. The reaction time is not particularly limited, which is negatively correlated with the amount of catalyst used and preferably in the range of 1 to 5 hours.

B: Deprotection of Acetals and Ketals

The compounds used for protecting hydroxyl groups in the form of acetals or ketals are preferably ethyl vinyl ether, tetrahydropyran, acetone, 2,2-dimethoxypropane, or benzaldehyde, etc. The deprotection of such acetals or ketals can be realized under an acidic condition wherein the pH of the solution is preferably 0 to 4. The acid used is not particularly limited, but is preferably acetic acid, phosphoric acid, sulfuric acid, hydrochloric acid, or nitric acid, and more preferably hydrochloric acid. The reaction solvent is not particularly limited, as long as it can dissolve the reactants and the products, but is preferably water. The reaction temperature is preferably 0 to 30° C.

C: Deprotection of Silyl Ethers

The protected hydroxyl groups in the form of silyl ethers include trimethylsilyl ether, triethylsilyl ether, tert-butyldimethylsilyl ether, tert-butyldiphenylsilyl ether, etc. The deprotection of such silyl ethers uses compounds containing fluoride ions which are preferably tetrabutylammonium fluoride, tetraethylammonium fluoride, hydrofluoric acid, or potassium fluoride, and more preferably tetrabutylammonium fluoride or potassium fluoride. The molar equivalent of the fluorine-containing compound used is 5 to 20 times that of the protected hydroxyl group, preferably 8 to 15 times. If the molar equivalent of the fluorine-containing compound used is less than 5 times that of the protected hydroxyl group, the deprotonation will be incomplete. If the molar equivalent of the deprotection reagent used exceeds 20 times that of the protected hydroxyl group, the excess reagents or compounds will bring difficulty to purification and will possibly enter the subsequent steps to cause side reactions. The reaction solvent is not particularly limited, as long as it can dissolve the reactants and the products, but is preferably an aprotic solvent and more preferably tetrahydrofuran or dichloromethane. The reaction temperature is preferably 0 to 30° C.; if the temperature is lower than 0° C., the reaction rate will be relatively slow and the protecting group will not be completely removed.

D: Removal of Tert-Butyl Groups

The removal of tert-butyl groups is carried out under an acidic condition wherein the pH of the solution is preferably 0 to 4. The acid used is not particularly limited, but is preferably acetic acid, phosphoric acid, sulfuric acid, hydrochloric acid, or nitric acid and more preferably hydrochloric acid. The reaction solvent is not particularly limited, as long as it can dissolve the reactants and the products, but is preferably water. The reaction temperature is preferably 0 to 30° C.

In the present invention, the term "activation of carboxyl group" refers to the activation of carboxyl groups with carboxyl activating agents. The activated carboxyl groups can promote condensation reactions, for example, by inhibiting the generation of racemic impurities, by accelerating the reactions through catalysis, etc. The "carboxyl activating group" is a residue of a carboxyl activating agent. Said carboxyl activating agent is selected from the group consisting of N-hydroxysuccinimide (NHS), 1-ethyl-3-(3-dimethylaminopropyl)carbodiimide hydrochloride (EDCI), N-hydroxy-5-norbornene-2,3-dicarboximide (HONb), N,N'-dicyclohexylcarbodiimide (DCC), and combinations thereof, preferably the combination of NHS/EDCI, NHS/DCC, or HONb/DCC, and more preferably the combination of NHS/EDCI or NHS/DCC.

In the present invention, the condensing agents used in reactions are not particularly limited, preferably selected from the group consisting of N,N'-dicyclohexylcarbodiimide (DCC), 1-ethyl-3-(3-dimethylaminopropyl)carbodiimide hydrochloride (EDC-HCl), o-(7-azabenzotriazol-1-yl)-N,N,N',N'-tetramethyluronium hexafluorophosphate (HATU), and o-(benzotriazol-1-yl)-N,N,N',N'-tetramethyluronium hexafluorophosphate (HBTU), most preferably DDC. Generally, the molar equivalent of the condensing agent used is 1 to 20 times that of carboxylic acids, preferably 5 to 10 times. Appropriate catalysts (e.g., 4-dimethylaminopyridine (DMAP)) can be added in this reaction.

In the present invention, the obtained products can be purified via purification methods including but not limited to extraction, recrystallization, adsorption treatment, precipitation, reverse precipitation, membrane dialysis, supercritical extraction, etc.

In the present invention, stepwise/multi-step reactions can be completed by a technical personnel in multiple practical operations, or in a single practical operation. For instance, in a reaction system of a practical operation, two reactive groups in one molecule of a low-molecular-weight lipid compound both undergo coupling reactions with a single-chain polyethylene glycol derivative reagent to obtain a non-linear PEGylated lipid compound with two single-chain PEG arms; considering that the two coupling reactions actually occur successively, the whole process can also be regarded as introducing polyethylene glycol components in a stepwise/multi-step way.

In the present invention, reactions can be solvent-free or using aprotic solvents. The aprotic solvent includes toluene, benzene, xylene, acetonitrile, ethyl acetate, diethyl ether, tert-butyl methyl ether, tetrahydrofuran, chloroform, dichloromethane, dimethylsulfoxide, dimethylformamide, and dimethylacetamide, and is preferably tetrahydrofuran, dichloromethane, dimethylsulfoxide, or dimethylformamide.

In the present invention, the bases used in reactions can be organic bases (e.g., triethylamine, pyridine, 4-dimethylaminopyridine, imidazole, or N,N-diisopropylethylamine, preferably triethylamine or pyridine), or inorganic bases (e.g., $K_2CO_3$).

In the present invention, the repeat unit of polyethylene glycol is the oxyethylene unit, i.e., $-CH_2CH_2O-$ or $-OCH_2CH_2-$, also termed the EO unit. The number of repeat units is also termed the number of EO units. The average number of repeat units is also termed the average number of EO units, which is preferably the number-averaged mean value.

In the present invention, for polydisperse cases, the term "identical", "same" or "equal" (including other forms of equivalent expressions) with respect to the molecular weight/degree of polymerization of a single compound molecule and the number average molecular weight/number average degree of polymerization of a compound component in macroscopic matter, unless otherwise specified, does not indicate a strict equality but a proximity or approximate equality of values, wherein the proximity or approximate equality preferably corresponds to a deviation within 10% and the preset value is generally used as the base value.

In the present invention, for monodisperse cases, the same or equal numbers of oxyethylene units with respect to a single compound molecule or a general formula are strictly equal in value. For example, provided that the number of EO units of a certain PEG component is 11, the value 12 is not within the preset scope. However, in order to obtain a compound component having the preset number of EO units, particular preparation methods might be used, and therefore the macroscopic matter obtained could also contain components having other numbers of EO units besides the component having the target number of EO units due to the limitations of preparation or purification methods; in this case, if the deviation between the average number of EO units and the preset number of EO units is within ±5% (base value≥10) or within ±0.5 (base value<10), it is considered to have obtained a monodisperse macroscopic matter containing the target component. Moreover, if the content of components having the number or average number of EO units within the allowed deviation reaches specific percentages (preferably ≥90%, more preferably >95%, more preferably >96%, more preferably >98%, and more preferably 99-100%), it is also considered to have obtained the monodisperse macroscopic matter containing the target component; even if the aforementioned content in percentage is not met, the product as well as the component in the form of main product, co-product or by-product, which are insufficient in content, are all within the scope of the present invention as long as they are prepared using the preparation methods of the present invention or any similar methods adopting basically the same ideas, with or without isolation or purification.

In the present invention, when Da, kDa, the number of repeat units, or the number of EO units is used to describe the molecular weight of a compound of general formula for polydisperse components, the value of molecular weight is allowed to be within a certain range around the given value (with endpoints included, and preferably within ±10%) with respect to a single compound molecule. When the number of oxyethylene units is used to describe the preset molecular weight of a compound of general formula for monodisperse components, the number is not a variable value in a range but a discrete point while the average number of EO units of the prepared product could be variable within a certain range (within ±10% or ±1, preferably within ±5% or ±0.5) due to non-uniform molecular weights. For example, provided that the molecular weight of an mPEG (methoxy polyethylene glycol) is 5 kDa, it means that the molecular weight of a single molecule of general formula is in the range of 4500-5500 Da and the average molecular weight of the corresponding components in the product is 5 kDa; i.e., the product with the average molecular weight in the range of 4500-5500 Da is regarded as the target product, and only the components with molecular weight in the range contribute to the content of the target component. As another example, provided that an mPEG is designed to have 22 oxyethylene units, all the compound molecules of general formula should have the number of EO units being strictly 22 while the prepared product could be a mixture of compounds having different numbers of EO units being 20, 21, 22, 23, or 24; meanwhile, if the average number of EO units is within the range of 22±2.2 (preferably in the range of 22±1.1), then the target component is considered obtained and all the components with molecular weight within the range can be regarded as the target component for calculation of purity.

In the present invention, unless otherwise specified, the term "mPEG" refers to a polyethylene glycol chain capped with a methoxy group, having the structure of

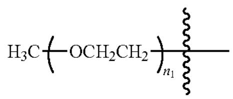 or 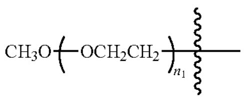, wherein $n_i$ is the degree of polymerization of the polyethylene glycol chain and is an integer selected from 1-1000.

In the present invention, a product with PDI<1.005 is regarded as monodisperse (PDI=1).

In the present invention, the number of repeat units in a "single-chain component" is at least 2.

In the present invention, the "lipid" includes but is not limited to esters of fatty acids and is generally characterized by poorer solubility in water and being soluble in many nonpolar organics. Although lipids usually have poorer solubility in water, some types of lipids (e.g., lipids modified with polar groups, such as DMG-PEG2000) have limited water solubility and can be dissolved in water under certain conditions. The known types of lipids include biomolecules such as fatty acids, waxes, sterols, fat-soluble vitamins (e.g., vitamins A, D, E, and K), monoglycerides, diglycerides, triglycerides, and phospholipids.

In the present invention, lipids include simple esters, compound esters, and derived lipids. Said simple esters are esters formed by fatty acids and alcohols, which can also be classified into three subcategories: fats, oils, and waxes. Said compound esters are "lipoid compounds" which are also termed "lipoids", including phospholipids, sphingolipids, glycolipids, steroids, sterols, and lipoproteins. Said derived lipids include simple lipid derivatives and compound lipid derivatives, having the general properties of lipids.

In the present invention, lipids can be synthetic or derived (separated or modified) from natural sources or compounds.

In the present invention, the term "liposome" refers to a closed vesicle formed by the self-assembly of lipids, having one or more lipid bilayer structures.

In the present invention, the term "lipid nanoparticle" or "LNP" refers to a nano-sized (e.g., 1 to 1000 nm) particle that contains one or more types of lipid molecules. In the present invention, the LNP can further contain at least one type of non-lipid payload molecule (e.g., one or more types of nucleic acid molecules). In some embodiments, the LNP contains a non-lipid payload molecule either partially or completely encapsulated inside a lipid shell. Particularly, in some embodiments, the payload is a negatively charged molecule (e.g., mRNA encoding a viral protein), and the lipid components of the LNP include at least one type of cationic lipid and at least one type of PEGylated lipid. It can be expected that the cationic lipids can interact with the negatively charged payload molecules and facilitate the incorporation and/or encapsulation of the payload into the LNP during LNP formation. As provided herein, other lipids that can be part of an LNP include but are not limited to neutral lipids and steroid lipids.

In the present invention, the term "cation" refers to a structure that is positively charged either permanently or non-permanently in response to certain conditions (e.g., pH). Therefore, cations include not only permanent cations but also those cationisable. Permanent cations refer to the corresponding compounds, groups, or atoms that are positively charged under conditions of any pH value or hydrogen ion activity of its environment. As a typical example, the presence of a quaternary nitrogen atom results in a positive charge. When a compound carries multiple positive charges, it can also be termed a polycation. A cationisable substance refers to a compound, group, or atom that is positively charged at a lower pH and uncharged at a higher pH of its environment. Moreover, in non-aqueous environments where the pH cannot be determined, a cationisable compound, group, or atom is positively charged at a high concentration of hydrogen ions and uncharged at a low concentration or activity of hydrogen ions. It depends on the individual properties of the cationisable or polycationisable compound, in particular the pKa of the respective cationisable group or atom, at which pH or hydrogen ion concentration the compound is charged or uncharged. In diluted aqueous environments, the fraction of cationisable compounds, groups, or atoms that are positively charged may be estimated using the so-called Henderson-Hasselbalch equation which is well-known to a person skilled in the art. In some embodiments, a cationisable compound or its moiety is positively charged at the physiological pH (e.g., approximately 7.0-7.4). In some preferred embodiments, a cationisable compound or its moiety is neutral at the physiological pH (e.g., approximately 7.0-7.4), but becomes positively charged at a lower pH (e.g., approximately 5.5-6.5). In some embodiments, the preferred range of pKa of the cationisable compound or its moiety is from approximately 5 to approximately 7.

In the present invention, the term "cationic lipid" refers to a lipid that is positively charged at any pH or hydrogen ion activity of its environment, or a cationisable lipid which can be positively charged in response to the pH or hydrogen ion activity of its environment (e.g., the expected environment for its use). Therefore, the term "cationic" includes the scopes of both "permanently cationic" and "cationisable". In some embodiments, the positive charge of a cationic lipid originates from the existence of a quaternary nitrogen atom. In some embodiments, cationic lipids include zwitterionic lipids that can be positively charged in the expected environment for their use (e.g., at the endosomal pH). In some embodiments, if a liposome or LNP contains cationisable lipids, it is preferred that about 1% to 100% cationisable lipids are cationized at a pH of about 1 to 9, preferably 4 to 9, 5 to 8, or 6 to 8, and more preferably at the endosomal pH (e.g., about 5.5 to 6.5). Cationic lipids include but are not limited to N,N-dioleyl-N,N-dimethylammonium chloride (DODAC), N,N-distearyl-N,N-dimethylammonium bromide (DDAB), N-[1-(2,3-dioleoyloxy)propyl]-N,N,N-trimethylammonium chloride (DOTAP), N-[1-(2,3-dioleyloxy)propyl]-N,N,N-trimethylammonium chloride (DOTMA) N,N-dimethyl-2,3-dioleyloxy-1-(dimethylamino)propane (DODMA), 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), ((4-hydroxybutyl)azanediyl)bis(hexane-6,1-diyl)bis(2-hexyldecanoate) (ALC-0315), heptadecan-9-yl 8-((2-hydroxyethyl)(6-oxo-6-(undecyloxy)hexyl)amino)octanoate (SM102), the cationic lipids disclosed in CN113402405A, and mixtures thereof.

In the present invention, the term "PEGylated lipid" refers to a molecule containing both lipid and polyethylene glycol moieties. PEGylated lipids not only include those of the general formula (1) of the present invention, but also include but are not limited to polyethylene glycol-1,2-dimyristoyl-sn-glycerol (PEG-DMG), polyethylene glycol-1,2-distearoyl-sn-glycero-3-phosphoethanolamine (PEG-DSPE), PEG-cholesterol, polyethylene glycol-diacylglycamide (PEG-DAG), polyethylene glycol-dialkyloxypropyl (PEG-DAA), and specifically, PEG500-dipalmitoylphosphatidylcholine, PEG2000-dipalmitoylphosphatidylcholine, PEG500-distearylphosphatidylethanolamine, PEG2000-distearylphosphatidylethanolamine, PEG500-1,2-oleoylphosphatidylethanolamine, PEG2000-1,2-oleoylphosphatidylethanolamine, PEG2000-2,3-distearoylglycerol (PEG-DMG), etc.

In the present invention, the term "neutral lipid" refers to any of the many types of lipid substances existing in the form of uncharged species or neutral zwitterionic species at a chosen pH, preferably phospholipid. Such lipids include but are not limited to 1,2-dilinoleoyl-sn-glycero-3-phosphocholine (DLPC), 1,2-dimyristoyl-sn-glycero-phosphocholine (MPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dioleoylphosphatidylserine (DOPS), dipalmitoylphosphatidylglycerol (DPPG), palmitoyloleoylphosphatidylethanolamine (POPE), distearoylphosphatidylethanolamine (DSPE), dipalmitoylphosphatidylethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoylphosphatidylcholine, lysophosphatidylcholine, lysophosphatidylethanolamine (LPE), and compositions thereof. Neutral lipids can be synthetic or naturally sourced.

In the present invention, a "steroid lipid" is selected from the group consisting of cholesterol, coprostanol, sitosterol, ergosterol, campesterol, stigmasterol, brassicasterol tomatidine, ursolic acid, α-tocopherol, and compositions thereof.

In the present invention, a liposome/lipid nanoparticle can be termed a "PEGylated liposome/lipid nanoparticle" when containing PEGylated lipids, and termed a "cationic liposome/lipid nanoparticle" when containing cationic lipids, and termed either a "PEGylated liposome/lipid nanoparticle" or a "cationic liposome/lipid nanoparticle" when containing both PEGylated lipids and cationic lipids.

In the present invention, the term "N/P ratio" refers to the molar ratio of the nitrogen atoms in cationic lipids to the phosphate groups in nucleic acids.

In the present invention, the term "nucleic acid" refers to DNA, RNA, or a modified form thereof, including purine or pyrimidine bases in DNA (adenine "A", cytosine "C", guanine "G", thymine "T"), and purine or pyrimidine bases in RNA (adenine "A", cytosine "C", guanine "G", uracil "U").

In the present invention, the term "RNA" refers to a ribonucleic acid that may be naturally or non-naturally existing. For example, an RNA may include modified and/or non-naturally existing components such as one or more nucleobases, nucleosides, nucleotides, or linkers. An RNA may include a cap structure, a chain terminating nucleoside, a stem loop, a polyadenylation sequence and/or a polyadenylation signal. An RNA can have a nucleotide sequence encoding a polypeptide of interest. For example, an RNA can be a messenger RNA (mRNA). Translation of an mRNA encoding a particular polypeptide, for example, the in vivo translation of an mRNA inside a mammalian cell, can produce the encoded polypeptide. RNAs can be selected from the non-limiting group consisting of small interfering RNA (siRNA), asymmetrical interfering RNA (aiRNA), microRNA (miRNA), Dicer-substrate RNA (dsRNA), small hairpin RNA (shRNA), mRNA, single guide RNA (sgRNA), cas9 mRNA, and mixtures thereof.

In the present invention, an antisense oligonucleotide or small interfering RNA (siRNA) can inhibit the expression of the target gene and the target protein in vitro or in vivo.

In the present invention, FLuc mRNA can express the luciferase protein which emits bioluminescence in the presence of a fluorescein substrate, and therefore FLuc is commonly used in the culture of mammalian cells to measure gene expression and cell activity.

In the present invention, the term "inhibiting the expression of a target gene" refers to the ability of nucleic acids to silence, reduce, or inhibit the expression of a target gene. To examine the extent of gene silencing, a test sample (e.g., a sample of cells in culture expressing the target gene) is contacted with nucleic acids that inhibit the expression of the target gene. The expression of the target gene in the test sample or test animal is compared to that in a control sample (e.g., a sample of cells in culture expressing the target gene) which is not contacted with or administered the nucleic acids. The expression of the target gene in the control sample can be assigned a value of 100%. In particular embodiments, inhibition of the expression of the target gene is achieved when the level of target gene expression in the test sample relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%.

In the present invention, methods for determining the level of target gene expression include but are not limited to dot blots, northern blots, in situ hybridization, ELISA, immunoprecipitation, enzyme function, and phenotypic assays.

In the present invention, the term "transfection" refers to the introduction of a species (e.g., RNA) into a cell. Transfection may occur, for example, in vitro, ex vivo, or in vivo.

In the present invention, the term "antigen" typically refers to a substance that can be recognized by the immune system, preferably recognized by the adaptive immune system, and can trigger an antigen-specific immune response, for example, forming antibodies and/or antigen-specific T cells as a part of the adaptive immune response. Typically, the antigen may be or may contain a peptide or a protein that can be presented to T cells by MHC. In the sense of the present invention, the antigen may be a translation product of the provided nucleic acid molecule (preferably mRNA as defined herein). In this context, fragments, variants, and derivatives of peptides and proteins containing at least one epitope are also regarded as antigens.

In the present invention, the term "delivery" refers to providing an entity to the target, for example, delivering drugs and/or therapeutic agents and/or prophylactic agents to subjects that are tissues and/or cells of human and/or other animals.

In the present invention, the term "pharmaceutically acceptable carrier" refers to a diluent, adjuvant, excipient, or vehicle administered together with the therapeutic agent, which is, within the scope of sound medical judgement, suitable for contact with tissues of human and/or other animals without causing any excessive toxicity, irritation, allergic reaction, or other problems or complications corresponding to rational benefit/risk ratios. Pharmaceutically acceptable carriers that can be used in the pharmaceutical compositions in the present invention include but are not limited to sterile liquids, such as water and oil, including oils from petroleum, animals, vegetables, or synthetics, e.g., peanut oil, soybean oil, mineral oil, sesame oil, etc. When the pharmaceutical composition is administered intravenously, an exemplary carrier is water. Physiological saline, glucose, and aqueous glycerol solution can also be used as liquid carriers, especially for injection. Suitable pharmaceutical excipients include starch, glucose, lactose, sucrose, gelatin, maltose, chalk, silica gel, sodium stearate, glyceryl monostearate, talc, sodium chloride, defatted milk powder, glycerol, propylene glycol, water, ethanol, etc. Said compositions may also contain a small amount of humectant, emulsifier, or pH buffer as needed. Oral preparations may contain standard carriers, such as pharmaceutical grade mannitol, lactose, starch, magnesium stearate, sodium saccharin, cellulose, magnesium carbonate, etc. Specifically, excipients include but are not limited to anti-adherents, antioxidants, binders, coatings, compression aids, disintegrants, dyes (pigments), emollients, emulsifiers, fillers (diluents), film formers or coatings, flavors, fragrances, glidants (flow enhancers), lubricants, preservatives, printing inks, sorbents, suspending or dispersing agents, sweeteners, and water for hydration. More specifically, excipients include but are not limited to butylated hydroxytoluene (BHT), calcium carbonate, calcium phosphate, calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, phenyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (α-tocopherol), vitamin C, and xylitol.

In the present invention, pharmaceutical compositions can act systematically or locally. For this purpose, they can be administered via appropriate routes such as injection (e.g., intravenous, intraarterial, subcutaneous, intraperitoneal, and intramuscular injections, including instillation) or transdermal delivery, or via oral, buccal, transnasal, transmucosal, or topical routes, or in the form of ophthalmic preparation, or by inhalation. Regarding these routes of administration, the pharmaceutical compositions of the present invention can be administered in suitable dosage forms. Said dosage forms include but are not limited to tablets, capsules, lozenges, hard sugar agents, powders, sprays, creams, ointments, suppositories, gels, pastes, lotions, ointments, aqueous suspensions, injectable solutions, elixirs, and syrups.

In the present invention, vaccines are preventive or therapeutic materials that provide at least one antigen or antigenic function. An antigen or antigenic function can stimulate the body's adaptive immune system to provide an adaptive immune response.

In the present invention, treatment refers to patient management and care in order to resist diseases, obstacles, or symptoms, which is intended to delay the development of diseases, obstacles, or symptoms, reduce or alleviate symptoms and complications, and/or cure or eliminate diseases, obstacles, or symptoms. The patients to be treated are preferably mammals, especially humans.

1.2. Nitrogen-Branched PEGylated Lipids

In One Embodiment of the Present Invention provided herein is a nitrogen-branched PEGylated lipid having the structure represented by the general formula (1):

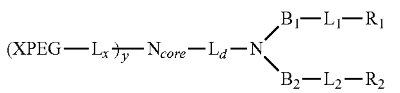

(1)

wherein, $B_1$ and $B_2$ are each independently a linking bond or an alkylene group;

$L_1$, $L_2$, $L_d$ and y instances $L_x$ are each independently a linking bond or the divalent linking group L;

$R_1$ and $R_2$ are each independently a $C_{1-50}$ aliphatic hydrocarbon group or a $C_{1-50}$ residue of aliphatic hydrocarbon derivative, containing 0-10 heteroatoms; the heteroatom is B, O, N, Si, P or S;

$N_{core}$ is a multivalent group having a valence of y+1; $N_{core}$ contains a trivalent nitrogen-atom branching core connected to $L_d$;

y is 2, 3, 4, 5, 6, 7, 8 or 9, or y≥10, preferably 2 or 3;

XPEG are polyethylene glycol components.

In the present invention, a compound of the general formula (1) can exist in an unsolvated or solvated form including the hydrated form. In general, for the purpose of the present disclosure, the solvated forms having pharmaceutically acceptable solvents (e.g., water, ethanol, etc.) are equivalent to the unsolvated forms.

In the present invention, a compound of the general formula (1) and its salts and solvates can exist in their tautomeric forms including those from keto-enol tautomerism, amide-imidic acid tautomerism, lactam-lactim tautomerism, enamine-imine tautomerism, proton transfer tautomerism and valence tautomerism.

In the present invention, a compound of the general formula (1) should be considered to include its salts, tautomers, stereoisomers and solvates.

In one specific embodiment of the present invention, any of XPEG contains x units of RPEG; y instances of x are each independently selected from integers of 1-4, and it is preferred that y instances of x are all 1; when y instances of x are all greater than or equal to 2, it is preferred that all x are equal;

the structure of RPEG is

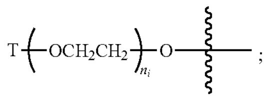

wherein, $n_i$ is the degree of polymerization of the polyethylene glycol chain, selected from integers of 4~250, and i is selected from integers of 1-20; the polyethylene glycol chain is polydisperse or monodisperse;

T is H, a $C_{1-6}$ alkyl group or $R_{01}$-$L_{01}$-;

$L_{01}$ is a linking bond or the divalent linking group L;

$R_{01}$ is a functional group that can interact with bio-related substances.

In one specific embodiment of the present invention, the aforementioned nitrogen-branched PEGylated lipid has the structure represented by the general formula (2):

(2)

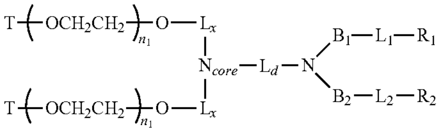

wherein, $n_1$ and $n_2$ are each independently selected from integers of 4-100, preferably selected from integers of 10-60, more preferably selected from integers of 10-45, and most preferably selected from integers of 10, 11, 12, 20, 21, 22, 23, 24, and 25.

1.2.1. Linking Groups

In the present invention, unless otherwise specified, all divalent linking groups are not particularly limited with respect to the stability. Any divalent linking group itself or one that consists of the divalent linking group and its adjacent heteroatom-containing groups are each independently a stable linking group or a degradable linking group.

In the present invention, unless otherwise specified, all divalent linking groups are not particularly limited with respect to the structure which can be a linear structure, a branched structure or a ring-containing structure. The number of non-hydrogen atoms in a divalent linking group is not particularly limited, each independently selected from integers of 0~20, preferably selected from integers of 1~10; wherein, the non-hydrogen atom is C, O, S, N, P, Si or B; when the number of non-hydrogen atoms is greater than 1, there are 1 type, 2 types, or more than 2 types of non-hydrogen atoms, and the non-hydrogen atoms are a combination of carbon and carbon atoms, a combination of carbon and hetero atoms, or a combination of hetero and hetero atoms.

In one specific embodiment of the present invention, the divalent linking group L is selected from the group consisting of an alkylene group, —C(═O)—, —OC(═O)—, —C(═O)O—, —OC(═O)O—, —O—, —S—, —S—S—, —C(═O)S—, —SC(═O)—, —$NR_c$—, —$NR_c$C(═O)—, —C(═O)$NR_c$—, —$NR_c$C(═O)$NR_c$—, —OC(═O)$NR_c$—, —$NR_c$C(═O)O—, —SC(═O)$NR_c$—, —$NR_c$C(═O)S— and combinations thereof, when a nitrogen-branched PEGylated lipid has two or more L, any two L have identical or different structures;

the alkylene group is —$(CR_cR_c)_t$—, wherein t is, at each occurrence, independently an integer in the range of 1-12, preferably an integer in the range of 1-4, and more preferably 1 or 2; $R_c$ is, at each occurrence, independently selected from the group consisting of H, a $C_{1-6}$ alkyl group, a carbocycle-containing group, a heterocycle-containing group, and a side-chain group of amino acid, preferably selected from the group consisting of H, a methyl group, an isopropyl group, an isobutyl group, and a benzyl group, more preferably H or a benzyl group, and most preferably H.

In one specific embodiment of the present invention, $L_1$ and $L_2$ are each independently selected from the group consisting of a linking bond, —O—, —C(═O)—, —OC(═O)—, —C(═O)O—, —NHC(═O)—, —C(═O)NH—, —OC(═O)O—, —OC(═O)NH—, and —NHC(═O)O—.

In one specific embodiment of the present invention, $L_x$ is, at each occurrence, independently selected from the group consisting of a linking bond, —$(CH_2)$—, —$(CH_2)_t$C(═O)$(CH_2)$—, —$(CH_2)_t$C(═O)O$(CH_2)_t$—, —$(CH_2)_t$OC(═O)$(CH_2)$—, —$(CH_2)_t$C(═O)NH$(CH_2)$—, and —$(CH_2)_t$NHC(═O)$(CH_2)_t$—; wherein, the t of $L_x$ is an integer in the range of 1-4, preferably 1 or 2; $L_x$ is preferably, at each occurrence, independently selected from the group consisting of —$CH_2CH_2$—, —$CH_2$C(═O)—, —C(═O)$CH_2$—, —C(═O)$CH_2CH_2$—, —$CH_2CH_2$C(═O)O$CH_2CH_2$—, and —C(═O)NH—.

In one specific embodiment of the present invention, each $L_x$ together with the divalent linking group —O— in XPEG form the divalent linking group —O-$L_x$;

each of y instances of $L_x$ independently corresponds to any of the following cases:

Case (1): $L_x$ is a linking bond;

Case (2): $L_x$ is a carbon-chain linking group, and is selected from the group consisting of a hydrocarbylene group, a carbonyl group, a carbon-chain linking group with a heteroatom-containing side group, and combinations thereof, Case (3): $L_x$ is a linking group with a heteroatom-containing main chain; it is preferred that $L_x$ or —O-$L_x$ is selected from the group consisting of an ether group, a thioether group, a disulfide bond, a diselenide bond, an ester group, a monothioester group, a dithioester group, a carbonate group, a monothiocarbonate group, a dithiocarbonate group, a trithiocarbonate group, a secondary amino group, an amide group, a carbamate group, a monothiocarbamate group, a dithiocarbamate group, an imine group, a triazole linking group, a 4,5-dihydroisoxazole linking group, a 2,5-dioxopyrrolidine linking group, and combinations of any one, two or more thereof and hydrocarbylene groups; it is more preferred that $L_x$ or —O-$L_x$ is selected from the group consisting of an ether group, an ester group, a disulfide bond, an amide group and a carbamate group;

Case (4): $L_x$ or —O-$L_x$ contains a linking group formed by a coupling reaction. $L_x$ or —O-$L_x$ is a linking group formed by an alkylation reaction, an amidation reaction, an esterification reaction, a thioesterification reaction, a click reaction, a cycloaddition reaction, a Diels-Alder addition reaction or a 1,3-dipolar cycloaddition reaction, or a combination of any one or more of the linking groups and hydrocarbylene groups.

In one specific embodiment of the present invention, $L_d$ is selected from the group consisting of a linking bond, —$(CR_cR_c)_t$—, —C(═O)—, —O—, —NH— and combinations thereof, wherein t is 1 or 2 and $R_c$ is H or a side-chain group of amino acid;

$L_d$ is preferably selected from the group consisting of —$CH_2CH_2$—, —$CH_2C$(═O)—, —$CH_2CH_2C$(═O)—, —$CH_2C$(═O)$NHCH_2CH_2$—, —$CH_2C$(═O)$OCH_2CH_2$—, —$CH_2CH_2C$(═O)$OCH_2CH_2$—, —$CH_2C$(═O)$NHCH_2C$(═O)—, —$CH_2C$(═O)$NHCH_2CH_2C$(═O)$OCH_2CH_2$—, —$CH_2CH_2C$(═O)$NHCH_2C$(═O)—, —$CH_2C$(═O)-Gly-Gly-$OCH_2CH_2$—, and —$CH_2C$(═O)-Phe-Gly-$OCH_2CH_2$—, and the left end of $L_d$ is connected to $N_{core}$; wherein, Gly is the residue of glycine and has the structure of —$NHCH_2C$(═O)—; Phe is the residue of phenylalanine and has the structure of

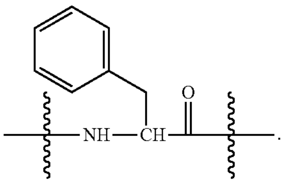 [SMILES: *NC(Cc1ccccc1)C(*)=O]

.

In one specific embodiment of the present invention, $L_d$ is a linking bond, an alkylene group, any one of the following classes, or a combination of any 1-4 of the following classes and alkylene groups:

(i) Covalent linking groups formed by coupling reactions involving any reactive group selected from the group consisting of amino, hydroxyl, carboxyl, mercapto, disulfide, diselenide, aldehyde, ketocarbonyl, guanidino, amido, azido, alkynyl, alkenyl, imidazolyl, and indolyl groups;

(ii) Amide group, secondary amino group, divalent tertiary amino group, carbamate group, thiocarbamate group, imine group, enamino group, aminoguanidino group, carbamimidamido group, imidate group, thioimidate group, ester group, carbonyl group, benzyloxycarbonyl group, thioester group, anhydride linking group, hydrazide group, acylhydrazone group, imide linking group, ether group, thioether group, disulfide bond, diselenide bond, guanidine-containing linking group, imidazole-containing linking group, triazole-containing linking group, 4,5-dihydroisoxazole linking group, vinyl ether bond, carbonate group, thiocarbonate group, dithiocarbonate group, trithiocarbonate group, dithiocarbamate group, acetal group, cyclic acetal group, thioacetal group, dithioacetal group, hemiacetal group, thiohemiacetal group, ketal group, thioketal group, oxime bond, thiooxime ether bond, semicarbazone bond, thiosemicarbazone bond, thiocarbohydrazide group, azocarbohydrazide group, azothiocarbohydrazide group, hydrazino formate group, hydrazino thioformate group, carbohydrazide group, thiocarbohydrazide group, allophanate group, thioallophanate group, guanidino group, amidino group, sulfonic acid group, sulfonate group, sulfinate group, orthoester group, phosphate group, phosphirate group, phosphinate group, phosphonate group, phosphosilicate group, silicate group, hydrazino group, urea bond, thiourea bond, isourea bond, isothiourea bond, thioamide group, sulphonamide group, phosphamide group, phosphoramidite group, pyrophosphamide group, cyclophosphamide group, ifosfamide group, thiophosphamide group, azaacetal group, azacycloacetal group, azathiaacetal group, azahemiacetal group, azaketal group, azacycloketal group, azathiaketal group, and combinations of any one or more thereof and alkylene groups.

1.2.2. Lipid Moieties

In one specific embodiment of the present invention, $B_1$ and $B_2$ are each independently a linking bond or a straight-chain $C_{1-14}$ alkylene group; the $C_{14}$ alkylene group has 0-2 hydrogen atoms replaced by 0-2 $R_q$, and $R_q$ is, at each occurrence, independently —$(CH_2)_{tq}C[(CH_2)_{tq}H]_3$, —$(CH_2)_{tq}O(CH_2)_{tq}H$, —$(CH_2)_{tq}S(CH_2)_{tq}H$, or —$(CH_2)_{tq}N[(CH_2)_{tq}H]_2$, wherein tq is, at each occurrence, independently an integer in the range of 0-4; $R_q$ is preferably, at each occurrence, independently —OH or —$CH_3$;

$B_1$ and $B_2$ are preferably, each independently a linking bond or —$(CH_2)_{1-10}$—, more preferably, each independently selected from the group consisting of a linking bond, —$(CH_2)_2$—, —$(CH_2)_3$—, —$(CH_2)_4$—, —$(CH_2)_5$—, —$(CH_2)_6$—, —$(CH_2)_7$—, and —$(CH_2)_8$—.

In one specific embodiment of the present invention, $R_1$ and $R_2$ each independently contains 0-8 carbon-carbon double bonds and/or 0-8 carbon-carbon triple bonds, and each independently has 0-10 hydrogen atoms replaced by 0-10 $R_m$; $R_m$ is, at each occurrence, independently selected from the group consisting of a straight-chain $C_{1-6}$ alkyl group, a branched $C_{1-6}$ alkyl group, a $C_{3-12}$ cycloalkyl group, a $C_{2-8}$ alkenyl group, a $C_{2-8}$ alkynyl group, a phenyl group, and a benzyl group; $R_m$ is preferably a methyl group;

$R_1$ and $R_2$ are each independently selected from the group consisting of $R_L$, $R_B$, and $R_r$, and preferably, each independently $R_L$ or $R_B$;

wherein, $R_L$ is selected from the group consisting of the following structures, and cis-/trans-isomers thereof:

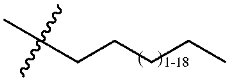

,

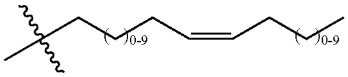

,

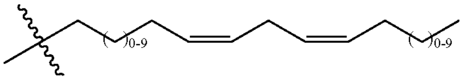

,

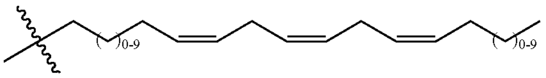

,

-continued

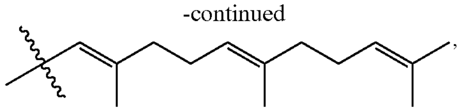

,

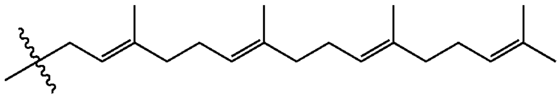

;

$R_L$ is preferably selected from the group consisting of the following structures:

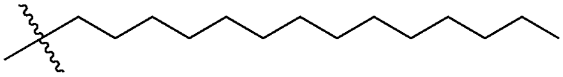

,

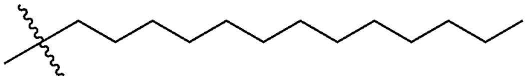

,

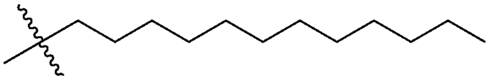

,

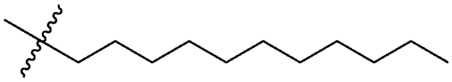

,

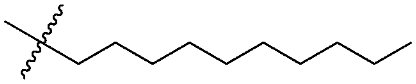

,

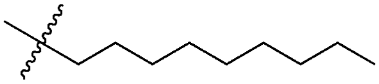

,

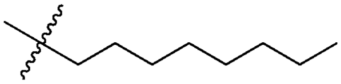

;

wherein, the structure of $R_B$ is

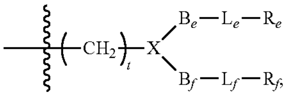

wherein X is CH or N; the t of $R_B$ is an integer in the range of 0-5; $B_e$ and $B_f$ are each independently a linking bond or a $C_{1-10}$ alkylene group; $L_e$ and $L_f$ are each independently a linking bond, —O—, —OC(═O)—, —C(═O)O—, —NHC(═O)—, or —C(═O)NH—; $R_e$ and $R_f$ are each independently a $C_{1-12}$ alkyl group;

$R_B$ is preferably selected from the group consisting of the following structures:

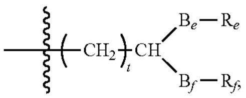

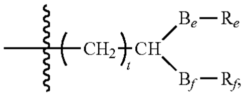

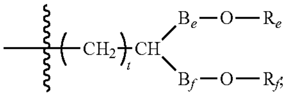

$R_B$ is more preferably selected from the group consisting of the following structures:

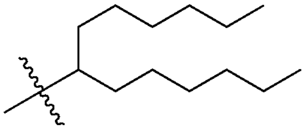

,

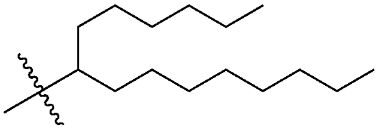

,

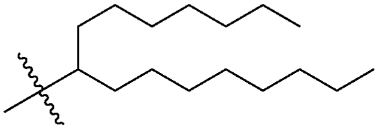

,

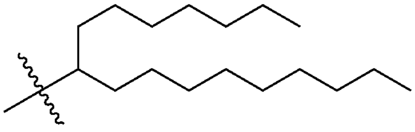

,

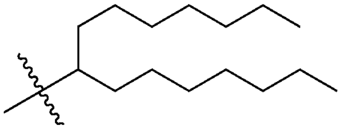

,

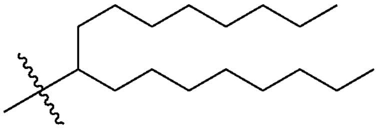

,

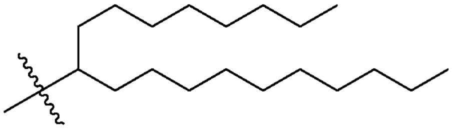

,

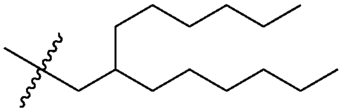

,

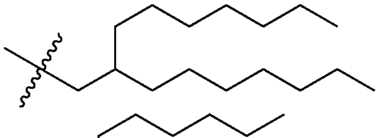

,

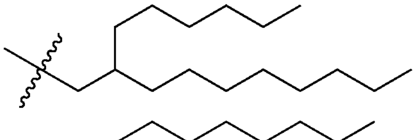

,

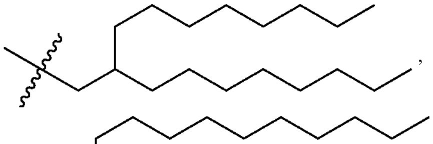

,

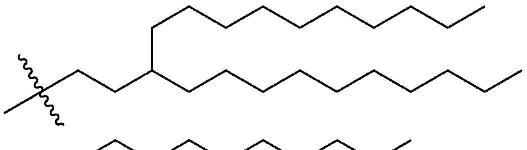

,

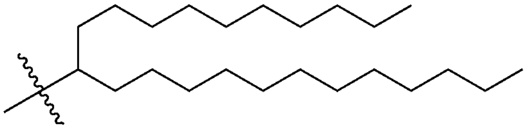

;

wherein, $R_r$ is a ring-containing $C_{4-30}$ alkyl group or $C_{4-30}$ heteroalkyl group, preferably

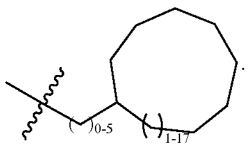

In one specific embodiment of the present invention, $R_L$ is preferably a straight-chain $C_{1-30}$ aliphatic hydrocarbon group containing 0-10 $R_m$, more preferably selected from the group consisting of a straight-chain $C_{1-25}$ alkyl group, a tridec-8-enyl group, a tetradec-9-enyl group, a pentadec-8-enyl group, a hexadec-9-enyl group, a heptadec-5-enyl group, a heptadec-8-enyl group, a heptadec-10-enyl group, a heptadeca-8,11-dienyl group, an octadec-6-enyl group, an octadec-9-enyl group, an octadec-11-enyl group, an octadeca-9,12-dienyl group, an octadeca-9,12,15-trienyl group, an octadeca-8,11,14-trienyl group, a nonadec-10-enyl group, a nonadeca-10,13-dienyl group, an icos-11-enyl group, an icosa-11,14-dienyl group, a 2,6,10-trimethylundeca-1,5,9-trienyl group, a 3,7,11-trimethyldodeca-2,6,10-trienyl group, and a 3,7,11,15-tetramethylhexadeca-2,6,10,14-tetraenyl group.

1.2.3. Polyethylene Glycol Components

In one specific embodiment of the present invention, a nitrogen-branched PEGylated lipid has the structure represented by the general formula (1) or the general formula (2).

In one specific embodiment of the present invention, any two RPEG have identical or different number average molecular weights, and every RPEG are each independently monodisperse or polydisperse.

In one specific embodiment of the present invention, any two RPEG have identical or different degrees of polymerization, and it is preferred that all RPEG have the same degree of polymerization.

In one specific embodiment of the present invention, the number average molecular weight of RPEG is selected from 0.5 kDa-20 kDa, preferably 0.5 kDa-5 kDa, and more preferably 0.5 kDa, 1 kDa, 2 kDa, and 5 kDa.

In one specific embodiment of the present invention, XPEG each independently has a linear structure or a non-linear structure; the non-linear structure is selected from any of the following cases:

Case (1): constructed from any multivalent residue of the following small molecules: a multifunctional small molecule, a multifunctional small molecule containing a heterofunctional group, and an amino-acid small molecule;

Case (2): constructed from any of the following non-linear combinations: a branched structure, a comb structure, a dendritic structure, a dendrimer-like structure, a cyclic structure, a hyperbranched structure, and combinations thereof;

wherein, the multifunctional small molecule is preferably a polyol, a polythiol, a polycarboxylic acid, a primary polyamine, or a secondary polyamine;

wherein, the multifunctional small molecule containing a heterofunctional group is preferably a polyol containing a heterofunctional group, a polythiol containing a heterofunctional group, a polycarboxylic acid containing a heterofunctional group, a primary polyamine containing a heterofunctional group, or a secondary polyamine containing a heterofunctional group;

wherein, the amino-acid small molecule is preferably glycine, alanine, valine, leucine, isoleucine, phenylalanine, tryptophan, tyrosine, aspartic acid, histidine, asparagine, glutamic acid, lysine, glutamine, methionine, arginine, serine, threonine, cysteine, ornithine, or citrulline;

each XPEG preferably contains 2 RPEG, and it is further preferred that the non-linear structure is constructed from any trivalent residue of the following structures: a triol, a tri-thiol, a primary triamine, a secondary triamine, a tricarboxylic acid, a trisulfonate, a triisocyanate, a trifunctional small molecule containing a heterofunctional group, and an amino-acid small molecule.

In one specific embodiment of the present invention, T in the same molecule have the same structure.

In one specific embodiment of the present invention, $L_{01}$ is selected from the group consisting of a linking bond, $-(CH_2)_t-$, $-NH(CH_2)-$, $-NH(CH_2)C(=O)NH(CH_2)_t-$, $-O(CH_2)_t-$, $-NH(CH_2)_tC(=O)O(CH_2)_t-$, $-OC(=O)(CH_2)_t-$, $-OC(=O)O(CH_2)_t-$, $-OC(=O)(CH_2)_tC(=O)-$, and $-(CH_2)_tC(=O)NH(CH_2)-$, and the left end of $L_{01}$ is connected to $R_{01}$, wherein the t of $L_{01}$ is an integer in the range of 1-4 and is preferably 1 or 2.

In one specific embodiment of the present invention, $R_{01}$ a functional group that can interact with bio-related substances, wherein the interaction is selected from the group consisting of covalent bond formation, hydrogen bond formation, fluorescence effect, and targeting effect; $R_{01}$ is selected from the group consisting of reactive groups, modified forms of reactive groups, therapeutically targeting functional groups, and fluorescent functional groups; wherein, the modified forms are selected from the group consisting of the precursors of reactive groups, the active forms to which reactive groups are precursors, the active forms in which reactive groups are substituted, and the inactive forms in which reactive groups are protected; wherein, the precursors of reactive groups refer to the structures which can be transformed into the reactive groups through at least one process among oxidation, reduction, hydration, dehydration, electronic rearrangement, structural rearrangement, salt complexation and decomplexation, ionization, protonation, and deprotonation.

In one specific embodiment of the present invention, the aforementioned $R_{01}$ is selected from the group consisting of the functional groups in the following classes A~I and modified forms thereof:

Class A: active ester group, analogous structure of active ester group; wherein, the active ester group is selected from the group consisting of a succinimidyl active ester group, a p-nitrophenyl active ester group, an o-nitrophenyl active ester group, a 1,3,5-trifluorophenyl active ester group, a 1,3,5-trichlorophenyl active ester group, a 1,3,5-tribromophenyl active ester group, a 1,3,5-triiodophenyl active ester group, a pentafluorophenyl active ester group, an imidazole active ester group, a benzotriazole active ester group, a thiazolidine-2-thione active ester group, a pyrrolidine-2-thione active ester group, a 2-mercaptobenzothiazole active ester group, and a 1-oxo-3-thioxoisoindoline active ester group; and wherein, the analogous structure of active ester group is an active carboxylate group or an active acyl group;

Class B: carboxyl group, protected carboxyl group, sulfonic acid group, sulfonate group, sulfinic acid group, sulfinate group, sulfenic acid group, ester group, thioester group, dithioester group, carbonate group, thiocarbonate group, dithiocarbonate group, trithiocarbonate group, xanthate group, tetrathiodiester group, sulfone group, sulfoxide group, methacryloyl group, hydroxamic acid group, thiohydroxamic acid group, sulfonyl halide group, thiocarboxy group;

Class C: aldehyde group, hydrated aldehyde group, thioaldehyde group, acyl halide group, ketone group, hydrated ketone group, thione group, hydrated thione group, glyoxal group, acetal group, monothioacetal group, dithioacetal group, ketal group, monothioketal group, dithioketal group, hemiacetal group, thiohemiacetal group, hemiketal group, orthoacid group, protected orthoacid group, orthoester group, cyanate group, thiocyanate group, isocyanate group, isothiocyanate group, oxazoline group, isoxazoline group;

Class D: primary amino group, secondary amino group, protected amino group, hydroxylamine group, thiol group, disulfide group, halogen atom, haloacetamide group, ammonium salt, hydrazino group, tetramethylpiperidinyloxy group, dioxapiperidinyloxy group, O-carbonyl hydroxylamine group, amide group, imide group, hydrazide group, sulfonyl hydrazide group, hydrazone group, imine group, enamino group, alkynylamine group, carbamate group, thiocarbamate group, dithiocarbamate group;

Class E: urea group, thiourea group, guanidino group and its protonated form, amidine group and its protonated form, anhydride group, squaric acid group, squarate group, semi-squaric acid group, semi-squarate group, imidazole-1-carboxamide group, imidate group, nitrone group, aldoxime group, ketoxime group;

Class F: maleimide group, furan-protected maleimide group, acrylate group, N-acrylamide group, N-methacrylamide group, methacrylate group, maleamic acid group, 1,2,4-triazoline-3,5-dione group, linear azo compound group, cyclic azo compound group;

Class G: alkenyl group, alkenylhydrocarbon group, cycloalkenyl group, alkynyl group, alkynylhydrocarbon group, protected alkynyl group, cycloalkynl group, linear conjugated diene group, cyclic conjugated diene group, heteroatom-containing cyclic conjugated diene group, epoxy group, 1,2,4,5-tetrazine group, azido group, nitrile oxide group, cyano group, isocyano group, diazo group, diazonium ion, azo oxide group, nitrilimine group, aldimine N-oxide group, tetrazolyl group, 4-acetyl-2-methoxy-5-nitrophenoxy group and its diazotized form, imidazole group, indolyl group; wherein, the cycloalkenyl group is selected from the group consisting of a cyclooctenyl group, a norbornenyl group, a norbornadienyl group, an oxa norbornenyl group, and an oxa norbornadienyl group;

Class H: hydroxyl group, protected hydroxyl group, protected dihydroxyl group, siloxy group, trihydroxysilyl group, protected trihydroxysilyl group; wherein, the hydroxyl group is selected from the group consisting of an alcoholic hydroxyl group, a phenolic hydroxyl group, an enolic hydroxyl group, and a hemiacetal hydroxyl group;

Class I: monosaccharide group, selected from the group consisting of the residues of allose, altrose, arabinose, cladinose, erythrose, erythrulose, fructose, fucitol, fucosamine, fucose, fuculose, galactosamine, galactosaminitol, N-acetyl-galactosamine, galactose, glucosamine, N-acetyl-glucosamine, glucosaminitol, glucose, glucose-6-phosphate, gulose glyceraldehyde, L-glycero-D-manno-heptose, glycerol, glyceraldehyde, dihydroxyacetone, gulose, idose, lyxose, mannosamine, mannose, mannose-6-phosphate, mannoheptulose, allulose, quinolose, quinosamine, rhamnitol, rhamnosamine, rhamnose, ribose, ribulose, deoxyribose, sedoheptulose, sorbose, tagatose, talose, tartaric acid, threose, xylose, xylulose, and functional derivatives thereof, the monosaccharide group is in D-configuration or L-configuration, cyclic or linear, substituted or unsubstituted;

wherein, the protected hydroxyl group is preferably selected from the group consisting of an ether group, a silicon ether group, an ester group, a carbonate group, and a sulfonate group; the protected amino group is preferably selected from the group consisting of a carbamate group, an amide group, an imide group, a N-alkylamine group, a N-arylamine group, an imine group, an enamine group, an imidazole group, a pyrrole group, and an indole group; the protected thiol group is preferably selected from the group consisting of a thioether group, a disulfide group, a silicon sulfide group, and a thioester group; the protected carboxyl group is preferably the carboxyl group protected by a group selected from the group consisting of a methyl group, an ethyl group, a tert-butyl group, and a benzyl group; the protected alkynyl group is preferably the alkynyl group protected by a silyl group; the protected dihydroxyl group preferably has the structure where the protecting group and two oxygen atoms form a five-membered or six-membered cyclic acetal structure; the dihydroxyl protecting group is preferably a methylene or substituted methylene group, and more preferably selected from the group consisting of a methylene group, a 1-methylmethylene group, a 1,1-dimethylmethylene group, a 1,1-cyclopentylene group, a 1,1-cyclohexylene group, a 1-phenylmethylene group, and a 3,4-dimethylphenylmethylene group.

In one specific embodiment of the present invention, the aforementioned $R_{01}$ is selected from the group consisting of the functional groups of the following classes A~I and modified forms thereof:

Class A

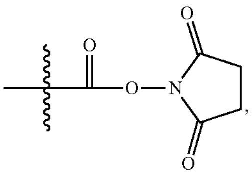
,
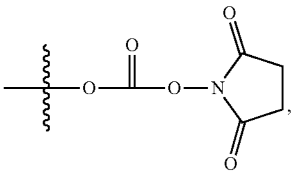
,

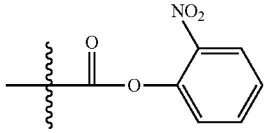
,

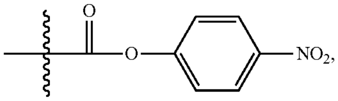
,

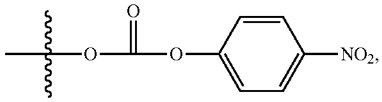
,

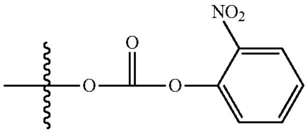
,

-continued
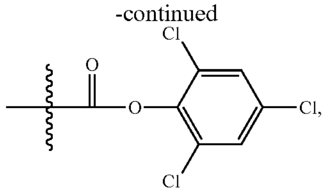
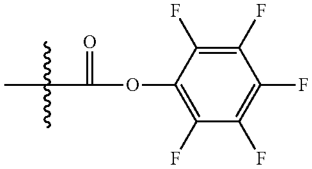
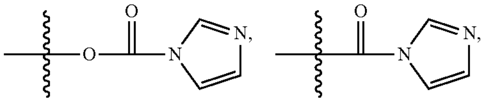
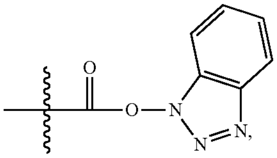
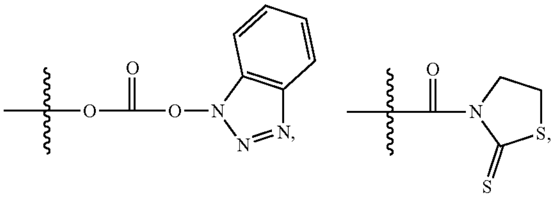
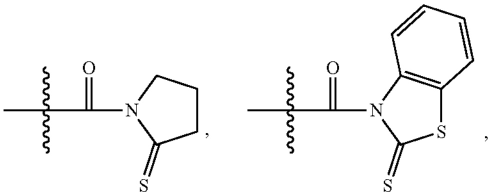
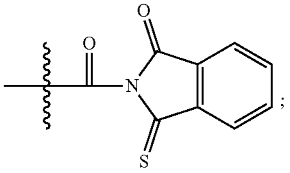
Class B
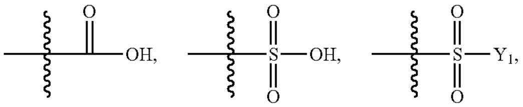
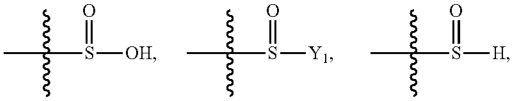
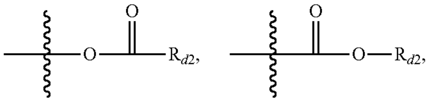
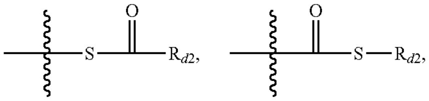
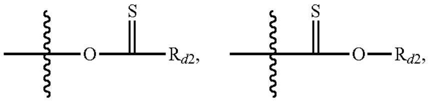
-continued
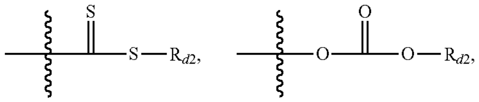
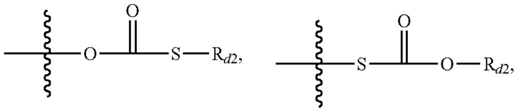
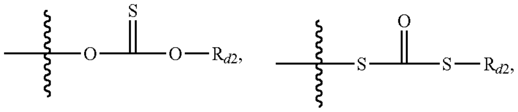
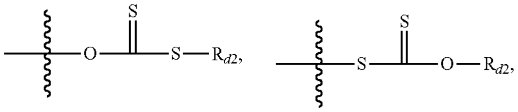
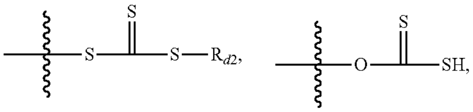
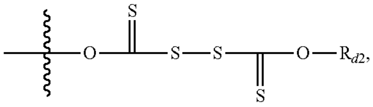
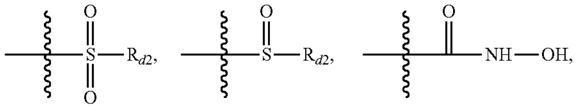
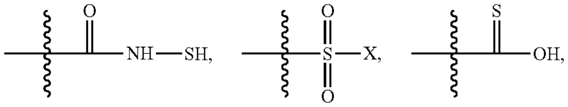
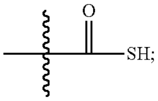
Class C
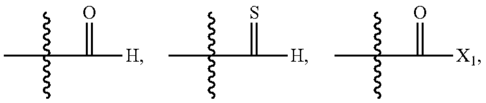
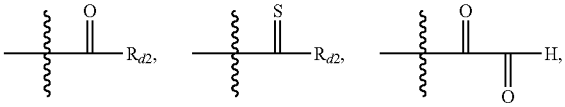
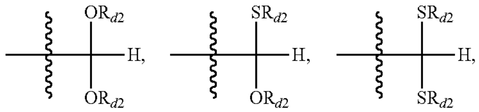
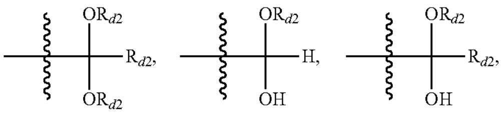
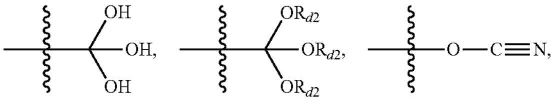
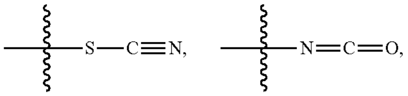

-continued
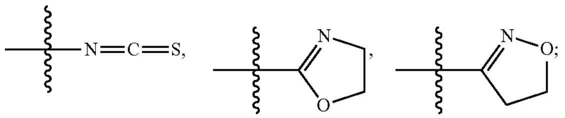
Class D
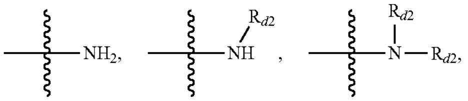
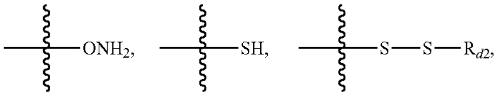
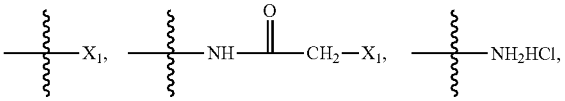
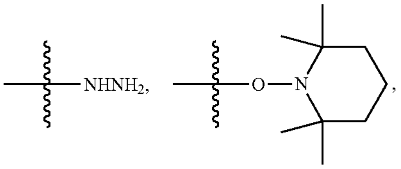
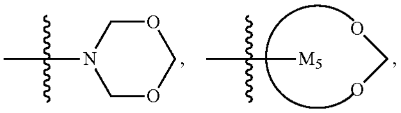
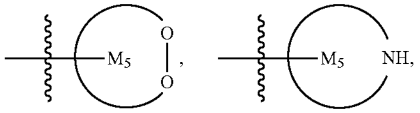
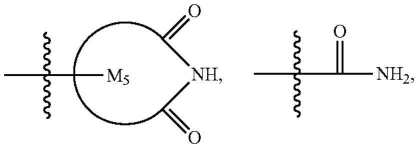
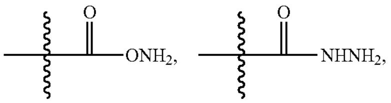
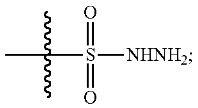
Class E
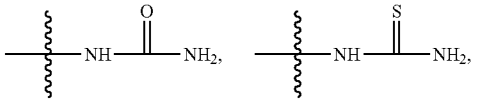
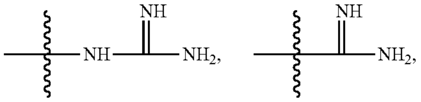
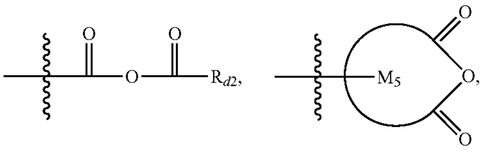
-continued
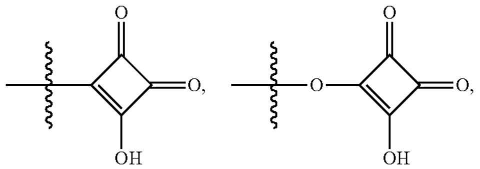
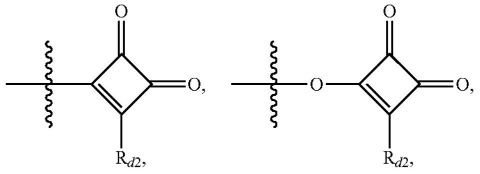
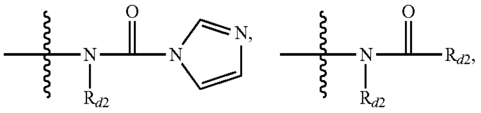
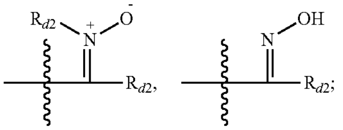
Class F
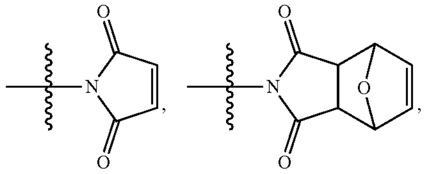
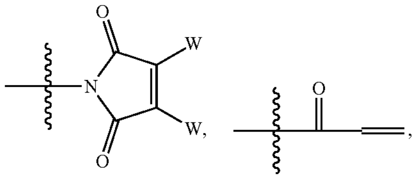
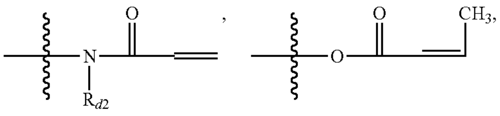
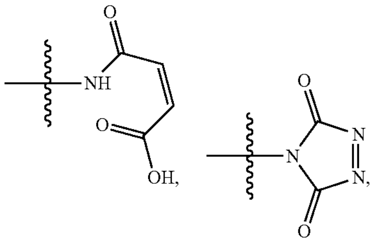
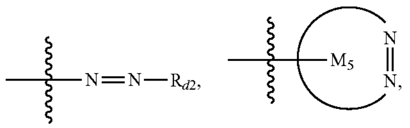
Class G
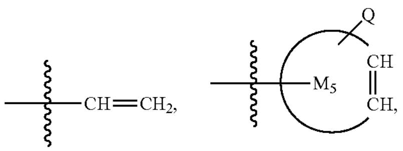

-continued
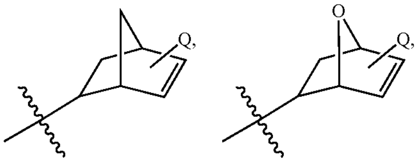
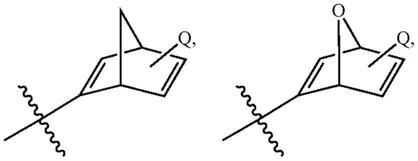
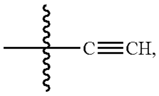
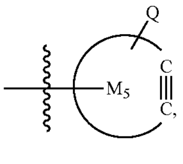
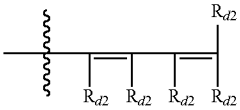
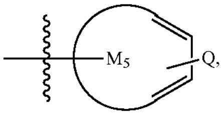
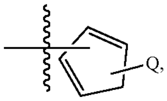
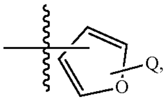
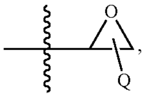
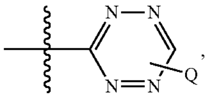
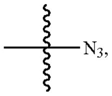
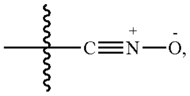
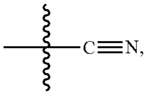
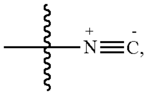
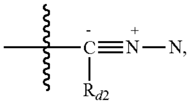
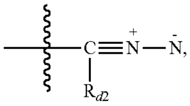
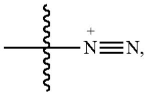
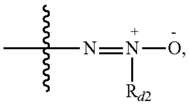
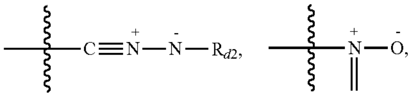
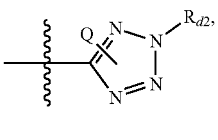
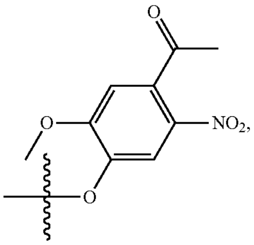
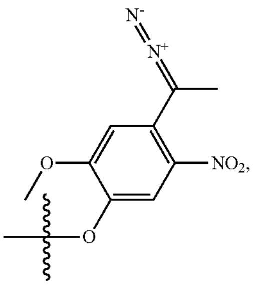
-continued
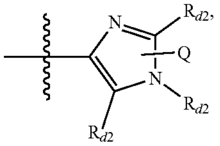
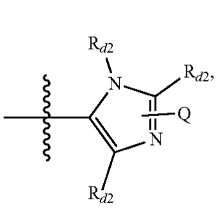
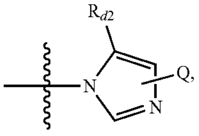
Class H
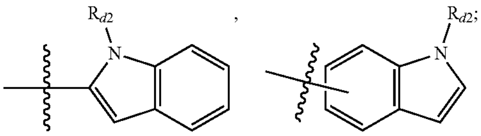
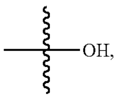
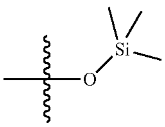
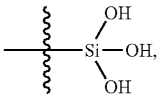
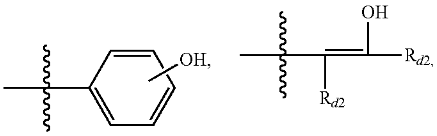
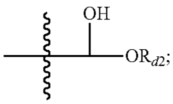
Class I
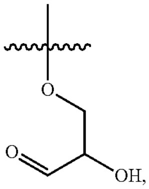
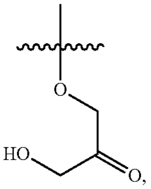
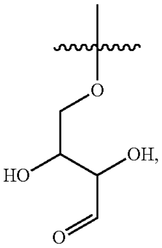
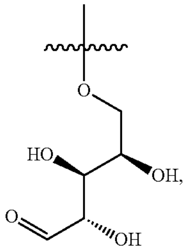
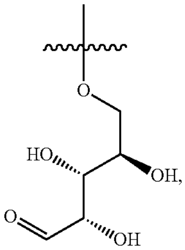
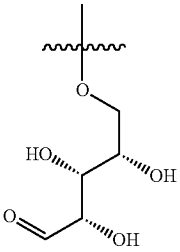
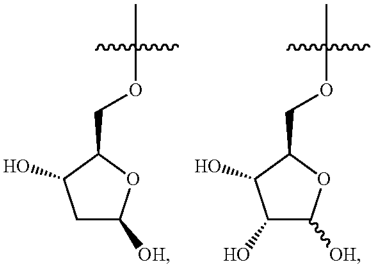

-continued

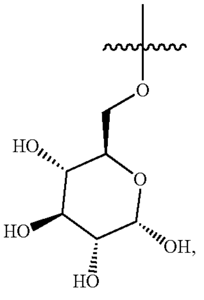

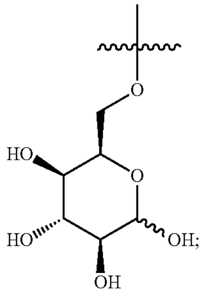

wherein, X is a halogen atom selected from the group consisting of fluorine, chlorine, bromine, and iodine atoms;

wherein, $Y_1$ is selected from the group consisting of $C_{1-5}$ alkyl, vinyl, phenyl, benzyl, p-methylphenyl, 4-(trifluoromethoxy)phenyl, trifluoromethyl, and 2,2,2-trifluoroethyl groups;

wherein, $R_{d2}$ is an organic group and is preferably, at each occurrence, independently selected from the group consisting of $C_{1-5}$ alkyl, $C_{2-5}$ alkenyl, $C_{2-5}$ alkynyl, and phenyl groups, the alkyl, alkenyl, alkynyl and phenyl groups are each independently substituted or unsubstituted;

wherein, W is a leaving group selected from the group consisting of —F, —Cl, —Br, —I, and —SPh;

wherein, $M_5$ is a ring atom selected from the group consisting of a carbon atom, a nitrogen atom, a phosphorus atom, and a silicon atom; the cyclic structure containing $M_5$ is a 3-30 membered ring, preferably a 3-20 membered ring, more preferably a 3-16 membered ring, and more preferably a 5~16 membered ring; the cyclic structure is selected from the group consisting of the following structures, substituted forms thereof, and heterosubstituted forms thereof: cyclohexane, furanose ring, pyranose ring, benzene, tetrahydrofuran, pyrrolidine, thiazolidine, cyclohexene, tetrahydropyran, piperidine, 1,4-dioxane, pyridine, pyridazine, pyrimidine, pyrazine, 1,3,5-triazine, 1,4,7-triazacyclononane, cyclotripeptide, indene, indane, indole, isoindole, purine, naphthalene, dihydroanthracene, xanthene, thioxanthene, dihydrophenanthrene, 10,11-dihydro-5H-dibenzo[a,d]cycloheptane, dibenzocycloheptene, 5-dibenzosuberenone, quinoline, isoquinoline, fluorene, carbazole, iminodibenzyl, acenaphthene, dibenzocyclooctyne, and aza-dibenzocyclooctyne;

wherein,

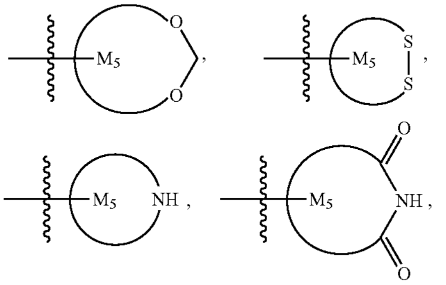

-continued

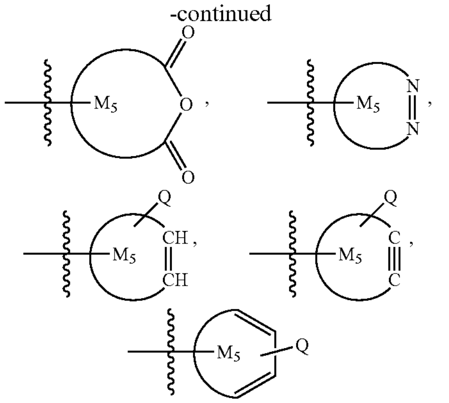

are cyclic structures of which the ring skeletons contain an acetal group, a disulfide bond, an amine group, an imide group, an anhydride group, an azo group, a carbon-carbon double bond, a carbon-carbon triple bond, and a conjugated diene, respectively; the cyclic structure is selected from the group consisting of a carbocycle, a heterocycle, a benzoheterocycle, a substituted carbocycle, a substituted heterocycle, and a substituted benzoheterocycle;

wherein, Q is an atom or substituent that promotes the inductive or conjugate effect of electrons of unsaturated bonds; there can be one or more Q when it is connected to a ring, and when multiple Q are present, the structures of Q are identical or a combination of two or more different structures; when Q is a substituent, the structure of which is linear, branched with a pendant group, or ring-containing;

the modified form is selected from the group consisting of the precursors of reactive groups, the active forms to which reactive groups are precursors, the active forms in which reactive groups are substituted, and the inactive forms in which reactive groups are protected; wherein, the precursors of reactive groups refer to the structures which can be transformed into the reactive groups through at least one process among oxidation, reduction, hydration, dehydration, electronic rearrangement, structural rearrangement, salt complexation and decomplexation, ionization, protonation, and deprotonation.

In one specific embodiment of the present invention, the aforementioned $R_{01}$ is a reactive group selected from the group consisting of a hydroxyl group, a thiol group, an active ester group, an active carbonate group, a sulfonate group, an amino group, a maleimide group, a succinimide group, a carboxyl group, an acyl chloride group, an aldehyde group, an azido group, a cyano group, an alkenyl group, an alkynyl group, an epoxyalkyl group, a rhodamine group, a folate residue, a biotin residue, a monosaccharide group, and a polysaccharide group, or a modified form thereof, the modified form is selected from the group consisting of the precursors of reactive groups, the active forms to which reactive groups are precursors, the active forms in which reactive groups are substituted, and the inactive forms in which reactive groups are protected; wherein, the precursors of reactive groups refer to the structures which can be transformed into the reactive groups through at least one process among oxidation, reduction, hydration, dehydration, electronic rearrangement, structural rearrangement, salt complexation and decomplexation, ionization, protonation, and deprotonation; $R_{01}$ is preferably selected from the group consisting of the following structures:

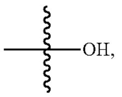, 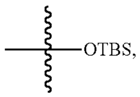, 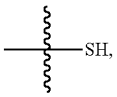, 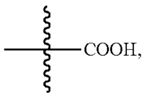, 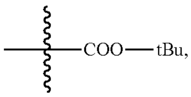, 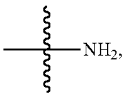, 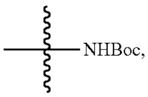,

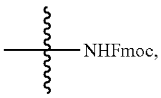, 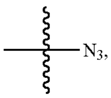, 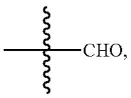, 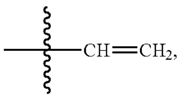, 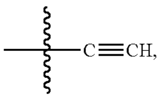, 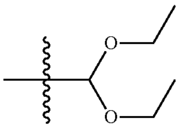, 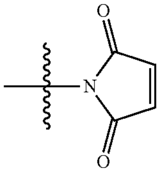,

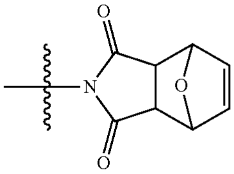, 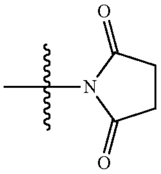, 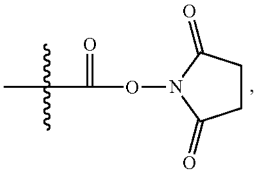, 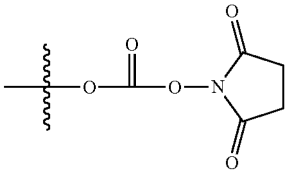,

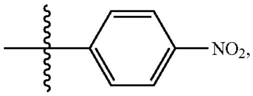, 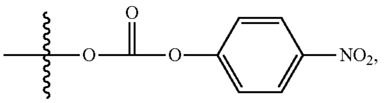, 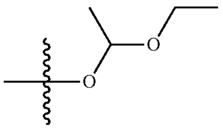,

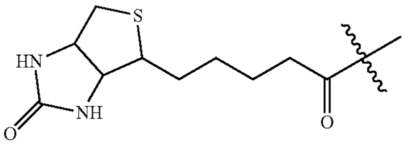,

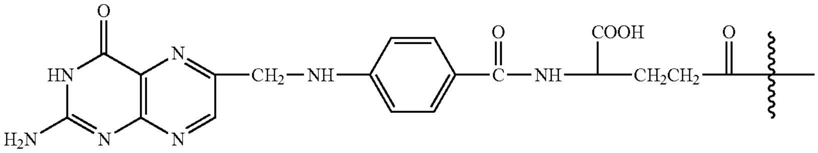.

In one specific embodiment of the present invention, T is a hydrogen atom or a $C_{1-6}$ alkyl group, preferably a methyl group.

1.2.4. $N_{core}$

In one specific embodiment of the present invention, $N_{core}$ is an atomic, branched or cyclic multivalent core structure, and the multivalent atomic core is a trivalent nitrogen atomic core; when $N_{core}$ is the multivalent branched core structure or the multivalent cyclic core structure, it contains at least one trivalent nitrogen atomic core and is preferably selected from any of the following cases:

Case (1): constructed from any multivalent residue of the following small molecules: a multifunctional small molecule, a hetero-multifunctional small molecule, and an amino acid;

Case (2): constructed from any of the following non-linear structures: a branched structure, a comb structure, a dendritic structure, a dendrimer-like structure, a cyclic structure, a hyperbranched structure, and combinations thereof;

wherein, the multifunctional small molecule is preferably a polyol, a polythiol, a polycarboxylic acid, a primary polyamine, or a secondary polyamine;

wherein, the hetero-multifunctional small molecule is preferably a polyol containing a heterofunctional group, a polythiol containing a heterofunctional group, a polycarboxylic acid containing a heterofunctional group, a primary polyamine containing a heterofunctional group, or a secondary polyamine containing a heterofunctional group;

wherein, the amino acid is preferably selected from the group consisting of glycine, alanine, valine, leucine, isoleucine, phenylalanine, tryptophan, tyrosine, aspartic acid, histidine, asparagine, glutamic acid, lysine, glutamine, methionine, arginine, serine, threonine, cysteine, ornithine and citrulline, more preferably aspartic acid, glutamic acid, lysine, ornithine or glycine;

$N_{core}$ is more preferably a residue of amino acid, a residue of dimeric amino acid, or a residue of poly-amino acid; the poly-amino acid contains at least 3 amino acid units; the amino acid units in the dimeric amino acid and those in the poly-amino acid are independent of each other, and any two amino acid units have identical or different structures.

In one specific embodiment of the present invention, y is 2, $N_{core}$ is a trivalent core structure, and $N_{core}$ is preferably any structure in any of the following classes:

Class (1): trivalent nitrogen core structure, specifically as follows:

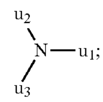;

Class (2): cyclic trivalent core structure containing nitrogen atoms, wherein the cyclic structure is selected from the group consisting of pyrrolidine, piperidine, pyrazine, 1,4,7-triazacyclononane, cyclic tripeptide, indole, isoindole, purine, carbazole, iminodibenzyl, azadibenzocyclooctyne, substituted forms thereof, and hetero-substituted forms thereof; the cyclic structure is preferably any of the following structures:

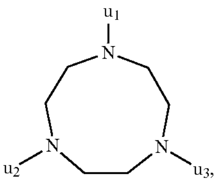

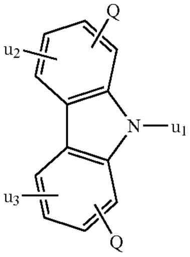

;

Q is a group that modifies the electronic structure, and the number of Q is 0, 1 or greater than 1; when the number of Q is greater than 1, any two Q have identical or different structures;

Class (3): any trivalent residue of the following structures: triol, tri-thiol, primary triamine, secondary triamine, tricarboxylic acid, trisulfonate, triisocyanate, hetero-trifunctional small molecule, and amino acid; the hetero-trifunctional small molecule contains two different types of functional groups, wherein the number of one type is 1 and the number of the other type is 2; wherein, the trivalent residue of amino acid is preferably selected from the group consisting of the following structures:

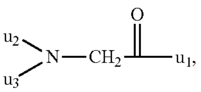
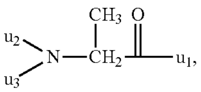

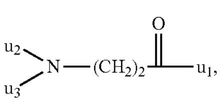
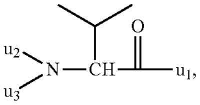

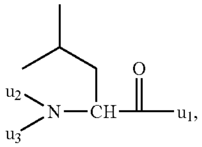
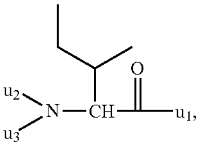

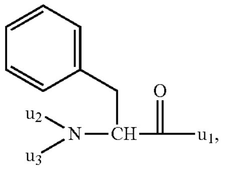
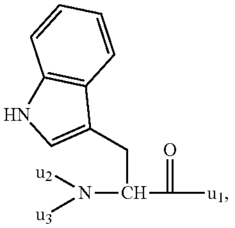

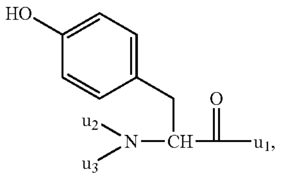
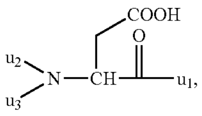

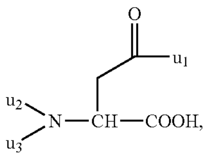
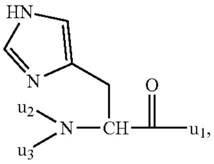

-continued

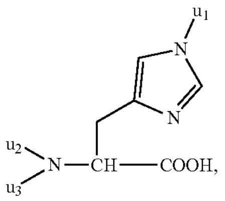
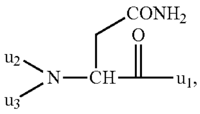

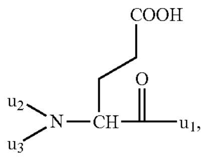
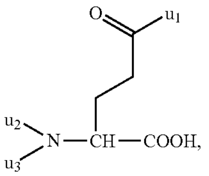

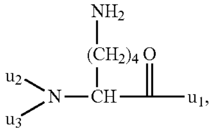
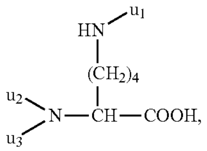

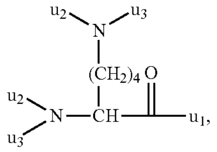
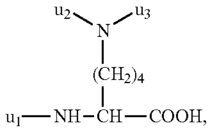

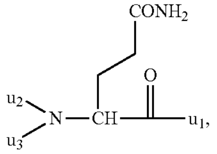
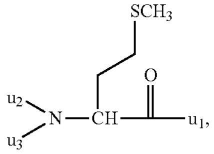

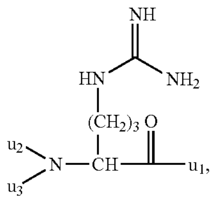
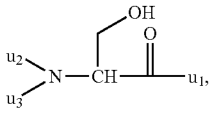

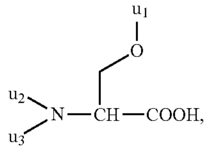
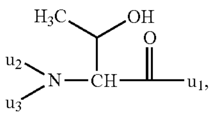

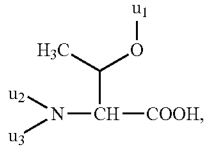
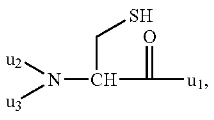

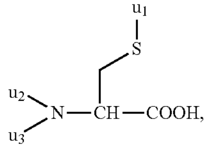
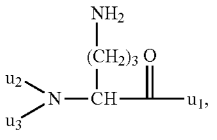

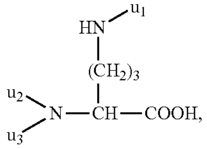
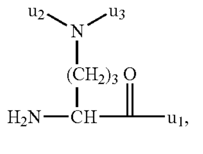

-continued

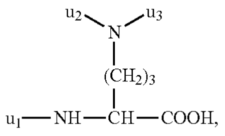

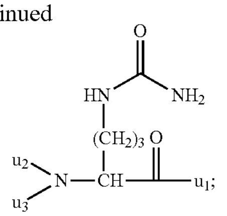

in class (1)~class (3), $u_1$, $u_2$ and $u_3$ are each independently a linking bond connected to $L_d$ or $L_x$, and any two of $u_1$, $u_2$ and $u_3$ are not simultaneously connected to either $L_d$ or any $L_x$.

In one specific embodiment of the present invention, y is 3, and $N_{core}$ contains an atomic, branched or cyclic tetravalent core structure or a combination of two trivalent core structures; $N_{core}$ is preferably selected from the group consisting of the following structures:

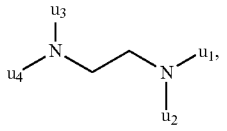

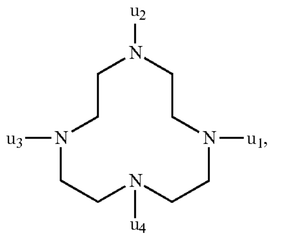

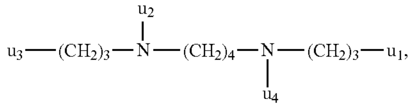

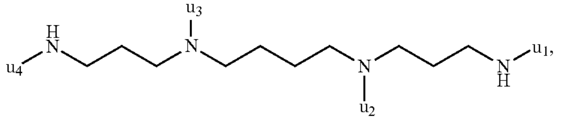

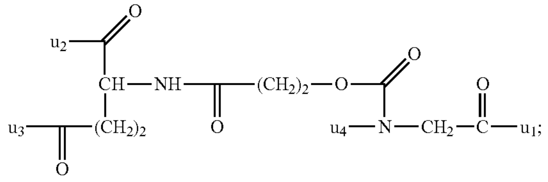

wherein, $u_1$, $u_2$, $u_3$ and $u_4$ are all linking bonds; $u_1$, $u_2$, $u_3$ and $u_4$ are each independently connected to $L_d$ or any $L_x$, and any two of $u_1$, $u_2$, $u_3$ and $u_4$ are not simultaneously connected to either $L_d$ or any $L_x$.

In one specific embodiment of the present invention, y≥4, the valence of $N_{core}$≥5, and $N_{core}$ is selected from the group consisting of a comb structure, a dendritic structure, a branched structure, a hyperbranched structure and a cyclic structure;

the dendritic structure is selected from the group consisting of the following structures:

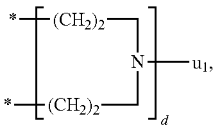

-continued

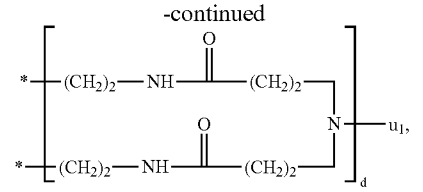

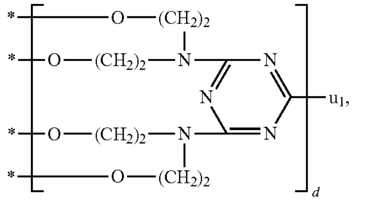

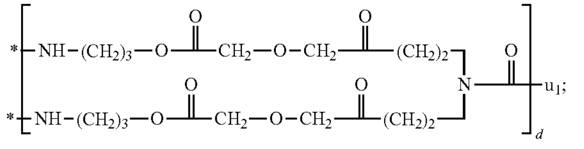

wherein, $u_1$ is a linking bond connected to $L_d$, and the asterisk marker * in the structures represents a linking bond connected to a polyethylene glycol component; d represents the number of generations in the dendritic combination, and d is selected from the group consisting of 2, 3, 4, 5 and 6;

the branched structure, hyperbranched structure or comb structure is selected from the group consisting of a trivalent core structure, a tetravalent core structure, a pentavalent core structure, and combinations thereof, preferably any polymeric residue or its oxidized form of one or more types of amino acids or derivatives thereof;

the cyclic structure is any of the following structures: the residue of a cyclopeptide or derivative thereof, and the skeleton of 1,4,7,10-tetraazacyclododecane.

In one specific embodiment of the present invention, $N_{core}$ is selected from the group consisting of the following structures:

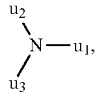

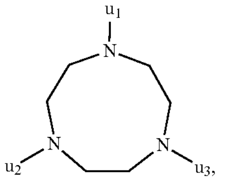

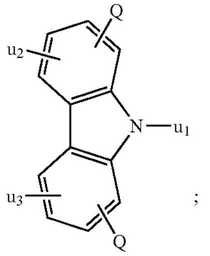

wherein, $u_1$, $u_2$ and $u_3$ are each independently a linking bond connected to $L_d$ or $L_x$, and any two of $u_1$, $u_2$ and $u_3$ are not simultaneously connected to the same $L_d$ or $L_x$;

Q is a group that modifies the electronic structure, and the number of Q is 0, 1 or greater than 1; when the number of Q is greater than 1, any two Q have identical or different structures.

1.2.5. Preparation Methods

In one specific embodiment of the present invention, a PEGylated lipid can be obtained from a preparation process containing coupling reactions and/or polymerization reactions;

the coupling reaction is not particularly limited with respect to the range of options, as long as two identical or different reactive groups can form a covalent linking group through the reaction; a preparation process can contain a single-step or stepwise coupling reaction, and each step of the coupling reaction is preferably, independently selected from the group consisting of alkylation reaction, condensation reaction, amidation reaction, esterification reaction, thioesterification reaction, ring-opening reaction, ring-closing condensation reaction, addition reaction, cycloaddition reaction, addition reaction of α,β-unsaturated bonds, addition reaction of alkynes, Schiff base reaction-reduction reaction, click reaction, azide-alkyne addition reaction, 1,3-dipolar cycloaddition reaction, Diels-Alder addition reaction, thiol-yne reaction, thiol-ene reaction, thiol-vinyl reaction, and condensation reaction. The reaction conditions for the coupling reactions are relevant to the type of the covalent linking groups formed in the reactions, which may include the prior art. The valence state of a covalent linking group obtained from the coupling reactions could be divalent or trivalent, and preferably divalent. Groups obtained from the coupling reactions can be stable groups or degradable groups;

the polymerization reaction includes at least the following two steps: deprotonation of the small molecule initiator, and polymerization of ethylene oxide; the small molecule initiator can be a readily available starting material, or an intermediate in the preparation process;

in the preparation process, when coupling and polymerization reactions both exist, the order in which the coupling and polymerization reactions take place is not limited.

In the present invention, the starting materials used in every preparation methods can be obtained by purchase or synthesis.

In the present invention, with respect to the preparation method of monodisperse PEGylated lipids, the monodisperse starting materials containing polyethylene glycol components can be replaced by polydisperse starting materials containing the same components, therefore obtaining the corresponding polydisperse products; similarly, with respect to the preparation method of polydisperse PEGylated lipids, the polydisperse starting materials containing polyethylene glycol components can be replaced by monodisperse starting materials containing the same components, therefore obtaining the corresponding monodisperse products.

In one specific embodiment of the present invention, polyethylene glycol starting materials including but not limited to linear/non-linear polyethylene glycols and derivatives thereof can be prepared by referring to the methods in CN108530637B, CN110591079A, CN108659227A, CN108530617B, CN1243779C, or CN101029131A.

The intermediates and end-products prepared in the present invention can be purified by a purification method including but not limited to extraction, recrystallization, adsorption treatment, precipitation, reverse precipitation, membrane dialysis, supercritical extraction, etc. Characterization methods including but not limited to NMR, electrophoresis, UV-visible spectrophotometer, FTIR, AFM, GPC, HPLC, MALDI-TOF, circular dichroism spectroscopy, etc., can be used in the characterization and determination of the structure and molecular weight of end-products.

In the present invention, the actual preparation process can also include any necessary procedures such as micro-modification, protection/deprotection, intermediate preparation, workup, purification, etc., which are familiar to a person skilled in the art, mentioned or not in the present invention.

Synthesis of Compounds of the Formula (A-3)

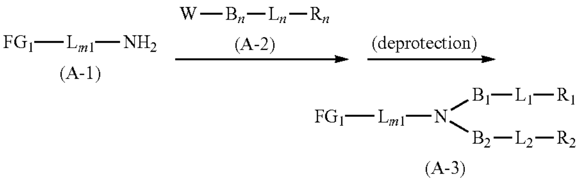

The compound of the formula (A-1) and the compound of the formula (A-2) undergo 1-2 steps of reaction, with optional removal of protecting groups according to the actual situation, to obtain the nitrogen-branched lipid compound of the formula (A-3).

Wherein, n is 1 or 2, and the definitions of $B_1$, $B_2$, $L_1$, $L_2$, $R_1$ and $R_2$ are the same as those for the general formula (1); W is a leaving group and is selected from the group consisting of —Cl, —Br, —I, —OMs, and —OTs; the W in W—$B_1$-$L_1$-$R_1$ and W—$B_2$-$L_2$-$R_2$ are the same or different groups;

$L_{m1}$ is a divalent linking group, selected from the group consisting of a linking bond, an alkylene group, —C(=O)—, —OC(=O)—, —C(=O)O—, —OC(=O)O—, —O—, —S—, —S—S—, —C(=O)S—, —SC(=O)—, —$NR_c$—, —$NR_c$C(=O)—, —C(=O)$NR_c$—, —$NR_c$C(=O)$NR_c$—, —OC(=O)$NR_c$—, —$NR_c$C(=O)O—, —SC(=O)$NR_c$—, —$NR_c$C(=O)S—, and combinations thereof, and the combination preferably contains alkylene groups; the alkylene group is —$(CR_cR_c)_{1-12}$—, preferably —$(CH_2)_{1-12}$—, more preferably —$(CH_2)_{1-4}$—, and most preferably —$CH_2$— or —$(CH_2)_2$—; $R_c$ is, at each occurrence, independently H, a $C_{1-6}$ alkyl group, a carbocyclic group, or a heterocyclic group, preferably H;

$F_{G1}$ is a reactive group or protected form thereof, selected from the group consisting of an amino group, a hydroxyl group, a thiol group, a carboxyl group, a halide group, a sulfonate group, an aldehyde group, an acyl halide group, an activated carboxyl group, an active ester group, and protected forms thereof, preferably selected from the group consisting of —$NH_2$, —NHBoc, —NHFmoc, —NHCbz, —OH, —OTBS, —OMs, and —OTs; the $F_{G1}$ in the formula (A-1) and the formula (A-3) have the same or different structures.

A specific example is the synthesis of S1-3 in Example 1.1:

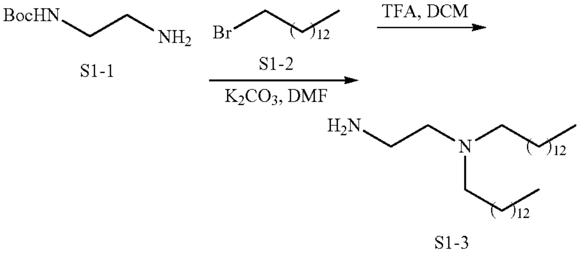

Synthesis of Compounds of the Formula (A-5)

Method 1: same as the aforementioned synthesis method of compounds of the formula (A-3), in this case, $L_{m1}$ and $L_{m2}$ are the same, $F_{G1}$ and $F_{G3}$ are the same, and the structure of the compound of the formula (A-5) corresponds to the formula (A-3).

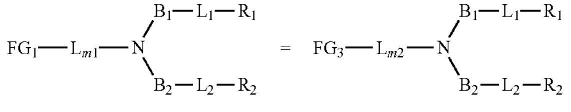

(A-3) (A-5)

Method 2: the compound of the formula (A-3) and the bifunctional small molecule compound of the formula (A-4) undergo one or multiple successive coupling reactions, with optional removal of protecting groups according to the actual situation, to obtain the compound of the formula (A-5):

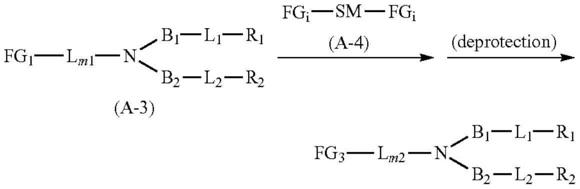

(A-5)

wherein, SM is a residue of small molecule; the definitions of $FG_i$ and $FG_3$ are both the same as that of $FG_1$, and the specific forms are based on the successful implementation of the reaction; when two or more compounds of the formula (A-4) successively participate in the reaction, the structures of SM at every occurrences are the same or different, and the structures of $FG_i$ at every occurrences are the same or different;

wherein, $L_{m2}$ is a divalent linking group, selected from the group consisting of an alkylene group, —C(═O)—, —OC(═O)—, —C(═O)O—, —OC(═O)O—, —O—, —S—, —S—S—, —C(═O)S—, —SC(═O)—, —$NR_c$—, —$NR_c$C(═O)—, —C(═O)$NR_c$—, —$NR_c$C(═O)$NR_c$—, —OC(═O)$NR_c$—, —$NR_c$C(═O)O—, —SC(═O)$NR_c$—, —$NR_c$C(═O)S—, and combinations thereof, and the combination preferably contains alkylene groups; the alkylene group is —$(CR_cR_c)_{1-12}$—, preferably —$(CH_2)_{1-12}$—, more preferably —$(CH_2)_{1-4}$—, and most preferably —$CH_2$— or —$(CH_2)_2$—; $R_c$ is, at each occurrence, independently H, a $C_{1-6}$ alkyl group, a carbocyclic group, or a heterocyclic group, preferably H.

A specific example is the synthesis of S2-5 in Example 2.3:

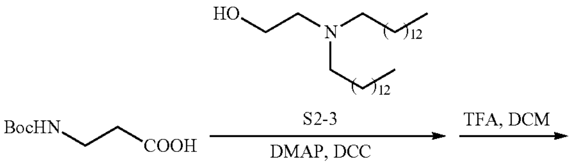

S2-4

-continued

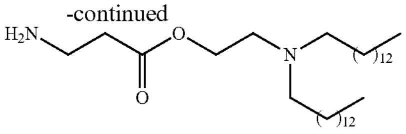

S2-5

Synthesis of Compounds of the Formula (A-7)

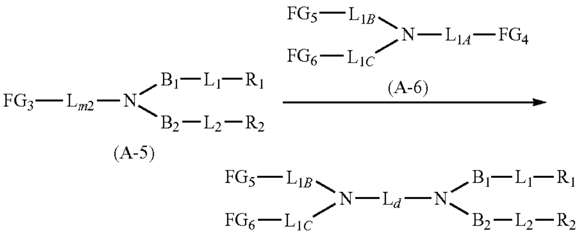

(A-7)

The compound of the formula (A-5) reacts with the trifunctional small molecule compound of the formula (A-6) to obtain the compound of the formula (A-7) containing two reactive groups and at least two nitrogen-branched structures.

Wherein, the definitions of $F_{G4}$, $F_{G5}$, and $F_{G6}$ are all the same as that of $FG_1$, and the specific forms are based on the successful implementation of the reaction; the definitions of $L_{1A}$, $L_{1B}$, and $L_{1A}$ are all the same as that of $L_{m1}$, and any two thereof have identical or different structures; the divalent linking group obtained by the reaction of $F_{G4}$ and $F_{G3}$ forms $L_d$ together with $L_{m2}$ and $L_{1A}$.

A specific example is the synthesis of S3-4 in Example 3.2:

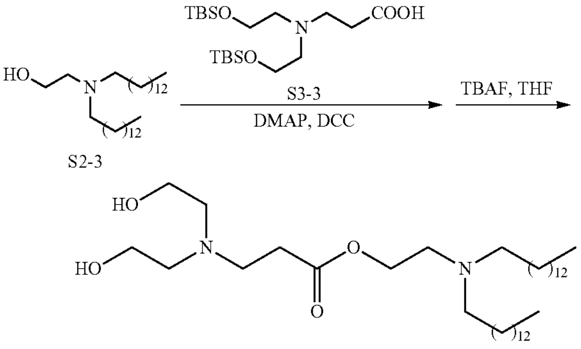

S3-4

Introduction of Polyethylene Glycol Components

Method 1: introducing two polyethylene glycol components on the basis of one amino group:

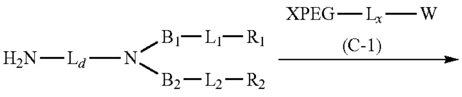

(B-1)

-continued

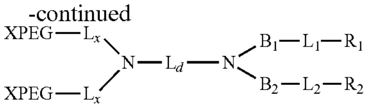

(3)

The compound of the formula (B-1) contains one free amino group and undergoes 1-2 steps of reaction with the compound of the formula (C-1) containing XPEG to obtain the two-arm nitrogen-branched PEGylated lipid compound of the formula (3). Wherein, W is a leaving group and is selected from the group consisting of —Cl, —Br, —I, —OMs, and —OTs.

A specific example is the synthesis of E1-1 in Example 1.1:

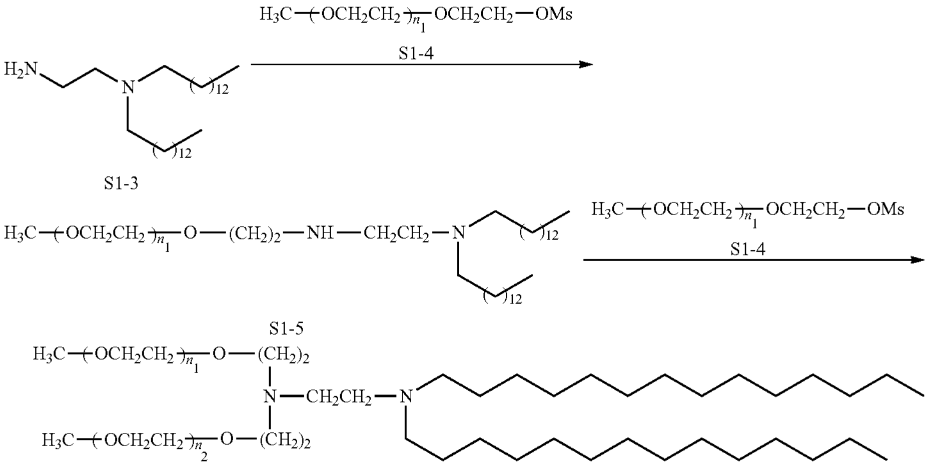

Method 2: introducing two polyethylene glycol components on the basis of two reactive groups:

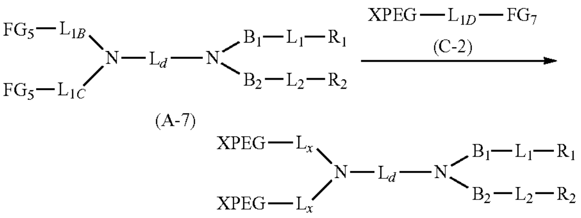

The compound of the formula (A-7) reacts with two identical or different compounds of the formula (C-2) to obtain the two-arm nitrogen-branched PEGylated lipid compound represented by the formula (3). Wherein, $L_{1D}$ and $L_{m1}$ have the same definition; $F_{G1}$ and $F_1$ have the same definition, and the specific forms are based on the successful implementation of the reaction; one $F_{G1}$ reacts with $F_{G5}$ to obtain a divalent linking group that forms an $L_x$ together with $L_{1B}$ and $L_{1D}$, and the other $F_{G1}$ reacts with $F_{G6}$ to obtain a divalent linking group that forms another $L_x$ together with $L_{1C}$ and $L_{1D}$.

A specific example is the synthesis of E3-2 in Example 3.2:

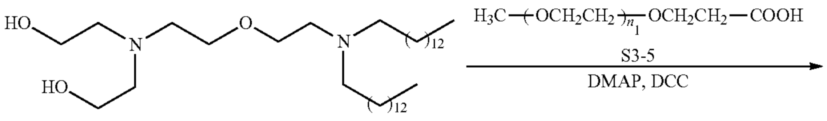

S3-4

-continued

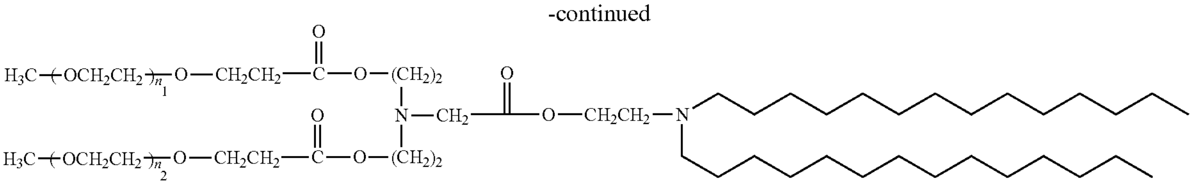

E3-2

Method 3: introducing the nitrogen-branched non-linear polyethylene glycol component in one step:

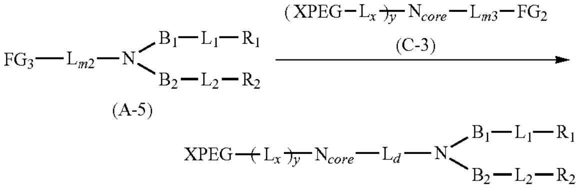

(A-5)

(1)

The compound of the formula (A-5) reacts with the compound of the formula (C-3) to obtain the nitrogen-branched PEGylated lipid compound of the general formula (1).

Wherein, $L_{m3}$ is a divalent linking group, selected from the group consisting of a linking bond, an alkylene group, —C(═O)—, —OC(═O)—, —C(═O)O—, —OC(═O)O—, —O—, —S—, —S—S—, —C(═O)S—, —SC(═O)—, —$NR_c$—, —$NR_c$C(═O)—, —C(═O)$NR_c$—, —$NR_c$C(═O)$NR_c$—, —OC(═O)$NR_c$—, —$NR_c$C(═O)O—, —SC(═O)$NR_c$—, —$NR_c$C(═O)S—, and combinations thereof, and the combination preferably contains alkylene groups; the alkylene group is —$(CR_cR_c)_{1-12}$—, preferably —$(CH_2)_{1-12}$—, more preferably —$(CH_2)_{1-4}$—, and most preferably —$CH_2$— or —$(CH_2)_2$—; $R_c$ is, at each occurrence, independently H, a $C_{1-6}$ alkyl group, a carbocyclic group, or a heterocyclic group, preferably H;

$F_{G2}$ and $F_{G3}$ are both reactive groups, each independently selected from the group consisting of an amino group, a hydroxyl group, a thiol group, a carboxyl group, a halide group, a sulfonate group, an aldehyde group, an acyl halide group, an activated carboxyl group, and an active ester group; the divalent linking group formed by the reaction of $F_{G2}$ and $F_{G3}$ forms $L_d$ together with $L_{m2}$ and $L_{m3}$.

A specific example is the synthesis of E2-1 in Example 2.1:

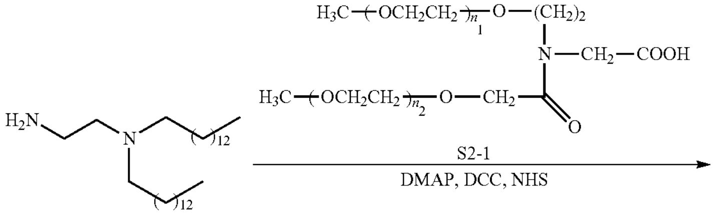

S1-3

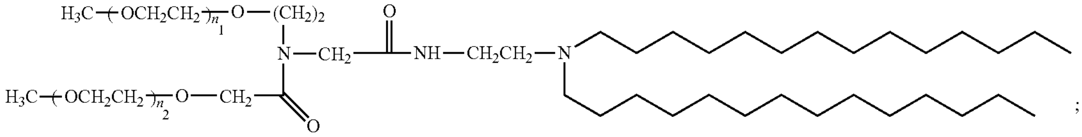

;

E2-1

Another specific example is the synthesis of E2-3 in Example 2.3:

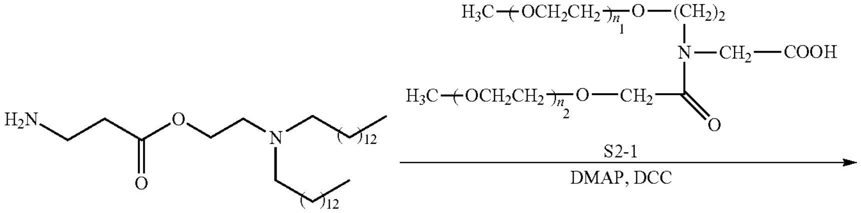

S2-5

-continued

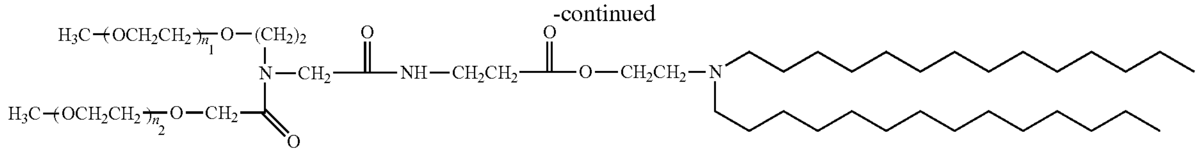

E2-3

End-Functionalization of RPEG

In one specific embodiment of the present invention, the ends of the nitrogen-branched PEGylated lipid contain the functional group $R_{01}$, and $R_{01}$ is preferably introduced by active polyethylene glycol derivatives in an unprotected or protected manner.

In one specific embodiment of the present invention, starting materials include active polyethylene glycol derivatives. The structure of the polyethylene glycol derivative can be any specific structure of monofunctional non-linear polyethylene glycol documented in CN108530637B, CN110591079A, CN108659227A, CN108530617B, and CN1243779C.

In one specific embodiment of the present invention, the end-functionalization can be further applied to a PEGylated lipid of the general formula (1) or the general formula (2), and the obtained structure after the end-functionalization still belongs to the general formula (1) or the general formula (2). The method for the end-functionalization is not particularly limited but is related to the type of the final functional group or its protected form, mainly including the functionalization of the terminal hydroxyl group and the transformation from a reactive group to the target functional group or its protected form.

In the present invention, specific preparation methods of the functionalization of the terminal hydroxyl group include but are not limited to those documented in the paragraphs [0960]-[1205] in CN104530417A.

In the present invention, the transformation from a reactive group to the target functional group or its protected form can be realized by any of the following methods:

Method 1: direct modification. The direct modification based on a reactive group produces the target functional group or its protected form. Examples include the transformation of a carboxyl group into an acyl halide group, a hydrazide group, an ester group, a thioester group, or a dithioester group, the transformations of a hydroxyl group, a thiol group, an alkynyl group, an amino group, a carboxyl group, etc., into the corresponding protected forms, and the modifications of a hydroxyl group, an amino group, etc., with anhydrides.

Method 2: coupling reaction between two reactive groups. A heterofunctional reagent is used as a starting material containing 1 type of reactive group as well as the target functional group, and the reactive group reacts with the terminal reactive group of RPEG to introduce the target functional group or its protected form. The reaction of two reactive groups is not particularly limited with respect to the manner or method, and the reaction conditions are relevant to the type of the divalent linking group formed in the reaction. Prior arts such as alkylation, addition of alkenes, addition of alkynes, Schiff base reaction-reduction reaction, condensation, etc., can be used herein. Wherein, the alkylation reaction is preferably based on thiol group or amino group, corresponding to the formation of thioether bond and secondary or tertiary amino group, respectively. Wherein, the condensation reaction includes but is not limited to those producing ester groups, thioester groups, amide groups, imine bonds, hydrazone bonds, carbamate groups, etc. The target functional group or its protected form can also be introduced via click reactions using starting materials including a heterofunctional reagent containing not only a reactive group selected from the group consisting of an azido group, an alkynyl group, an alkenyl group, a trithioester group, a thiol group, a diene group, a furyl group, a 1,2,4,5-tetrazinyl group, a cyanate group, etc., but also the target functional group or its protected form. The reaction of two reactive groups is accompanied by the formation of new bonds. Typical representatives of newly formed divalent linking groups include amide bond, urethane bond, ester group, secondary amine bond, thioether bond, triazole group, etc.

Method 3: combination of direct modifications and coupling reactions. The target functional group or its protected form can be obtained via the combination.

1.2.6. Specific Exemplary Structures

Structures Containing Two-Arm Polyethylene Glycol Components

In one specific embodiment of the present invention, the nitrogen-branched PEGylated lipid is selected from the group consisting of the following structures:

E1-1

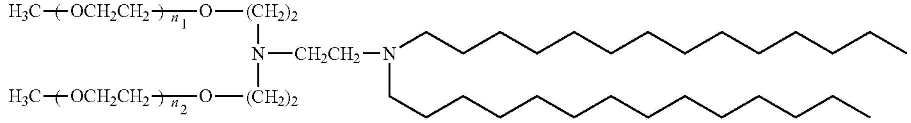

,

-continued
E1-2
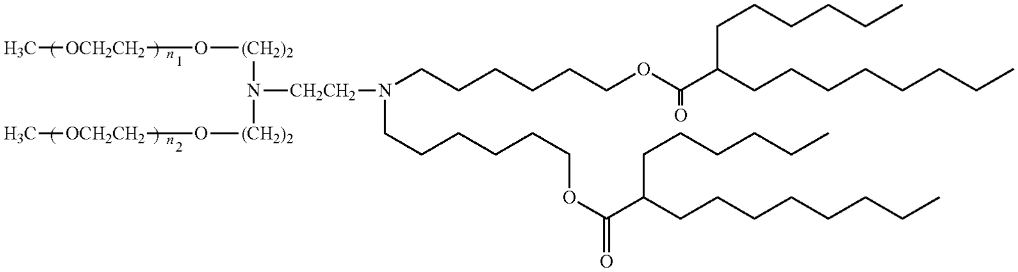
,
E1-3
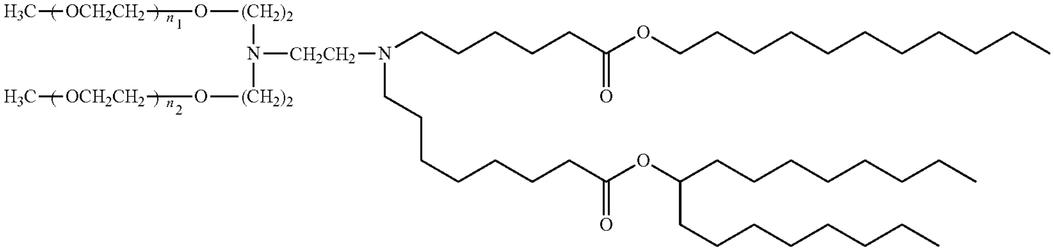
,
E1-4
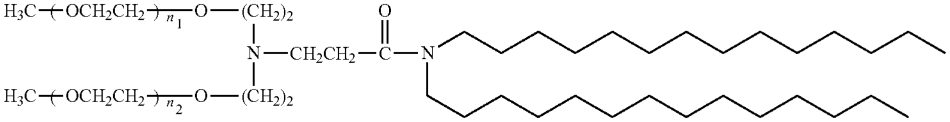
,
E1-5
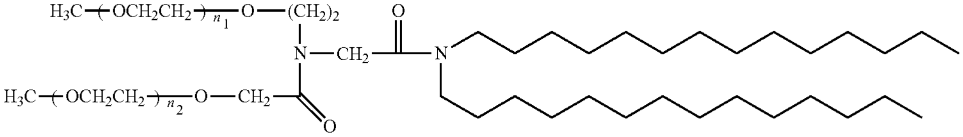
,
E2-1
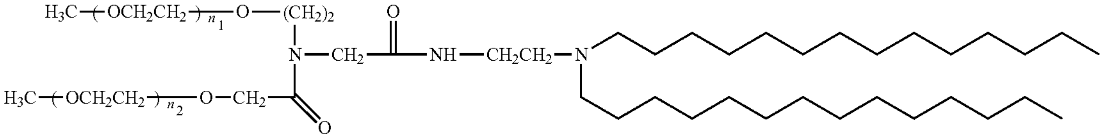
,
E2-2
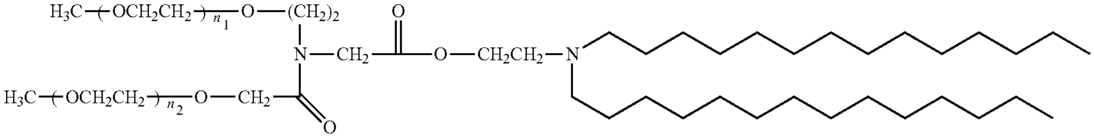
,
E2-3
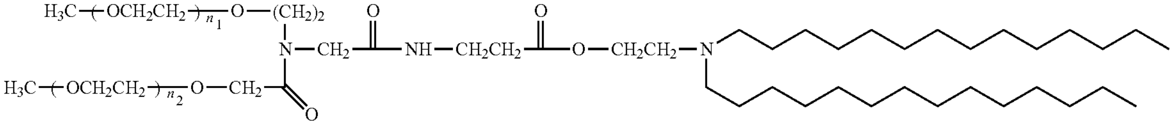
,
E2-4
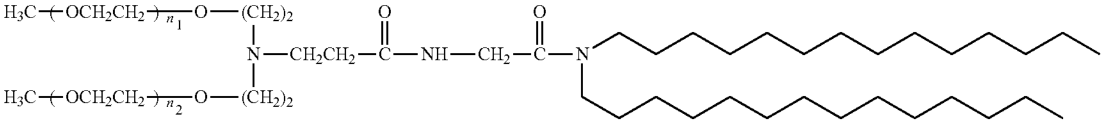
, -continued
E2-5
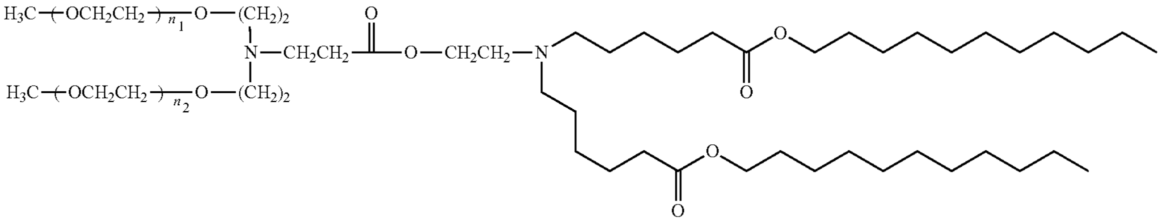
,
E2-6
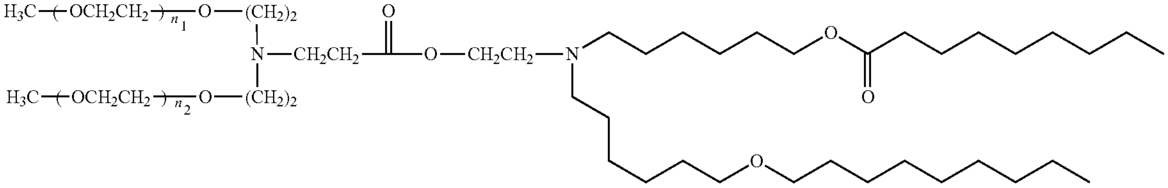
,
E2-7
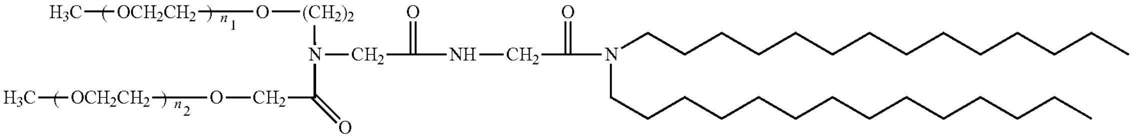
,
E3-1
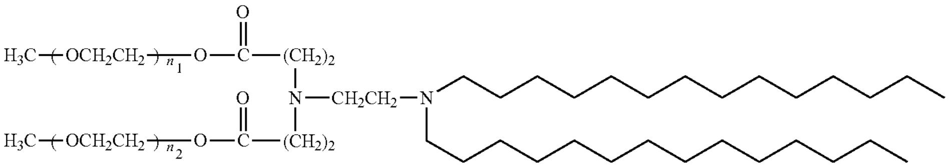
,
E3-2
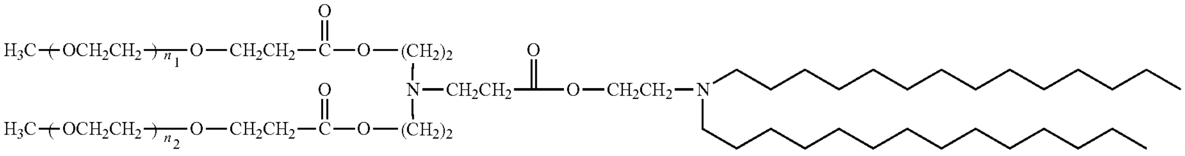
,
E4-1
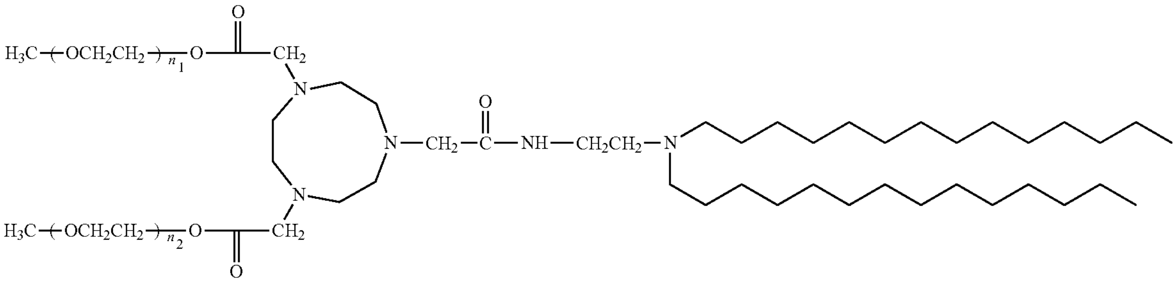
,
E5-1
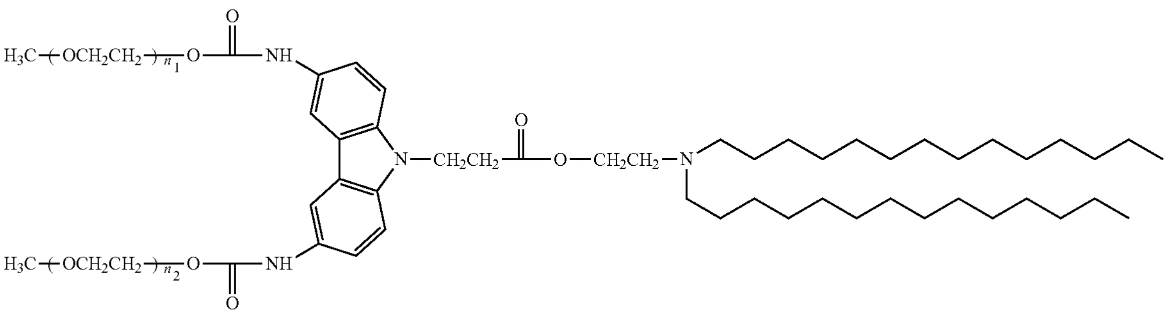
, -continued
E6-1
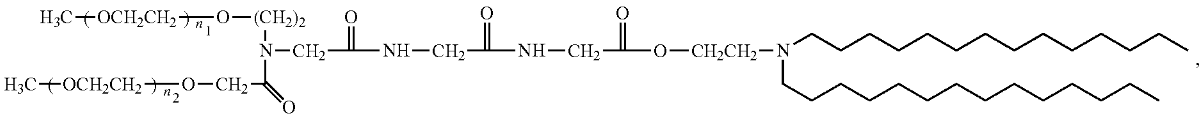
,
E6-2
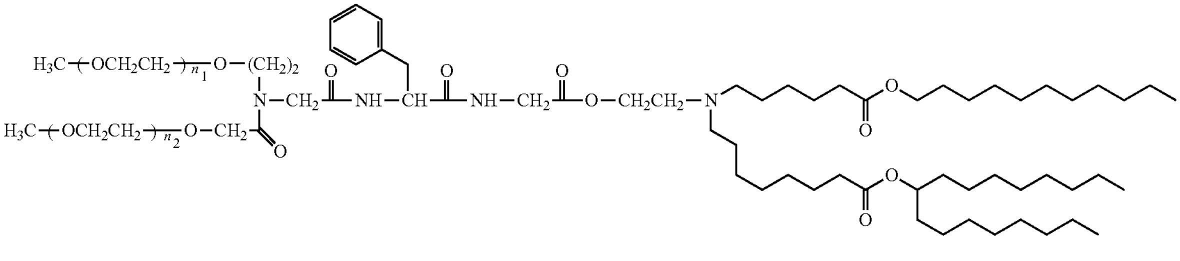
,
E7-1
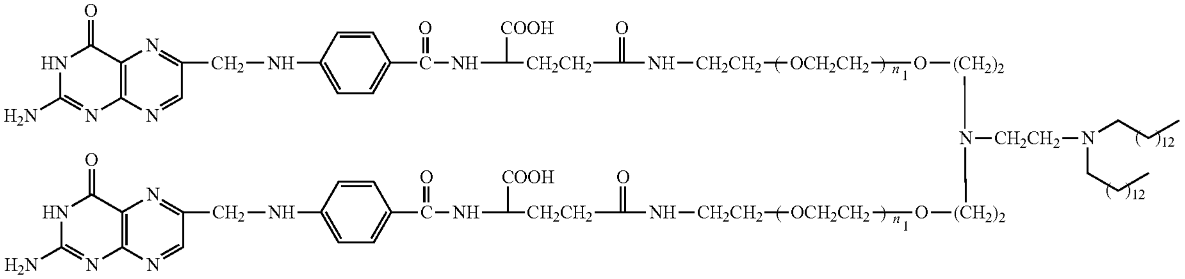
.
Structures Containing Multi-Arm Polyethylene Glycol Components
Exemplary Structure M-1:
M-1
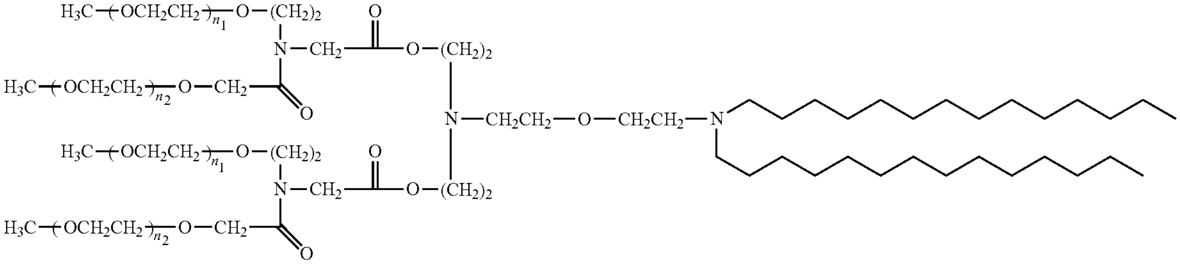
The synthetic route towards M-1 is as follows:
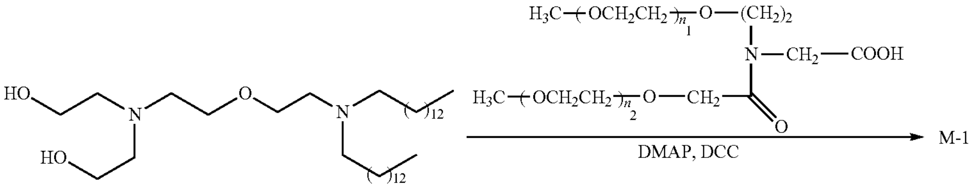

Exemplary Structure M-2:
M-2
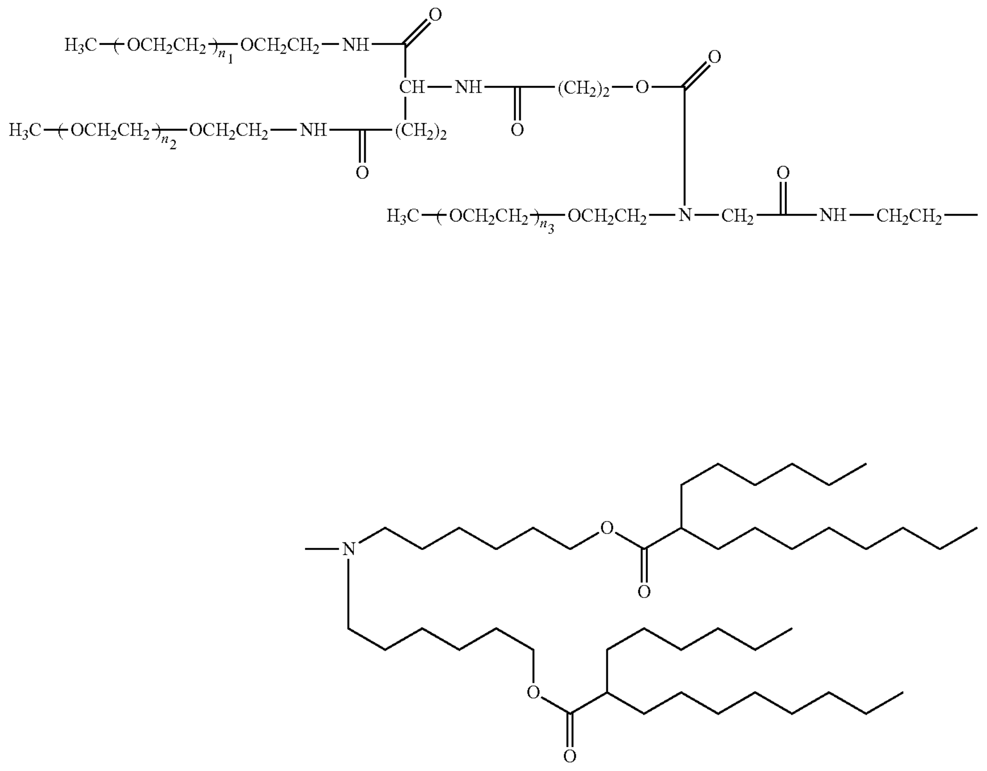
The synthetic route towards M-2 is as follows:

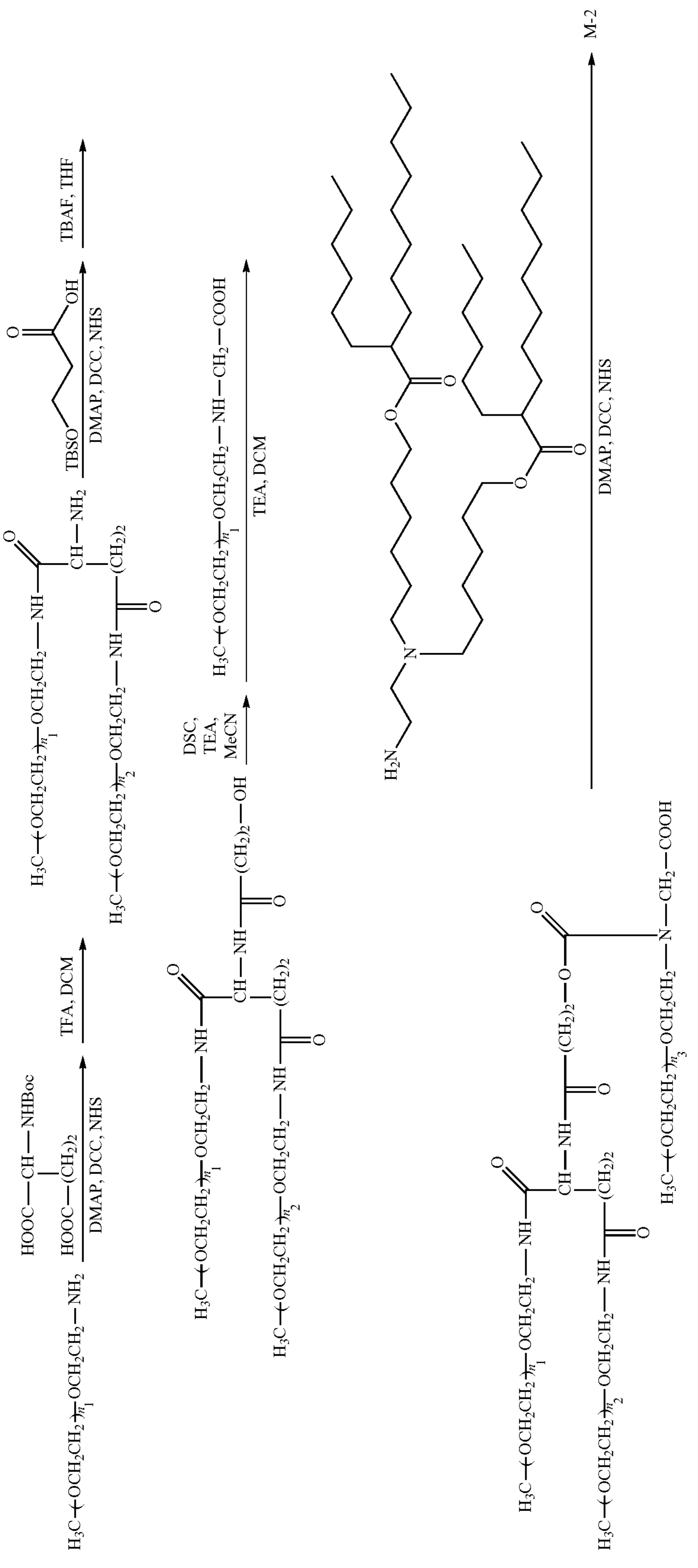
DMAP, DCC, NHS
TFA, DCM
DMAP, DCC, NHS
TBAF, THF
DSC, TEA, MeCN
TEA, DCM
DMAP, DCC, NHS
M-2

Exemplary Structure M-3:

M-3

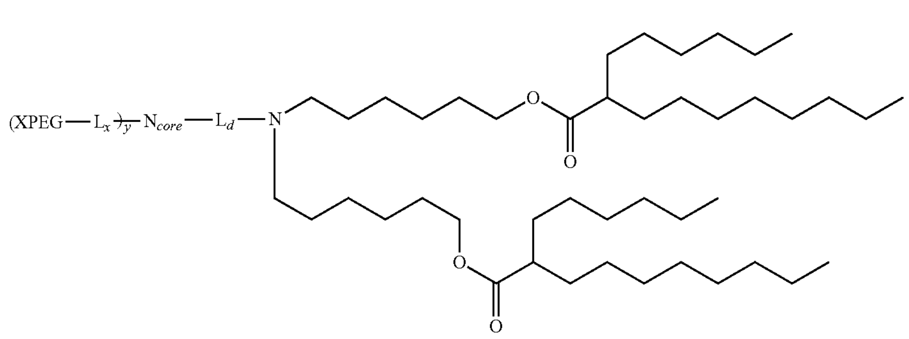

wherein,

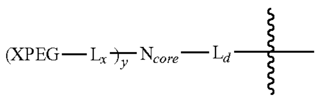

has the following structure:

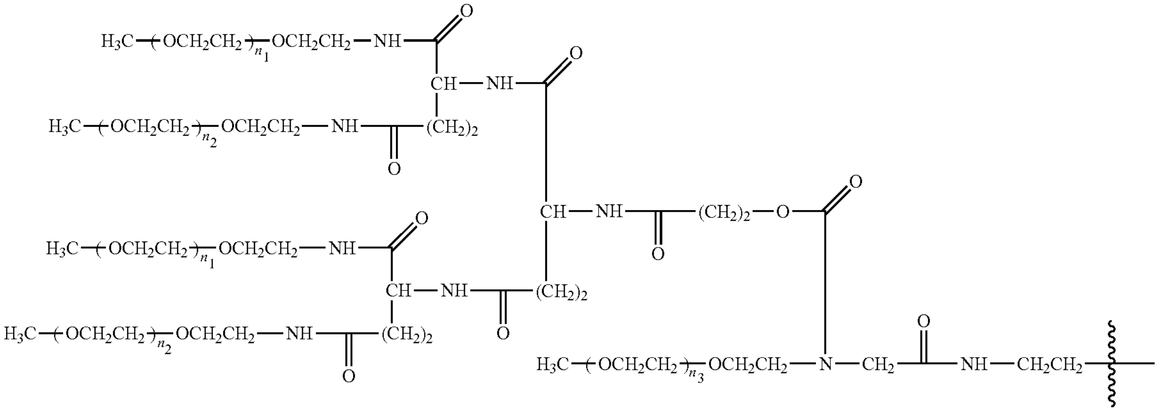

Referring to the synthesis of M-2, the two-arm PEG intermediate can be used to replace the linear PEG as starting material to obtain a four-arm polyethylene glycol amine derivative having the following structure which can be further used, according to the aforementioned method, to obtain the nitrogen-branched PEGylated lipid M-3 containing a five-arm PEG component.

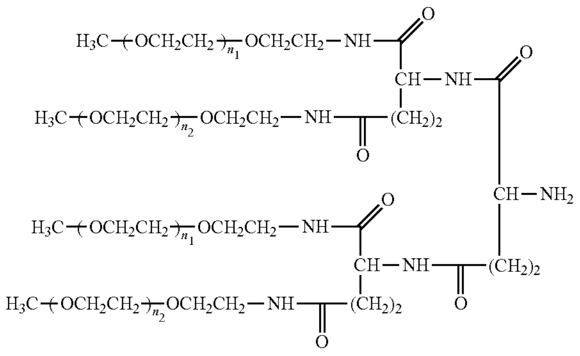

1.3. Lipid Compositions, Lipid Pharmaceutical Compositions and Formulations Thereof, Liposomes, and Lipid Nanoparticles In one embodiment of the present invention, provided herein is a lipid composition containing any aforementioned nitrogen-branched PEGylated lipid.

In one specific embodiment of the present invention, the lipid composition contains another one or more types of lipids selected from the group consisting of phospholipid, steroid lipid, and PEGylated lipid, and belongs to any of the following cases:

Case (1): the lipid composition also contains a phospholipid;

Case (2): the lipid composition also contains a steroid lipid;

Case (3): the lipid composition also contains a PEGylated lipid;

Case (4): the lipid composition also contains a phospholipid and a steroid lipid;

Case (5): the lipid composition also contains a phospholipid and a PEGylated lipid;

Case (6): the lipid composition also contains a steroid lipid and a PEGylated lipid;

Case (7): the lipid composition also contains a phospholipid, a steroid lipid, and a PEGylated lipid;

preferably, the lipid composition contains another three types of lipids including phospholipid, steroid lipid, and PEGylated lipid, simultaneously.

In one specific embodiment of the present invention, the phospholipid contained in the lipid composition is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dioleoylphosphatidylserine (DOPS), dipalmitoylphosphatidylglycerol (DPPG), palmitoyloleoylphosphatidylethanolamine (POPE), distearoylphosphatidylethanolamine (DSPE), dipalmitoylphosphatidylethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoylphosphatidylcholine, lysophosphatidylcholine, lysophosphatidylethanolamine (LPE), and compositions thereof, the phospholipid can be synthetic or naturally sourced.

In one specific embodiment of the present invention, the steroid lipid contained in the lipid composition is selected from the group consisting of cholesterol, coprostanol, sitosterol, ergosterol, campesterol, stigmasterol, brassicasterol tomatidine, ursolic acid, α-tocopherol, and compositions thereof.

In one specific embodiment of the present invention, the cationic lipid contained in the lipid composition is selected from the group consisting of N,N-dioleyl-N,N-dimethylammonium chloride (DODAC), N,N-distearyl-N,N-dimethylammonium bromide (DDAB), N-[1-(2,3-dioleoyloxy)propyl]-N,N,N-trimethylammonium chloride (DOTAP), N-[1-(2,3-dioleyloxy)propyl]-N,N,N-trimethylammonium chloride (DOTMA), N,N-dimethyl-2,3-dioleyloxy-1-(dimethylamino)propane (DODMA), 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), ((4-hydroxybutyl)azanediyl)bis(hexane-6,1-diyl)bis(2-hexyldecanoate) (ALC-0315), heptadecan-9-yl 8-((2-hydroxyethyl)(6-oxo-6-(undecyloxy)hexyl)amino) octanoate (SM102),

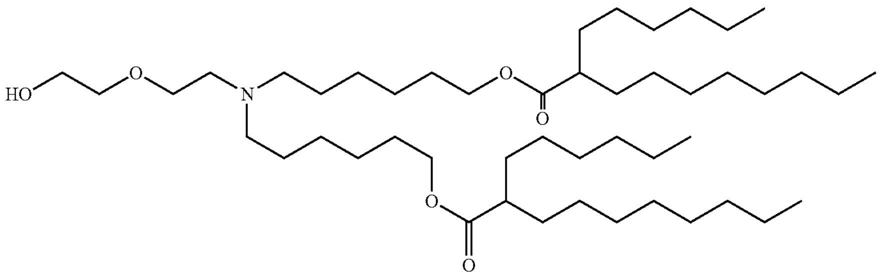

,

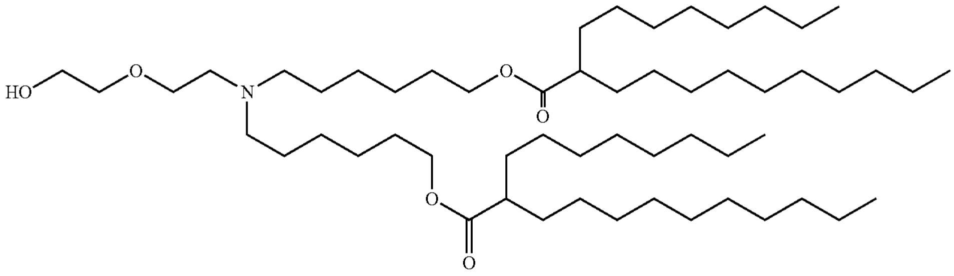

,

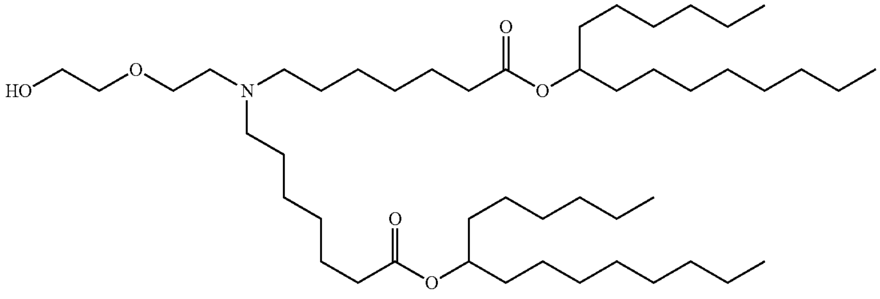

,

-continued
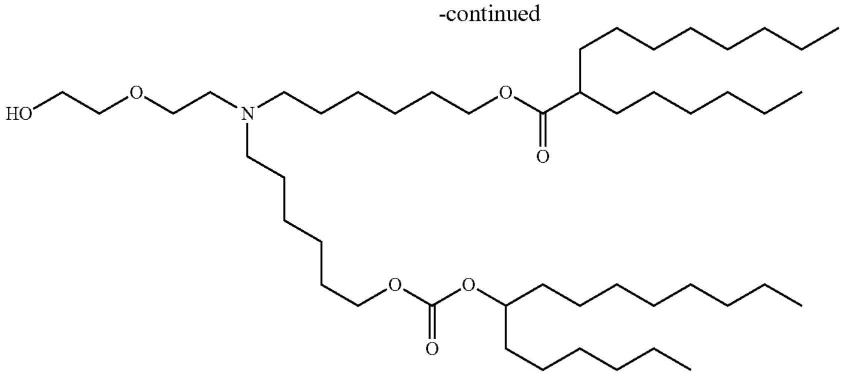
,
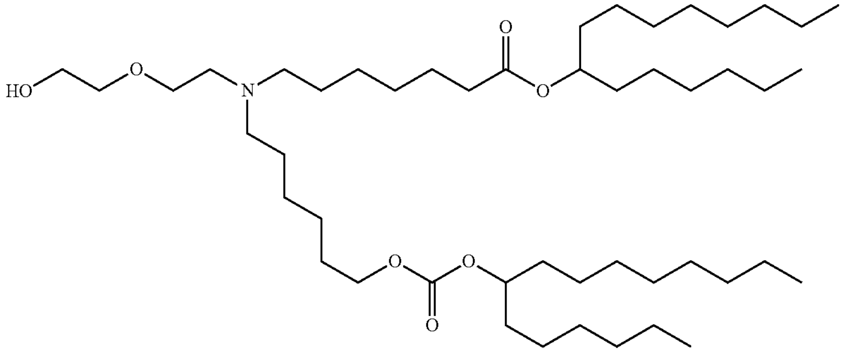
,
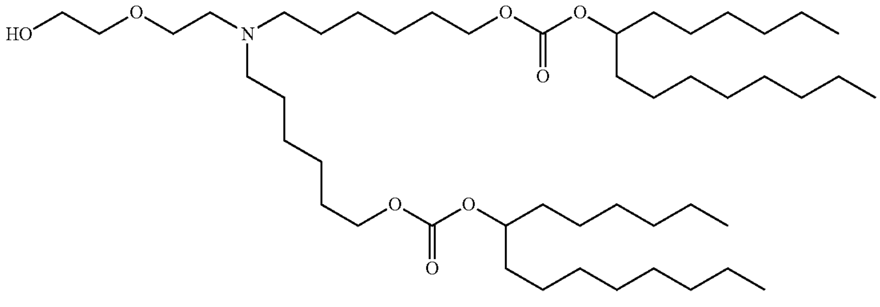
,
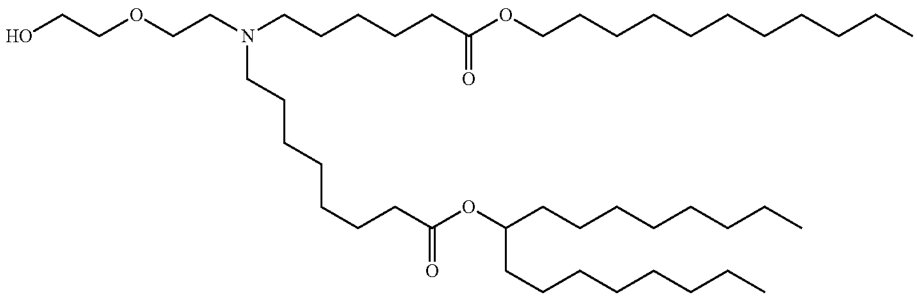
,
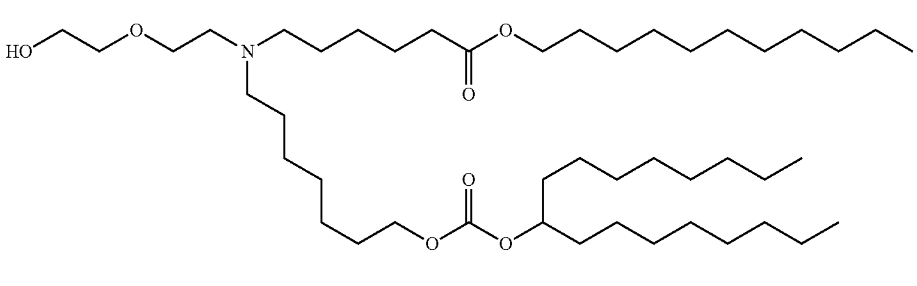
, -continued
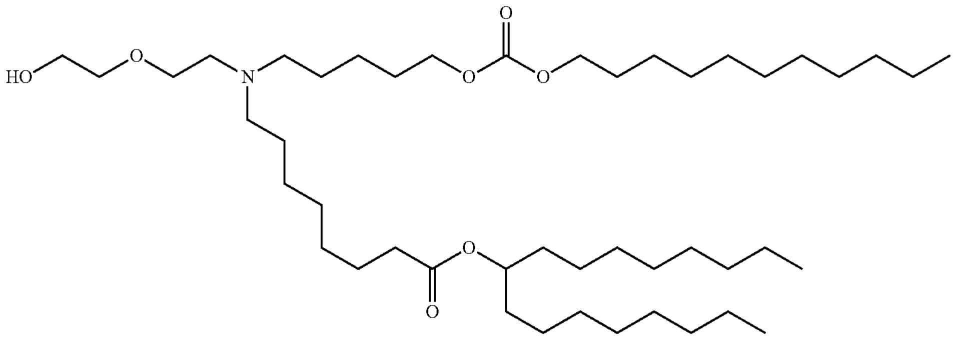
,
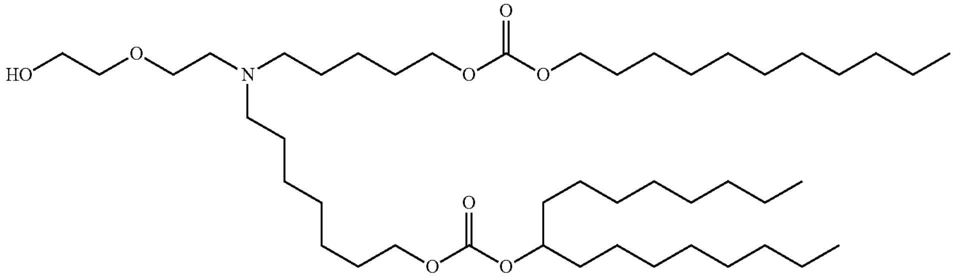
,
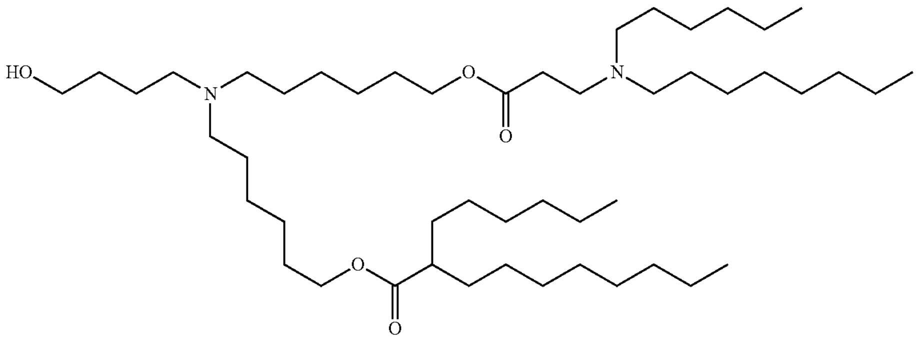
,
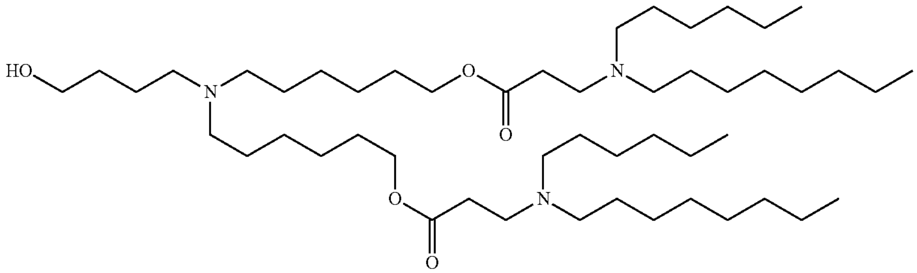
,
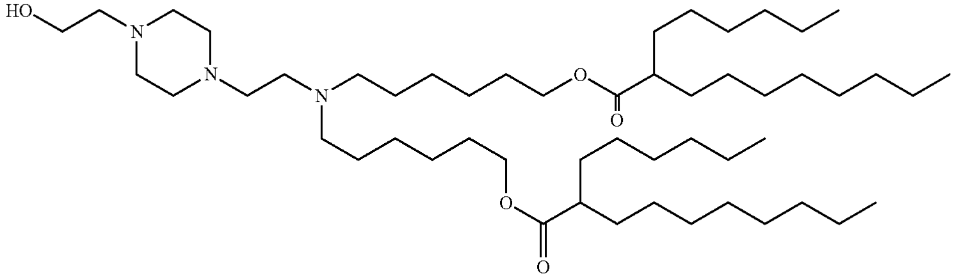
, -continued

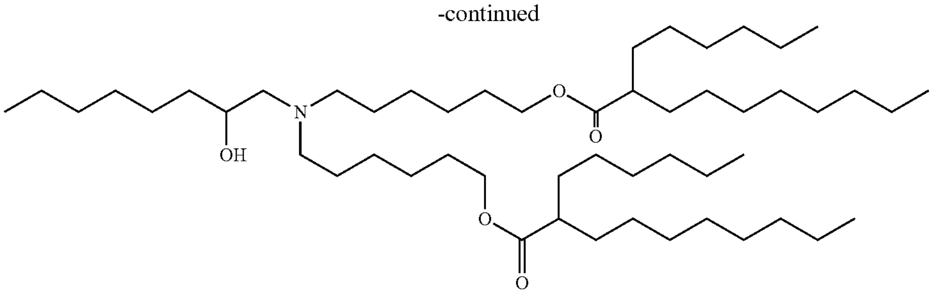

, and compositions thereof.

In a more specific embodiment of the present invention, the molar percentages of PEGylated lipid, cationic lipid, phospholipid, and steroid lipid in total lipids of the lipid composition are not particularly limited; wherein, the molar percentage of PEGylated lipid in total lipids is 0.5-5%, preferably 1-3%, and more preferably 1.5%, 1.6%, 1.7%, 1.8%, or 1.9%;

the molar percentage of cationic lipid in total lipids is 30-65%, preferably 35%, 40%, 45%, 46%, 47%, 48%, 49%, 50%, or 55%;

the molar percentage of phospholipid in total lipids is 7.5-13%, preferably 8%, 9%, 10%, 11%, or 12%;

the molar percentage of steroid lipid in total lipids is 35-50%, preferably 40%, 41%, 42%, 43%, 44%, 45%, 46%, 47%, 48%, 49%, or 50%.

Lipid compositions of the present invention can be used to deliver bioactive substances to one or more of the following physiological sites of a patient: liver or liver cells (such as hepatocytes), kidney or kidney cells, tumor or tumor cells, CNS (central nervous system, such as brain and/or spinal cord) or CNS cells, PNS (peripheral nervous system) or PNS cells, lung or lung cells, blood vessels or blood vessel cells, skin or skin cells (such as dermal cells and/or follicular cells), eye (such as macula, fovea, cornea, retina) or eye cells, ear or ear cells (such as inner ear, middle ear and/or outer ear cells).

In one embodiment of the present invention, provided herein is a lipid pharmaceutical composition containing any aforementioned lipid composition and a drug selected from the group consisting of nucleic acid drug, genetic vaccine, anti-neoplastic drug, small molecule drug, peptide drug, and protein drug.

In one specific embodiment of the present invention, the drug contained in the lipid pharmaceutical composition is a nucleic acid drug selected from the group consisting of DNA, RNA, antisense nucleic acid, plasmid, interfering nucleic acid, aptamer, antagomir, and ribozyme, wherein the RNA is selected from the group consisting of mRNA, saRNA, circRNA, miRNA, and siRNA; the nucleic acid drug is preferably selected from the group consisting of DNA, mRNA, miRNA, and siRNA.

In one specific embodiment of the present invention, the drug contained in the lipid pharmaceutical composition includes but is not limited to doxorubicin, mitoxantrone, camptothecin, cisplatin, bleomycin, cyclophosphamide, streptozotocin, actinomycin D, vincristine, vinblastine, cytosine arabinoside, anthracycline, nitrogen mustard, tioteppa, chlorambucil, rachelmycin, melphalan, carmustine, romustine, busulfan, dibromannitol, mitomycin C, cis-diamminplatinum(II) dichloride, methotrexate, 6-mercaptopurine, 6-thioguanine, cytosine arabinoside, 5-fluorouracil dacarbazine, dibucaine, chlorpromazine, propranolol, demorol, labetalol, clonidine, hydralazine, imipramine, amitriptyline, doxepin, phenytoin, diphenhydramine, chlorpheniramine, promethazine, gentamicin, ciprofloxacin, cefoxitin, miconazole, terconazole, econazole, isoconazole, butoconazole, clotrimazole, itraconazole, nystatin, naftifine, amphotericin B, antiparasitic agents, hormones, hormone antagonists, immunomodulators, neurotransmitter antagonists, glaucoma drugs, vitamins, tranquilizers, imaging agents, taxol, cytochalasin B, gramicidin D, ethidium bromide, emetine, mitomycin, etoposide, teniposide, colchicine, daunorubicin, quinizarin, mithramycin, 1-dihydrotestosterone, glucocorticoid, procaine, tetracaine, lidocaine, puromycin, maytansinoid, and oxaliplatin.

In one specific embodiment of the present invention, the drug contained in the lipid pharmaceutical composition is a nucleic acid drug; the N/P ratio with respect to the cationic lipid and nucleic acid in the composition is preferably (0.1~100):1, more preferably (0.2~30):1, and most preferably (0.5~20):1.

In one specific embodiment of the present invention, the lipid pharmaceutical composition is used as a medicine selected from the group consisting of drugs for treating cancer, anti-infective agents, antibiotic agents, antiviral agents, antifungal agents, and vaccines.

In one specific embodiment of the present invention, the lipid pharmaceutical composition is an LNP-pharmaceutical composition, an LPP-pharmaceutical composition, or a PNP-pharmaceutical composition, preferably an LNP-pharmaceutical composition, more preferably an LNP-nucleic acid pharmaceutical composition, and more preferably an LNP-mRNA composition.

In the present invention, a lipid pharmaceutical composition can form different structures; wherein, the "LNP-pharmaceutical composition" forms the structure of a lipid nanoparticle (LNP), the "LPP-pharmaceutical composition" forms the structure of a lipopolyplex (LPP), and the "PNP-pharmaceutical composition" forms the structure of a polypeptide nanoparticle (PNP); wherein, the "LNP-nucleic acid pharmaceutical composition" forms the structure of a lipid nanoparticle, and the drug contained is a nucleic acid drug; wherein, the "LNP-mRNA composition" is a kind of LNP-nucleic acid pharmaceutical composition, and the nucleic acid drug contained is mRNA.

In one embodiment of the present invention:

provided herein is a liposome or lipid nanoparticle containing any aforementioned lipid composition.

In one embodiment of the present invention, provided herein is a formulation of lipid pharmaceutical composition containing any aforementioned lipid pharmaceutical composition and a working solution, and the working solution is a pharmaceutically acceptable diluent or excipient; the diluent or excipient is preferably deionized water, ultrapure water, phosphate buffer, or physiological saline, more preferably phosphate buffer or physiological saline, and most preferably physiological saline; wherein, the ratio of lipid composition to working solution is preferably (0.05~20) g:100 mL, more preferably (0.1~10) g:100 mL, and most preferably (0.2~5) g:100 mL.

In one specific embodiment of the present invention, the preparation of the formulation of lipid pharmaceutical composition includes the following steps:

(1) equilibrate the lipid components in the diluent or excipient;

(2) add the drug to the mixture containing the equilibrated liposome or lipid nanoparticle and the diluent or excipient, for complexation;

wherein, the equilibration time is preferably 0.1~12 h, more preferably 0.2~6 h, and more preferably 0.5~3 h; the complexation time is preferably 0.1~12 h, more preferably 0.2~5 h, and more preferably 0.5~2 h.

In one specific embodiment of the present invention, the preparation of the LNP-nucleic acid pharmaceutical composition includes the following steps:

(1) dissolve the lipid components with an organic solvent to obtain an organic phase solution;

(2) add the nucleic acid drug to a buffer solution to obtain an aqueous phase solution;

(3) mix the organic phase solution with the aqueous phase solution to obtain the LNP-nucleic acid pharmaceutical composition, wash the mixture using ultrafiltration to remove the organic solvent and free molecules, and finally perform a filtration using a sterile filter for further use;

wherein, the organic solvent is preferably selected from the group consisting of methanol, ethanol, propanol, tert-butanol, acetonitrile, dimethyl sulfoxide, N,N-dimethylformamide, N,N-dimethylacetamide, N-methylpyrrolidone, and mixtures thereof; the buffer solution is preferably a citrate buffer which further preferably has the concentration of 5-80 mM and the pH of 2-6, more preferably the concentration of 10-50 mM and the pH of 3-5; the volumetric ratio of organic phase solution to aqueous phase solution is preferably 1:1-10, more preferably 1:2 or 1:3.

In one specific embodiment of the present invention, the lipid pharmaceutical composition forms a lipid nanoparticle containing a drug (LNP-pharmaceutical composition), and the particle size of lipid nanoparticle is controlled by ultrasonic, extrusion, or microfluidic devices; the particle size is 1~1000 nm, preferably 20~500 nm, more preferably 60~200 nm, and most preferably 60~150 nm.

2. Examples

The following specific examples are for further description of the preparation of nitrogen-branched PEGylated lipids, lipid compositions containing nitrogen-branched PEGylated lipids, lipid pharmaceutical compositions and formulations thereof, and the biological activity assays. Said specific examples are for further detailed illustration of the present invention, not limiting the scope of the present invention. Wherein, in the examples of the preparation of nitrogen-branched PEGylated lipids, the structures of end-products were characterized by NMR, and the molecular weight was determined by GPC or MALDI-TOF.

2.1. Preparation of Nitrogen-Branched PEGylated Lipids

Example 1: Nitrogen-Branched PEGylated Lipids with/without a Lipid Moiety Containing Ester Bonds

Example 1.1: Nitrogen-Branched PEGylated Lipid E1-1 without Ester Bonds in $L_1$ and $L_2$

E1-1

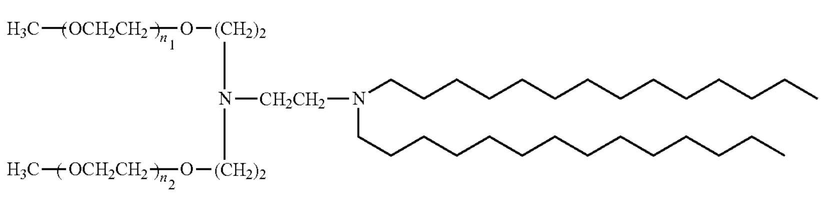

E1-1 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is $-CH_2CH_2-$, both $L_x$ are $-CH_2CH_2-$, and T is a methyl group. The molecular weight of each PEG chain is approximately 1 kDa, corresponding to $n_1 \approx n_2 \approx 22$.

The preparation method is as follows:

Step a: 1-Bromotetradecane (S1-2, 6.09 g, 22.0 mmol) was dissolved with 80 mL N,N-dimethylformamide (DMF), added with the ethylenediamine derivative containing a Boc-protected amino group (S1-1, 1.60 g, 10.0 mmol) and potassium carbonate ($K_2CO_3$, 3.64 g, 26.4 mmol), and reacted overnight at room temperature while stirring. After the reaction was over, the reaction solution was concentrated under reduced pressure, and then poured into 80 mL dichloromethane. After washing with 10% citric acid (40 mL*2) and brine (40 mL*2) successively, the organic phase was dried over anhydrous sodium sulfate, filtered, concentrated under reduced pressure, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain the lipid compound S1-3 (3.92 g).

Step b: First alkylation reaction: The linear methoxypolyethylene glycol-methyl sulfonate derivative S1-4 (1.32 g, 1.2 mmol, $M_n \approx 1.1$ kDa, $n_1 \approx 22$, PDI=1.01) was dissolved with 35 mL dichloromethane, added with S1-3 (3.26 g, 7.2 mmol), and reacted for 24 hours at room temperature. After the reaction was over, the reaction solution was concentrated, added with a phosphate buffer of pH=7.0, stirred for 16 h, and purified by column chromatography to obtain the polyethylene glycol derivative S1-5 containing a secondary amino group (1.39 g).

Step c: Second alkylation reaction: S1-5 (1.20 g, 0.8 mmol, $M_n \approx 1.5$ kDa, $n_1 \approx 22$, PDI=1.01) and S1-4 (0.88 g, 0.8 mmol, $M_n \approx 1.1$ kDa, $n_1 \approx 22$, PDI=1.01) were dissolved with 10 mL dichloromethane and reacted for 24 hours at room temperature. After the reaction was over, the reaction solution was concentrated, added with a phosphate buffer of pH=7.0, stirred for 16 h, and purified by column chromatography to obtain the nitrogen-branched polyethylene glycol derivative E1-1 (0.76 g). $^{1}H$ NMR (400 MHz, $CDCl_3$) δ: 3.75-3.42 (m, PEG; 4H, $—OCH_2CH_2N<$), 3.33 (s, 6H, $—OCH_3$), 2.83-2.72 (m, 4H, $—OCH_2CH_2N<$), 2.59-2.35 (m, 4H, $>N(CH_2)_2N<$; 4H, $—N[CH_2(CH_2)_2\text{-}]_2$), 1.48-0.98 (m, 44H, $—CH_2CH_2CH_2—$; 4H, $—CH_2CH_3$), 0.82 (t, 6H, $—CH_2CH_3$). The molecular weight determined by GPC was approximately 2.5 kDa, PDI=1.02.

E1-2 corresponds to the general formula (2); wherein, $B_1$ and $B_2$ are both ethylene groups, $L_1$ and $L_2$ are both ester groups —OC(═O)—, $R_1$ and $R_2$ are both

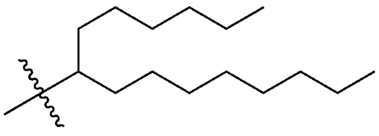

,

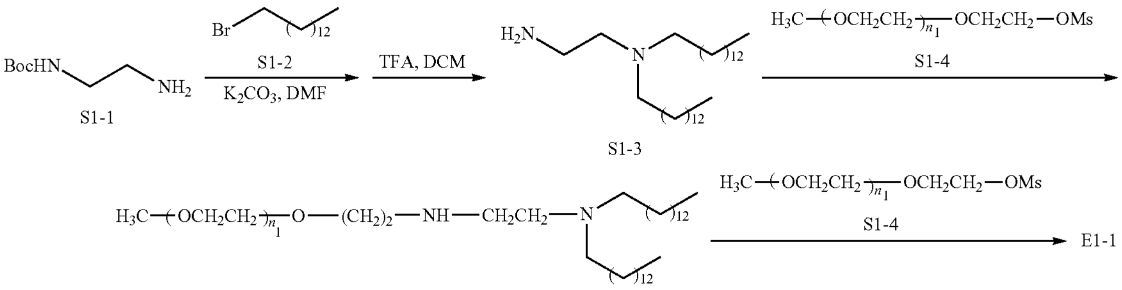

S1-1

S1-3

S1-5

Referring to the above steps a-c, a linear methoxypolyethylene glycol-methyl sulfonate derivative with a molecular weight of approximately 2.1 kDa ($n_1$≈45, PDI=1.02) was used, as starting material, to obtain the E1-1-2k (PDI=1.02) which has the molecular weight of approximately 2 kDa per PEG arm, the same structure as E1-1, and a total molecular weight of approximately 4.5 kDa. The structure was determined by NMR.

Referring to the above steps a-c, a linear methoxypolyethylene glycol-methyl sulfonate derivative with a molecular weight of 639 Da ($n_1$=11, PDI=1) was used, as starting material, to obtain the E1-1-500 (monodisperse) which has a molecular weight of approximately 500 Da per PEG arm, the same structure as E1-1, and a total molecular weight of approximately 1539 Da. The structure was determined by NMR.

Example 1.2: Nitrogen-Branched PEGylated Lipid E1-2 with Ester Bonds in $L_1$ and $L_2$ $L_d$ is $—CH_2CH_2—$, both $L_x$ are $—CH_2CH_2—$, and T is a methyl group. The molecular weight of each PEG chain is approximately 1 kDa, corresponding to $n_1≈n_2≈22$.

The preparation method is as follows:

Step a: Under argon atmosphere, DCC (9.27 g, 45.0 mmol) was added into a round-bottom flask containing 2-hexyldecanoic acid (S1-6, 7.68 g, 30.0 mmol), 6-bromohexanol (S1-7, 5.97 g, 33.0 mmol) and DMAP (0.92 g, 7.5 mmol) which were dissolved in dichloromethane (100 mL), and reacted for 16 h at room temperature. After the reaction was over, the precipitates were removed by filtration. The filtrate was concentrated and the residue was purified by silica gel column chromatography to obtain the compound S1-8 (10.55 g).

Step b: S1-8 (9.22 g, 22.0 mmol) was dissolved with 100 mL N,N-dimethylformamide (DMF), added with S1-1 (1.60 g, 10.0 mmol) and potassium carbonate ($K_2CO_3$, 3.64 g, 26.4 mmol), and reacted overnight at room temperature while stirring. After the reaction was over, the reaction solution was concentrated under reduced pressure and then poured into 100 mL dichloromethane. After washing with 10% citric acid (50 mL*2) and brine (50 mL*2) succes-

E1-2

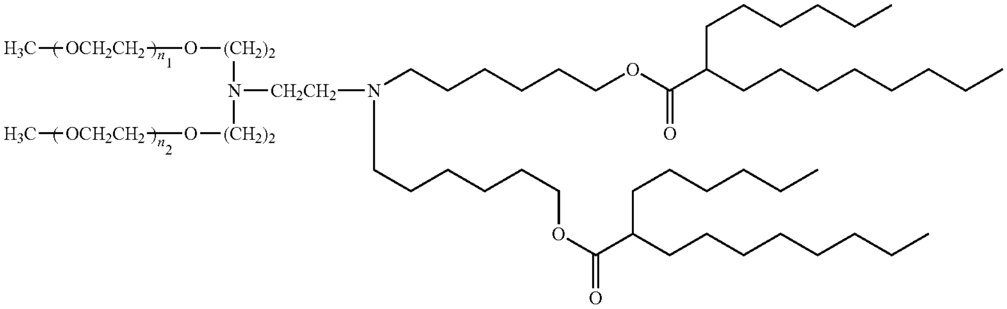

sively, the organic phase was dried over anhydrous sodium sulfate, filtered, concentrated under reduced pressure, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain the lipid compound S1-9 (6.05 g).

Step c: Referring to the reaction conditions and feeding ratios in the Steps c-d of Example 1.1, S1-9 (5.31 g, 7.2 mmol) underwent two alkylation reactions with S1-4 (1.2 mmol for the first, 0.8 mmol for the second). After purification with column chromatography, the nitrogen-branched PEGylated lipid E1-2 (0.63 g) was obtained. $^1$H NMR (400 MHz, $CDCl_3$) δ: 4.08 (t, 4H, $—CH_2OC(═O)—$), 3.76-3.42 (m, PEG; 4H, $—OCH_2CH_2N<$), 3.36 (s, 6H, $—OCH_3$), 2.85-2.70 (m, 4H, $—OCH_2CH_2N<$), 2.58-2.36 (m, 4H, $>N(CH_2)_2N<$; 4H, $—N[CH_2(CH_2)_2-]_2$), 2.35-2.28 (m, 2H, $—OC(═O)CH<$), 1.71-1.08 (m, 56H, $—CH_2CH_2CH_2—$; 8H, $—CH_2CH_3$), 0.88 (t, 12H, $—CH_2CH_3$). The molecular weight determined by GPC was approximately 2.8 kDa, PDI=1.02.

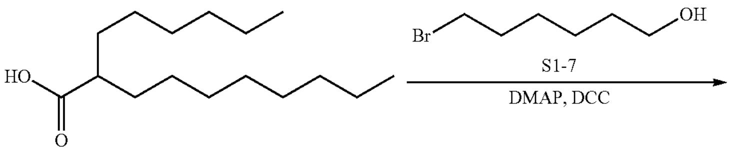

S1-6

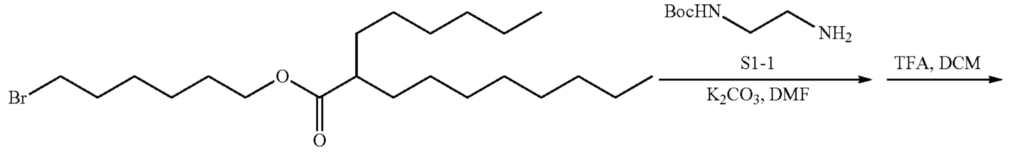

S1-8

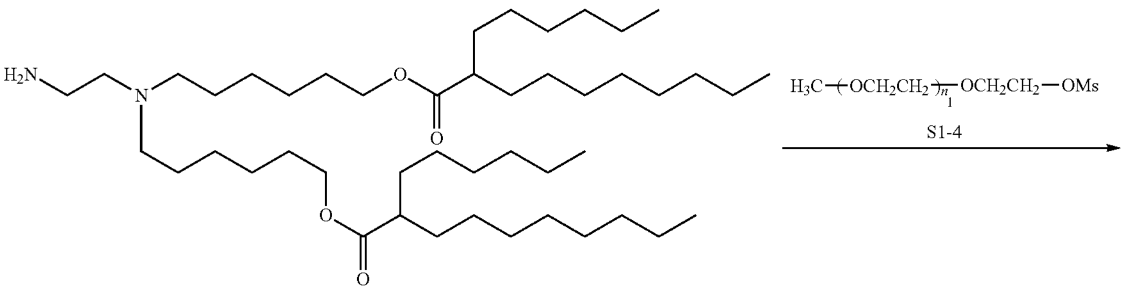

S1-9

Example 1.3: Nitrogen-Branched PEGylated Lipid E1-3 with Ester Bonds in $L_1$ and $L_2$

E1-3

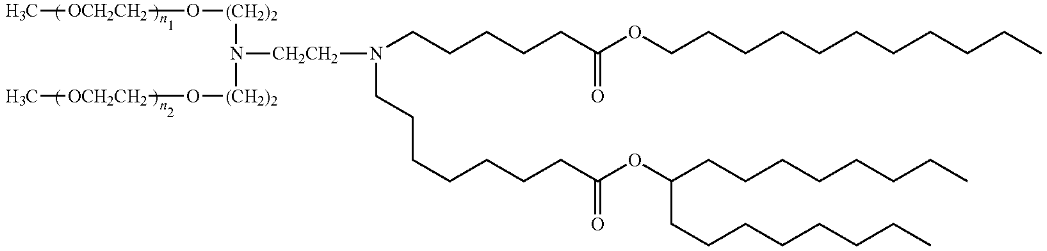

E1-3 corresponds to the general formula (2); wherein, $B_1$ is a pentylene group, $B_2$ is a heptylene group, $L_1$ and $L_2$ are both ester groups —C(═O)O—, $R_1$ is an undecyl group, $R_2$ is

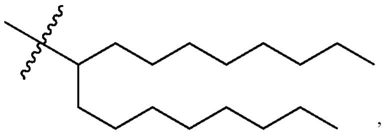

$L_d$ is $—CH_2CH_2—$, both $L_x$ are $—CH_2CH_2—$, and T is a methyl group. The molecular weight of each PEG chain is approximately 1 kDa, corresponding to $n_1 \approx n_2 \approx 22$.

The preparation method is as follows:

Step a: Under argon atmosphere, DCC (6.80 g, 33.0 mmol) was added into a round-bottom flask containing 2-hexyldecanoic acid (51-10, 4.91 g, 22.0 mmol), 6-bromo-hexanol (S1-11, 6.20 g, 24.2 mmol) and DMAP (0.67 g, 5.5 mmol) which were dissolved in dichloromethane (80 mL), and reacted for 16 h at room temperature. After the reaction was over, the precipitates were removed by filtration. The filtrate was concentrated and the residue was purified by silica gel column chromatography to obtain the compound S1-12 (8.64 g).

Step b: S1-12 (8.32 g, 18.0 mmol) was dissolved with 100 mL N,N-dimethylformamide (DMF), added with S1-1 (2.40 g, 15.0 mmol) and potassium carbonate ($K_2CO_3$, 2.98 g, 21.6 mmol), and reacted overnight at room temperature while stirring. After the reaction was over, the reaction solution was concentrated under reduced pressure and then poured into 100 mL dichloromethane. After washing with 10% citric acid (50 mL*2) and brine (50 mL*2) successively, the organic phase was dried over anhydrous sodium sulfate, filtered, concentrated under reduced pressure, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain the lipid compound S1-13 (6.64 g).

Step c: S1-13 (5.41 g, 10.0 mmol) was dissolved with dried THE (60 mL), slowly added with NaH (60%, 4.00 g, 100.0 mmol) in an ice bath, and reacted for 1 h in an ice bath. After the reaction was over, undecyl 6-bromohexanoate (S1-14, 4.19 g, 12.0 mmol, wherein S1-14 was prepared via the reaction of 6-bromohexanoic acid and 1-undecanol, referring to Step a in this example) was added, and the reaction was continued for 1 h while stirring in an ice bath, after which the reaction solution was slowly returned to room temperature and the reaction was continued overnight. After the reaction was over, the reaction was placed in an ice bath, and then 1 mL of water was added slowly to quench the reaction. After stirring for 30 minutes, the solvent was removed via rotary evaporation, and water (60 mL) was added and mixed while stirring. Then, extraction was performed twice using dichloromethane (30 mL*2). The dichloromethane organic phases were combined and washed with a saturated solution of sodium chloride (30 mL*2). The organic phase was concentrated under reduced pressure, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain the lipid compound S1-15 (6.28 g).

Step d: Referring to the reaction conditions and feeding ratios in the Steps c-d of Example 1.1, S1-15 (5.10 g, 7.2 mmol) underwent two alkylation reactions with S1-4 (1.2 mmol for the first, 0.8 mmol for the second). After purification with column chromatography, the nitrogen-branched PEGylated lipid E1-3 (0.74 g) was obtained. $^1H$ NMR (400 MHz, $CDCl_3$) δ: 4.18-4.00 (m, 2H, $—C(═O)OCH_2—$; 1H, —C(═O)OCH<), 3.75-3.41 (m, PEG; 4H, $—OCH_2CH_2N$<), 3.36 (s, 6H, $—OCH_3$), 2.83-2.72 (m, 4H, $—OCH_2CH_2N$<), 2.60-2.40 (m, 4H, >$N(CH_2)_2N$<; 4H, $—[NCH_2(CH_2)_2-]_2$), 2.35-2.24 (m, 4H, $—CH_2C(═O)O—$), 1.69-1.11 (m, 56H, $—CH_2CH_2CH_2—$; 6H, $—CH_2CH_3$), 0.85 (t, 9H, $—CH_2CH_3$). The molecular weight determined by GPC was approximately 2.8 kDa, PDI=1.02.

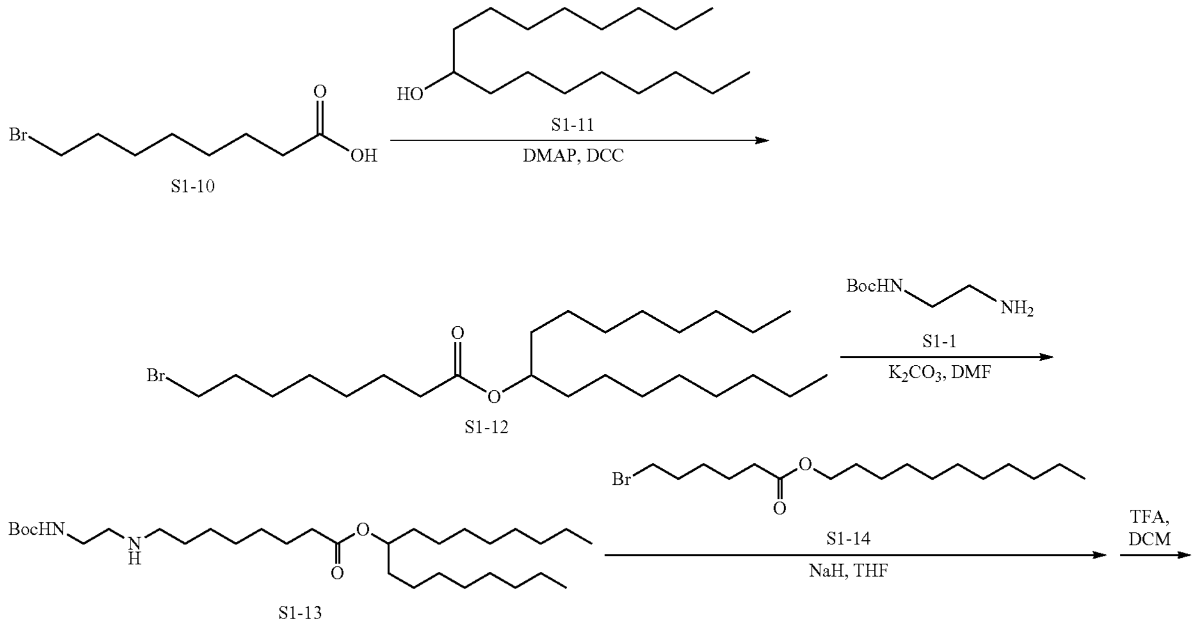

-continued

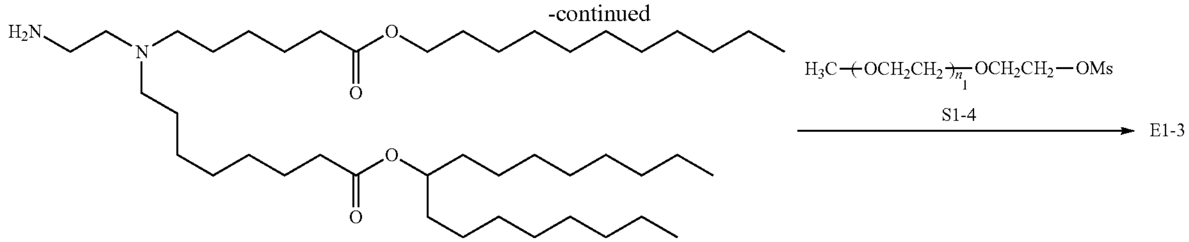

S1-15

Example 1.4: Nitrogen-Branched PEGylated Lipid E1-4 without Ester Bonds in $L_1$ and $L_2$

E1-4

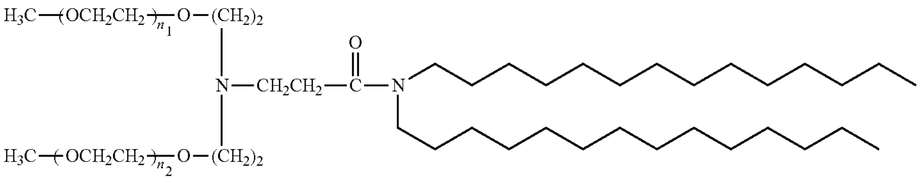

E1-4 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is $-CH_2CH_2C(=O)-$, both $L_x$ are $-CH_2CH_2-$, and T is a methyl group. The molecular weight of each PEG chain is approximately 1 kDa, corresponding to $n_1 \approx n_2 \approx 22$.

The preparation method is as follows:

Step a: Myristic acid (S1-16, 1.82 g, 8.0 mmol) was dissolved with 40 mL anhydrous dichloromethane, added with N-hydroxysuccinimide (NHS, 1.38 g, 12.0 mmol), and then added with DCC (2.47 g, 12.0 mmol). Into the solution of tetradecylamine (S1-17, 2.04 g, 9.6 mmol) in 40 mL dichloromethane was added DMAP (0.20 g, 1.6 mmol). The aforementioned two solutions were mixed and reacted for 24 hours at room temperature while stirring. After the reaction was over, the precipitates were removed by filtration. The filtrate was concentrated under reduced pressure and purified by column chromatography to obtain S1-18 (2.85 g).

Step b: Under nitrogen protection, S1-18 (2.12 g, 5.0 mmol) was dissolved with 1M $BH_3$/THF solution (40 mL) and heated to 80° C., and the reaction was conducted for 24 hours while stirring. Then, the reaction solution was cooled to room temperature, and THF was removed via rotary evaporation. The residue was dissolved with 4N hydrochloric acid methanol solution and refluxed for 4 hours under nitrogen protection. The methanol was removed, and the residue was dissolved with 50 mL water and then washed with ether (25 mL*3). The pH was adjusted to 11 with a 20% NaOH solution. The alkaline mixture was extracted with dichloromethane (30 mL*3), and the organic phases were combined, dried over anhydrous sodium sulfate, filtered, concentrated, and purified by column chromatography to obtain the secondary amine compound S1-19 (1.60 g).

Step c: In 15 mL anhydrous dichloromethane was dissolved the symmetrical nitrogen-branched polyethylene glycol-propionic acid derivative S1-20 (2.10 g, 1.0 mmol, $M_n \approx 2.1$ kDa, $n_1 \approx n_2 \approx 22$, PDI=1.01, obtained via deprotection after two alkylation reactions of the β-alanine derivative containing a Boc-protected carboxyl group and S1-4, referring to Steps c-d of Example 1.1), and then NHS (0.17 g, 1.5 mmol) and DCC (0.31 g, 1.5 mmol) were successively added. Into the solution of S1-19 (1.23 g, 3.0 mmol) in 15 mL dichloromethane was added DMAP (24 mg, 0.2 mmol). The aforementioned two solutions were mixed and reacted for 24 hours at room temperature while stirring. After the reaction was over, the precipitates were removed by filtration. The filtrate was concentrated under reduced pressure and purified by column chromatography to obtain the nitrogen-branched PEGylated lipid E1-4 (1.07 g). $^1H$ NMR (400 MHz, $CDCl_3$) δ: 3.77-3.42 (m, PEG; 4H, $-OCH_2CH_2N<$), 3.37 (s, 6H, $-OCH_3$), 3.29-3.09 (m, 4H, $-[NCH_2(CH_2)_2-]_2$), 2.88-2.71 (m, 4H, $-OCH_2CH_2N<$), 2.64-2.21 (m, 4H, $>N(CH_2)_2C(=O)N<$), 1.59-1.02 (m, 44H, $-CH_2CH_2CH_2-$; 4H, $-CH_2CH_3$), 0.84 (t, 6H, $-CH_2CH_3$). The molecular weight determined by GPC was approximately 2.5 kDa, PDI=1.01.

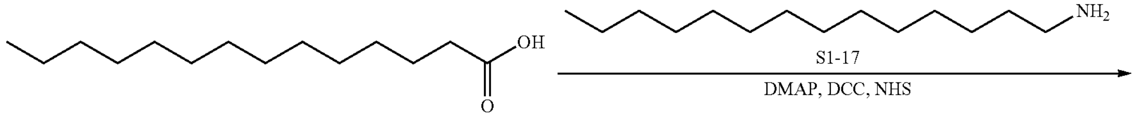

S1-16

-continued

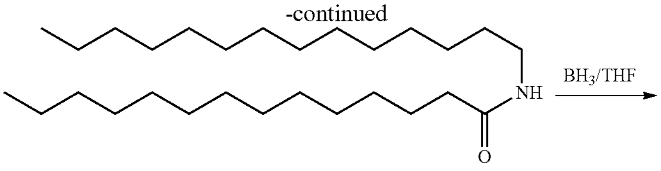

S1-18

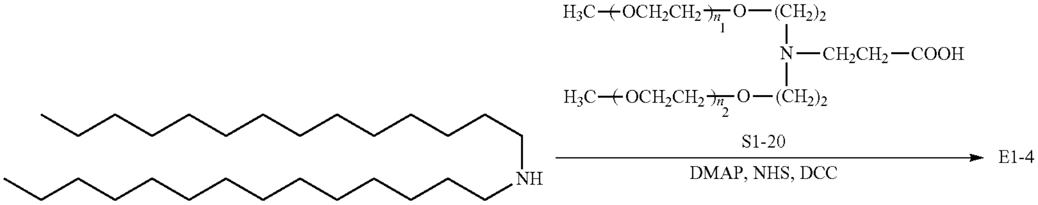

S1-19

Example 1.5: Nitrogen-Branched PEGylated Lipid E1-5 without Ester Bonds in $L_1$ and $L_2$

E1-5

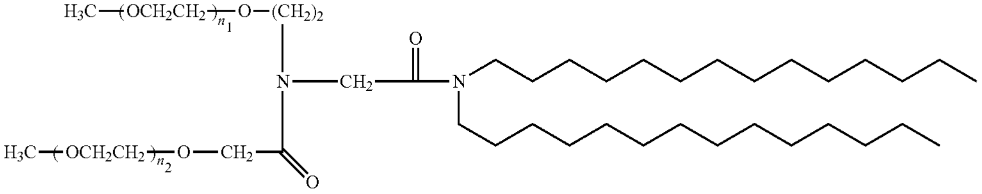

E1-5 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is —$CH_2C$(═O)—, two $L_x$ are respectively —$CH_2CH_2$— and —$CH_2C$(═O)—, and T is a methyl group. The molecular weight of each PEG chain is approximately 1 kDa, corresponding to $n_1 \approx n_2 \approx 22$.

The preparation method is as follows:

In 15 mL anhydrous dichloromethane was dissolved the asymmetrical nitrogen-branched polyethylene glycol-acetic acid derivative S2-1 (2.10 g, 1.0 mmol, $M_n \approx 2.1$ kDa, $n_1 \approx n_2 \approx 22$, PDI=1.01, synthesized according to CN1243779C), and then NHS (0.17 g, 1.5 mmol) and DCC (0.31 g, 1.5 mmol) were successively added. Into the solution of S1-19 (1.23 g, 3.0 mmol) in 15 mL dichloromethane was added DMAP (24 mg, 0.2 mmol). The aforementioned two solutions were mixed and reacted for 24 hours at room temperature while stirring. After the reaction was over, the precipitates were removed by filtration. The filtrate was concentrated under reduced pressure and purified by column chromatography to obtain E1-5 (1.15 g). $^1H$ NMR (400 MHz, $CDCl_3$) δ: 4.25 (s, 1H, —$OCH_aH_bC$(═O)N<), 4.20 (s, 1H, —$OCH_aH_bC$(═O)N<), 4.13 (s, 1H, >$NCH_aH_bC$(═O)N<), 4.04 (s, 1H, >$NCH_aH_bC$(═O)N<), 3.77-3.35 (m, PEG; 4H, —$OCH_2CH_2N$<), 3.31 (s, 6H, —$OCH_3$), 3.24-3.04 (m, 4H, >$NCH_2C$(═O)N[$CH_2(CH_2)_2$-]$_2$), 1.56-0.96 (m, 44H, —$CH_2CH_2CH_2$—; 4H, —$CH_2CH_3$), 0.81 (t, 6H, —$CH_2CH_3$). The molecular weight determined by GPC was approximately 2.5 kDa, PDI=1.01.

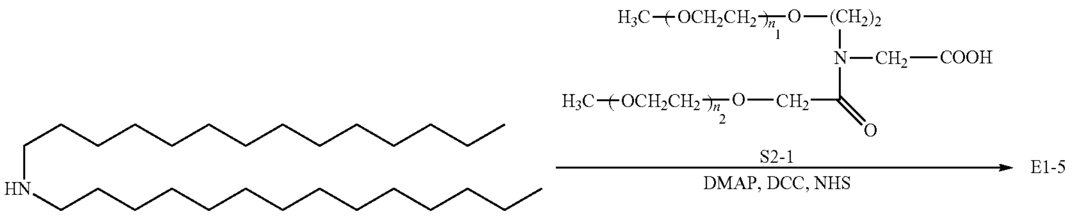

S1-19

Example 2: Nitrogen-Branched PEGylated Lipids with Amide Bonds and/or Ester Bonds in $L_d$ Example 2.1: Nitrogen-Branched PEGylated Lipid E2-1 with an Amide Bond in $L_d$

E2-1

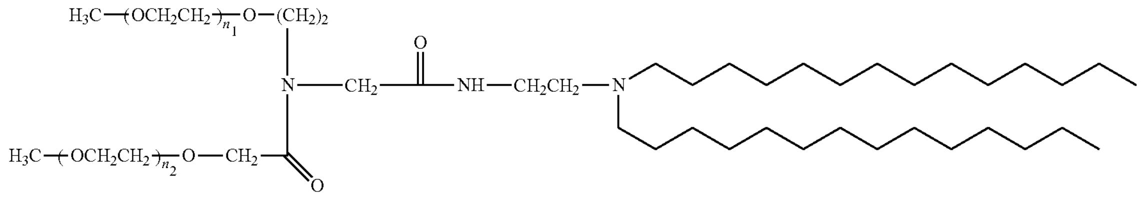

E2-1 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is $—CH_2C(═O)NHCH_2CH_2—$, two $L_x$ are respectively $—CH_2CH_2—$ and $—CH_2C(═O)—$, and T is a methyl group. The molecular weight of each PEG chain is approximately 1 kDa, corresponding to $n_1 \approx n_2 \approx 22$.

The preparation method is as follows:

In 15 mL anhydrous dichloromethane was dissolved S2-1 (2.10 g, 1.0 mmol, $M_n \approx 2.1$ kDa, $n_1 \approx n_2 \approx 22$, PDI=1.01), and then NHS (0.17 g, 1.5 mmol) and DCC (0.31 g, 1.5 mmol) were successively added. Into the solution of S1-3 (1.36 g, 3.0 mmol) in 15 mL dichloromethane was added DMAP (24 mg, 0.2 mmol). The aforementioned two solutions were mixed and reacted for 24 hours at room temperature while stirring. After the reaction was over, the precipitates were removed by filtration. The filtrate was concentrated under reduced pressure and purified by column chromatography to obtain the nitrogen-branched PEGylated lipid E2-1 (1.30 g). $^1H$ NMR (400 MHz, $CDCl_3$) δ: 4.24 (s, 1H, $—OCH_aH_bC(═O)N<$), 4.18 (s, 1H, $—OCH_aH_bC(═O)N<$), 3.76-3.27 (m, PEG; 4H, $—OCH_2CH_2N<$; 2H, $>NCH_2C(═O)NH—$; 6H, $—OCH_3$), 3.22-2.74 (m, 4H, $—C(═O)NHCH_2CH_2N<$; 4H, $—N[CH_2(CH_2)_2-]_2$), 1.46-1.03 (m, 44H, $—CH_2CH_2CH_2—$; 4H, $—CH_2CH_3$), 0.85 (t, 6H, $—CH_2CH_3$). The molecular weight determined by GPC was approximately 2.6 kDa, PDI=1.01.

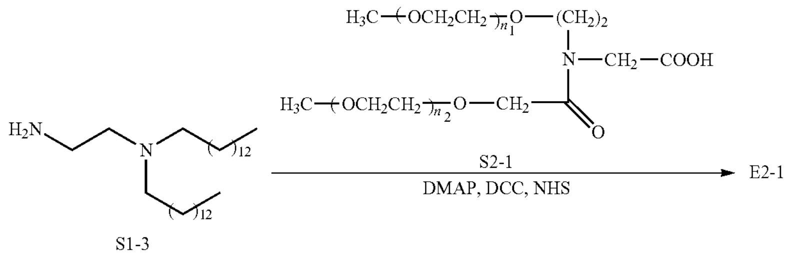

Example 2.2: Nitrogen-Branched PEGylated Lipid E2-2 with an Ester Bond in $L_d$

E2-2

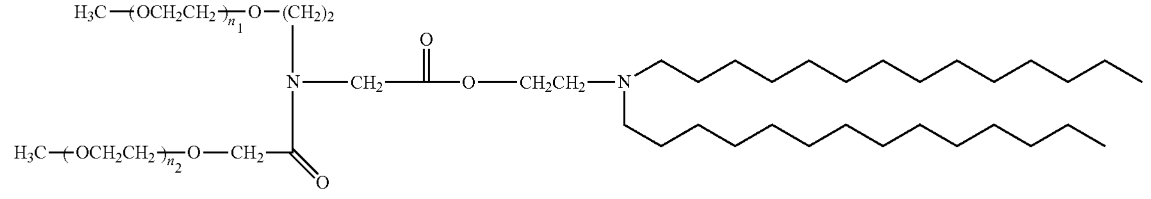

E2-2 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is —$CH_2C$(═O)$OCH_2CH_2$—, two $L_x$ are respectively —$CH_2CH_2$— and —$CH_2C$(═O)—, and T is a methyl group. The molecular weight of each PEG chain is approximately 1 kDa, corresponding to $n_1 \approx n_2 \approx 22$.

The preparation method is as follows:

Step a: S1-2 (3.05 g, 11.0 mmol) was dissolved with 40 mL of N,N-dimethylformamide (DMF), added with the ethanolamine derivative containing a hydroxyl group protected by TBS (S2-2, 0.88 g, 5.0 mmol) and potassium carbonate ($K_2CO_3$, 1.82 g, 13.2 mmol), and reacted overnight at room temperature while stirring. After the reaction was over, the reaction solution was concentrated under reduced pressure and then poured into 40 mL dichloromethane. After washing with 10% citric acid (20 mL*2) and brine (20 mL*2) successively, the organic phase was dried over anhydrous sodium sulfate, filtered, concentrated under reduced pressure, added with 20 mL tetrahydrofuran (THF), and further added with 20 mL of the 1M solution of tetra-n-butylammonium fluoride (TBAF) in tetrahydrofuran. The deprotection reaction was continued overnight to remove TBS. After the reaction was over, the reaction solution was concentrated and extracted. The organic phases were combined, dried over anhydrous sodium sulfate, filtered, concentrated, and purified by column chromatography to obtain the lipid compound S2-3 (1.90 g).

Step b: Under argon atmosphere, DCC (0.31 g, 1.5 mmol) was added into a round-bottom flask containing S2-1 (2.10 g, 1.0 mmol, $M_n \approx 2.1$ kDa, $n_1 \approx n_2 \approx 22$, PDI=1.01), S2-3 (1.36 g, 3.0 mmol) and DMAP (31 mg, 0.3 mmol) which were dissolved in dichloromethane (15 mL), and reacted at room temperature for 16 h. After the reaction was over, the precipitates were removed by filtration. The filtrate was concentrated and then purified by column chromatography to obtain the nitrogen-branched PEGylated lipid E2-2 (1.14 g). $^1$H NMR (400 MHz, $CDCl_3$) δ: 4.22 (s, 1H, —$OCH_aH_bC$(═O)N<), 4.17 (s, 1H, —$OCH_aH_bC$(═O)N<), 4.06 (t, 2H, —C(═O)$OCH_2CH_2$N<), 3.98 (s, 2H, >$NCH_2C$(═O)O—), 3.76-3.30 (m, PEG; 4H, —$OCH_2CH_2$N<; 6H, —$OCH_3$), 2.61 (t, 2H, —C(═O)$OCH_2CH_2$N<), 2.44-2.35 (m, 4H, >$NCH_2(CH_2)_2$—), 1.47-1.02 (m, 44H, —$CH_2CH_2CH_2$—; 4H, —$CH_2CH_3$), 0.83 (t, 6H, —$CH_2CH_3$). The molecular weight determined by GPC was approximately 2.6 kDa, PDI=1.01.

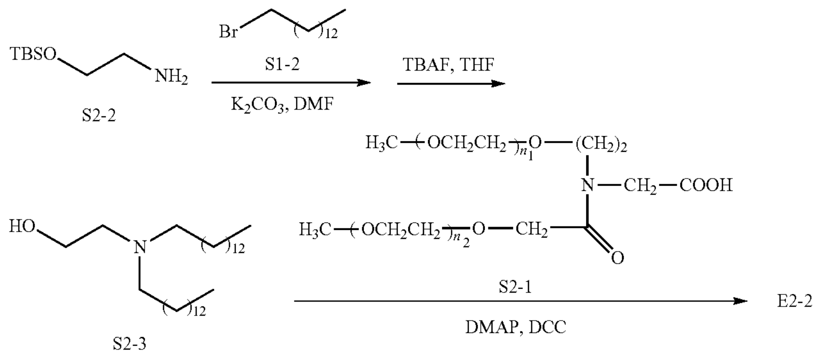

Example 2.3: Nitrogen-Branched PEGylated Lipid E2-3 with an Amide Bond and an Ester Bond in $L_d$

E2-3

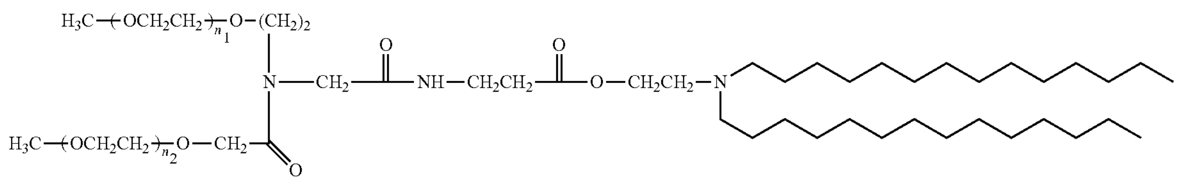

E2-3 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is —$CH_2C$(═O)$NHCH_2CH_2C$(═O)$OCH_2CH_2$—, two $L_x$ are respectively —$CH_2CH_2$— and —$CH_2C$(═O)—, and T is a methyl group. The molecular weight of each PEG chain is approximately 1 kDa, corresponding to $n_1 \approx n_2 \approx 22$.

The preparation method is as follows:

Step a: Under argon atmosphere, the 3-aminopropionic acid derivative containing an amino group protected by Boc (S2-4, 1.13 g, 6.0 mmol), the lipid compound S2-3 containing a free hydroxyl group (2.18 g, 4.8 mmol), and DMAP (0.18 g, 1.5 mmol) were successively dissolved in dichloromethane (30 mL), and then DCC (1.85 g, 9.0 mmol) was added. The reaction proceeded at room temperature for 16 h. After the reaction was over, the precipitates were removed by filtration. The filtrate was concentrated, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain the lipid compound S2-5 (2.07 g) having a free amino group.

Step b: In 15 mL anhydrous dichloromethane was dissolved S2-1 (2.10 g, 1.0 mmol, $M_n \approx 2.1$ kDa, $n_1 \approx n_2 \approx 22$, PDI=1.01), and then NHS (0.17 g, 1.5 mmol) and DCC (0.31 g, 1.5 mmol) were successively added. Into the solution of S2-5 (1.58 g, 3.0 mmol) in 15 mL dichloromethane was added DMAP (24 mg, 0.2 mmol). The aforementioned two solutions were mixed and reacted for 24 hours at room temperature while stirring. After the reaction was over, the precipitates were removed by filtration. The filtrate was concentrated under reduced pressure and purified by column chromatography to obtain the nitrogen-branched PEGylated lipid E2-3 (1.04 g). $^1$H NMR (400 MHz, $CDCl_3$) δ: 4.26 (s, 1H, $—OCH_aH_bC(=O)N<$), 4.20 (s, 1H, $—OCH_aH_bC(=O)N<$), 4.05 (t, 2H, $—C(=O)OCH_2CH_2N<$), 3.73-3.27 (m, PEG; 4H, $—OCH_2CH_2N<$; 2H, $>NCH_2C(=O)NH—$; 6H, $—OCH_3$), 3.22-2.93 (m, 2H, $—C(=O)NHCH_2CH_2C(=O)O—$; 4H, $—N[CH_2(CH_2)_2-]_2$), 2.60 (t, 2H, $—C(=O)OCH_2CH_2N<$), 2.47-2.32 (m, 2H, $—C(=O)NHCH_2CH_2C(=O)O—$), 1.46-1.02 (m, 44H, $—CH_2CH_2CH_2—$; 4H, $—CH_2CH_3$), 0.84 (t, 6H, $—CH_2CH_3$). The molecular weight determined by GPC was approximately 2.7 kDa, PDI=1.01.

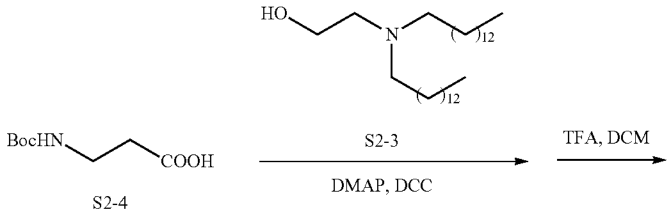

S2-4

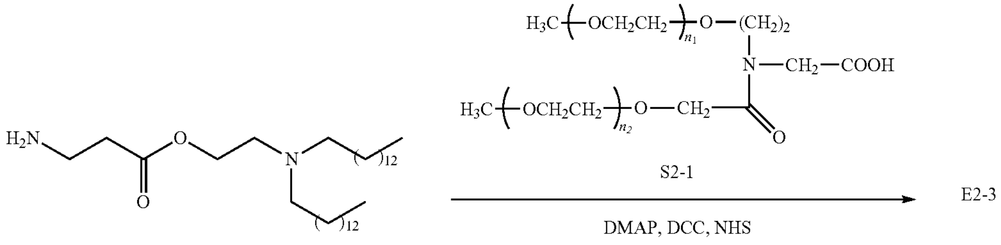

S2-5

Example 2.4: Nitrogen-Branched PEGylated Lipid E2-4 with an Amide Bond in $L_d$

E2-4

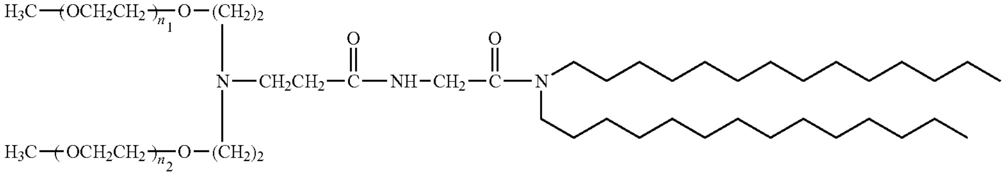

E2-4 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is $—CH_2CH_2C(=O)NHCH_2C(=O)—$, both $L_x$ are $—CH_2CH_2—$, and T is a methyl group. The molecular weight of each PEG chain is approximately 1 kDa, corresponding to $n_1 \approx n_2 \approx 22$.

The preparation method is as follows:

Step a: In 15 mL anhydrous dichloromethane was dissolved the glycine derivative containing an amino group protected by Boc (S2-6, 1.05 g, 6.0 mmol), and then NHS (1.04 g, 9.0 mmol) and DCC (1.85 g, 9.0 mmol) were successively added. Into the solution of the secondary amine compound S1-19 (1.97 g, 4.8 mmol) in 15 mL dichloromethane was added DMAP (0.15 g, 1.2 mmol). The aforementioned two solutions were mixed and reacted for 24 hours at room temperature while stirring. After the reaction was over, the precipitates were removed by filtration. The filtrate was concentrated under reduced pressure and purified by column chromatography to obtain S2-7 (2.02 g).

Step b: In 15 mL anhydrous dichloromethane was dissolved the nitrogen-branched polyethylene glycol-propionic acid derivative S1-20 (2.10 g, 1.0 mmol, $M_n \approx 2.1$ kDa, $n_1 \approx n_2 \approx 22$, PDI=1.01), and then NHS (0.17 g, 1.5 mmol) and DCC (0.31 g, 1.5 mmol) were successively added. Into the solution of S2-7 (1.40 g, 3.0 mmol) in 15 mL dichloromethane was added DMAP (24 mg, 0.2 mmol). The aforementioned two solutions were mixed and reacted for 24 hours at room temperature while stirring. After the reaction was over, the precipitates were removed by filtration. The filtrate was concentrated under reduced pressure and purified by column chromatography to obtain the nitrogen-branched PEGylated lipid E2-4 (1.17 g). $^1H$ NMR (400 MHz, $CDCl_3$) δ: 4.09 (s, 2H, $—C(=O)NHCH_2C(=O)N<$), 3.76-3.25 (m, PEG; 4H, $—OCH_2CH_2N<$; 6H, $—OCH_3$; 2H, $>NCH_2CH_2C(=O)NH—$), 3.24-3.02 (m, 4H, $—N[CH_2(CH_2)_2-]_2$), 2.81-2.73 (m, 4H, $—OCH_2CH_2N<$), 2.48-2.31 (m, 2H, $>NCH_2CH_2C(=O)NH—$), 1.57-1.00 (m, 44H, $—CH_2CH_2CH_2—$; 4H, $—CH_2CH_3$), 0.85 (t, 6H, $—CH_2CH_3$). The molecular weight determined by GPC was approximately 2.6 kDa, PDI=1.01.

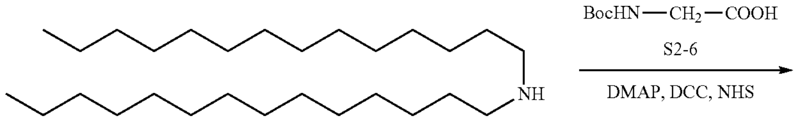

S1-19

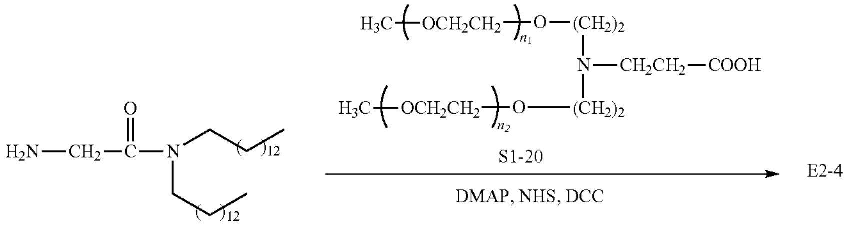

S2-7

Example 2.5: Nitrogen-Branched PEGylated Lipid E2-5 with an Ester Bond in $L_d$

E2-5

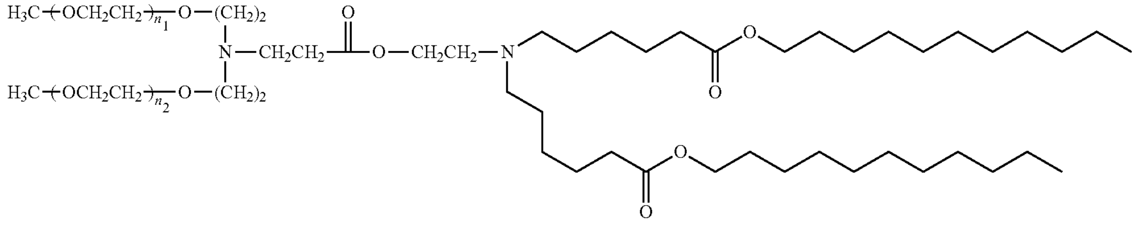

E2-5 corresponds to the general formula (2); wherein, $B_1$ and $B_2$ are both pentylene groups, $L_1$ and $L_2$ are ester groups —C(=O)O—, $R_1$ and $R_2$ are both undecyl groups, $L_d$ is —$CH_2CH_2C$(=O)$OCH_2CH_2$—, both $L_x$ are —$CH_2CH_2$—, and T is a methyl group. The molecular weight of each PEG chain is approximately 1 kDa, corresponding to $n_1 \approx n_2 \approx 22$.

The preparation method is as follows:

In 15 mL anhydrous dichloromethane was dissolved the nitrogen-branched polyethylene glycol-propionic acid derivative S1-20 (2.10 g, 1.0 mmol, $M_n \approx 2.1$ kDa, $n_1 \approx n_2 \approx 22$, PDI=1.01), and then NHS (0.17 g, 1.5 mmol) and DCC (0.31 g, 1.5 mmol) were successively added. Into the solution of S2-8 (1.79 g, 3.0 mmol, wherein S2-8 was synthesized from S1-14 and S2-2, referring to Step a in Example 2.2) in 15 mL dichloromethane was added DMAP (24 mg, 0.2 mmol). The aforementioned two solutions were mixed and reacted for 24 hours at room temperature while stirring. After the reaction was over, the precipitates were removed by filtration. The filtrate was concentrated under reduced pressure and purified by column chromatography to obtain the nitrogen-branched PEGylated lipid E2-5 (1.13 g). $^1$H NMR (400 MHz, $CDCl_3$) δ: 4.15-4.00 (m, 6H, —$CH_2OC$(=O)—), 3.76-3.40 (m, PEG; 4H, —$OCH_2CH_2N$<), 3.37-2.96 (m, 6H, —$OCH_3$; 4H, —N[$CH_2(CH_2)_2$-]$_2$), 2.87-2.70 (m, 4H, —$OCH_2CH_2N$<; 4H, >N$(CH_2)_2$C(=O)—; 2H, —C(=O)$OCH_2CH_2N$<), 2.39-2.21 (m, 4H, —$(CH_2)_2CH_2C$(=O)O—), 1.70-1.05 (m, 42H, —$CH_2CH_2CH_2$—; 6H, —$CH_2CH_3$), 0.85 (t, 6H, —$CH_2CH_3$). The molecular weight determined by GPC was approximately 2.7 kDa, PDI=1.01.

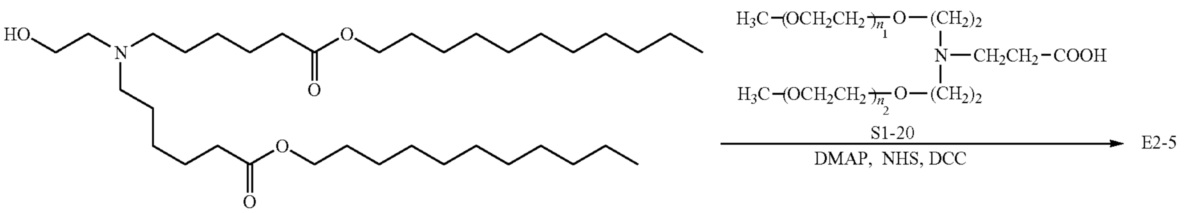

S2-8

Example 2.6: Nitrogen-Branched PEGylated Lipid E2-6 with an Ester Bond in $L_d$

E2-6

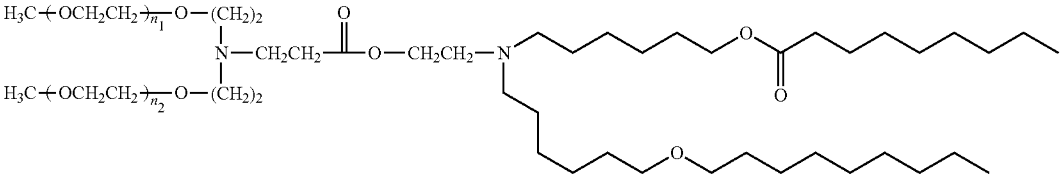

E2-6 corresponds to the general formula (2); wherein, $B_1$ and $B_2$ are both hexylene groups, $L_1$ is an ester group —OC(=O)—, $L_2$ is an ether group —O—, $R_1$ is an octyl group, $R_2$ is a nonyl group, $L_d$ is —$CH_2CH_2C$(=O)$OCH_2CH_2$—, both $L_x$ are —$CH_2CH_2$—, and T is a methyl group. The molecular weight of each PEG chain is approximately 1 kDa, corresponding to $n_1 \approx n_2 \approx 22$.

The preparation method is as follows:

Step a: S2-9 (3.08 g, 9.6 mmol, wherein S2-9 was obtained through the esterification reaction of 6-bromohexanol and nonanoic acid, using DMAP/DCC) was dissolved with 50 mL DMF, added with S2-2 (1.40 g, 8.0 mmol) and potassium carbonate ($K_2CO_3$, 1.59 g, 11.5 mmol), and reacted overnight at room temperature while stirring. After the reaction was over, the reaction solution was concentrated under reduced pressure and then poured into 50 mL dichloromethane. After washing with 10% citric acid (25 mL*2) and brine (25 mL*2) successively, the organic phase was dried over anhydrous sodium sulfate, filtered, concentrated under reduced pressure, and purified by column chromatography to obtain the lipid compound S2-10 (2.70 g).

Step b: S2-10 (2.08 g, 5.0 mmol) was dissolved with dried THE (40 mL), slowly added with NaH (60%, 2.00 g, 50.0 mmol) in an ice bath, and reacted for 1 h in an ice bath. After the reaction was over, the bromide-substituted alkane S2-11 (1.84 g, 6.0 mmol, wherein S2-11 was obtained via the alkylation reaction between the sulfonate derivative of 6-bromohexanol and 1-nonanol, using diphenylmethyl potassium/THF) was added, and the reaction was continued for 1 h while stirring in an ice bath, after which the reaction solution was slowly returned to room temperature and the reaction was continued overnight. After the reaction was over, the reaction was placed in an ice bath, and then 1 mL water was added slowly to quench the reaction. After stirring for 30 minutes, the solvent was removed via rotary evaporation, and water (40 mL) was added and mixed while stirring. Then, extraction was performed twice using dichloromethane (20 mL*2). The dichloromethane organic phases were combined and washed with a saturated solution of sodium chloride (20 mL*2). The organic phase was dried over anhydrous sodium sulfate, filtered, concentrated under reduced pressure, added with 20 mL tetrahydrofuran (THF), and further added with the 1M solution of TBAF/THF (20 mL). The deprotection reaction was continued overnight to remove TBS. After the reaction was over, the reaction solution was concentrated and extracted. The organic phases were combined, dried over anhydrous sodium sulfate, filtered, concentrated, and purified by column chromatography to obtain the lipid compound S2-12 (2.02 g).

Step c: Under argon atmosphere, S1-20 (2.10 g, 1.0 mmol, $M_n \approx 2.1$ kDa, $n_1 \approx n_2 \approx 22$, PDI=1.01), S2-12 (1.58 g, 3.0 mmol), and DMAP (31 mg, 0.3 mmol) were successively dissolved in dichloromethane (20 mL), and then DCC (0.31 g, 1.5 mmol) was added. The reaction proceeded at room temperature for 16 h. After the reaction was over, the precipitates were removed by filtration. The filtrate was concentrated and purified by column chromatography to obtain the nitrogen-branched PEGylated lipid E2-6 (1.27 g). $^1$H NMR (400 MHz, $CDCl_3$) δ: 4.15-4.03 (m, 4H, $—CH_2OC(═O)—$), 3.80-3.40 (m, PEG; 4H, $—OCH_2CH_2N<$; 4H, $—(CH_2)_2CH_2OCH_2(CH_2)_2—$), 3.37-2.95 (m, 6H, $—OCH_3$; 4H, $—N[CH_2(CH_2)_2\text{-}]_2$), 2.81-2.39 (m, 4H, $—OCH_2CH_2N<$; 4H, $>N(CH_2)_2C(═O)—$; 2H, $—C(═O)OCH_2CH_2N<$), 2.32-2.24 (m, 2H, $—(CH_2)_2CH_2C(═O)O—$), 1.76-1.12 (m, 36H, $—CH_2CH_2CH_2—$; 6H, $—CH_2CH_3$), 0.87 (t, 6H, $—CH_2CH_3$). The molecular weight determined by GPC was approximately 2.7 kDa, PDI=1.01.

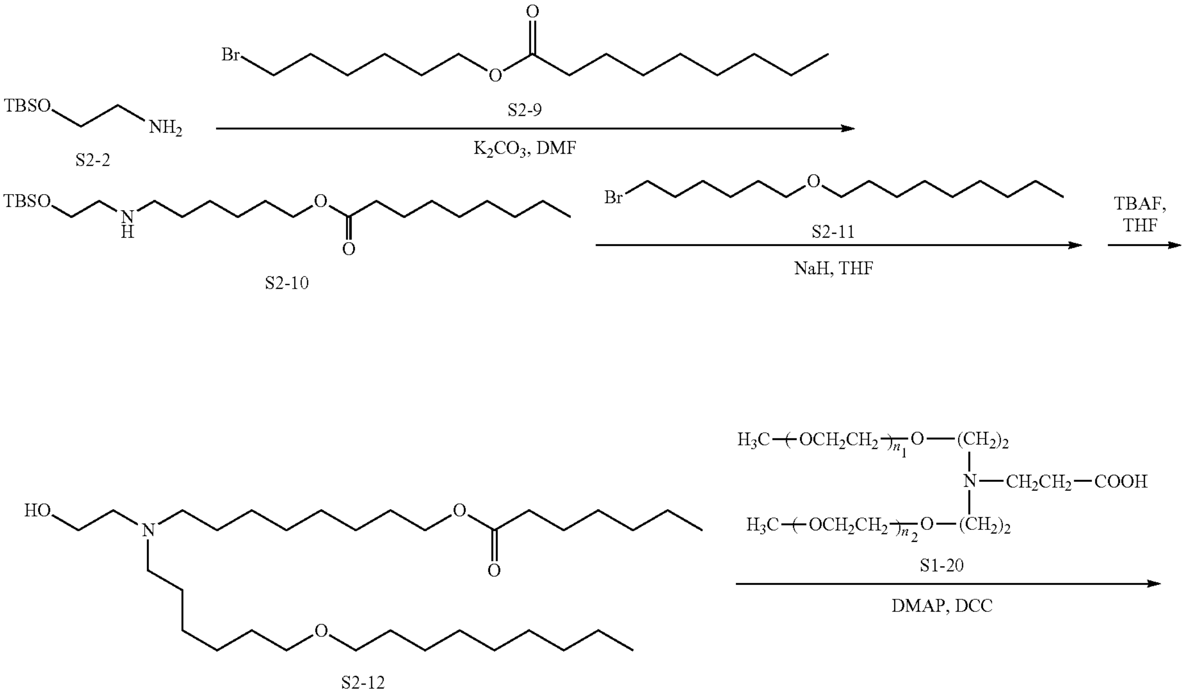

E2-6

Example 2.7: Nitrogen-Branched PEGylated Lipid E2-7 with an Amide Bond in $L_d$

E2-7

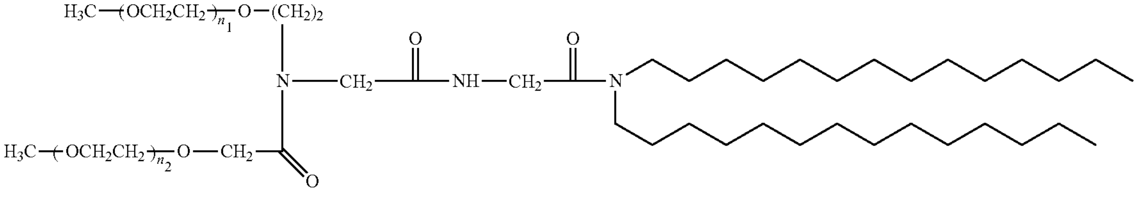

E2-7 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is $—CH_2C(═O)NHCH_2C(═O)—$, two $L_x$ are respectively $—CH_2CH_2—$ and $—CH_2C(═O)—$, and T is a methyl group. The molecular weight of each PEG chain is approximately 1 kDa, corresponding to $n_1 \approx n_2 \approx 22$.

The preparation method is as follows:

In 15 mL anhydrous dichloromethane was dissolved S2-1 (2.10 g, 1.0 mmol, $M_n \approx 2.1$ kDa, $n_1 \approx n_2 \approx 22$, PDI=1.01), and then NHS (0.17 g, 1.5 mmol) and DCC (0.31 g, 1.5 mmol) were successively added. Into the solution of S2-7 (1.40 g, 3.0 mmol) in 15 mL dichloromethane was added DMAP (24 mg, 0.2 mmol). The aforementioned two solutions were mixed and reacted for 24 hours at room temperature while stirring. After the reaction was over, the precipitates were removed by filtration. The filtrate was concentrated under reduced pressure and purified by column chromatography to obtain the nitrogen-branched PEGylated lipid E2-7 (1.07 g). $^1$H NMR (400 MHz, $CDCl_3$) δ: 4.19 (s, 1H, $—OCH_aH_bC(═O)N<$), 4.14 (s, 1H, $—OCH_aH_bC(═O)N<$), 4.07 (s, 2H, $—C(═O)NHCH_2C(═O)N<$), 3.76-3.20 (m, PEG; 4H, $—OCH_2CH_2N<$; 6H, $—OCH_3$; 4H, $—N[CH_2(CH_2)_2\text{-}]_2$; 2H, $>NCH_2C(═O)NH—$), 1.59-0.98 (m, 44H, $—CH_2CH_2CH_2—$; 4H, $—CH_2CH_3$), 0.82 (t, 6H, $—CH_2CH_3$). The molecular weight determined by GPC was approximately 2.6 kDa, PDI=1.01.

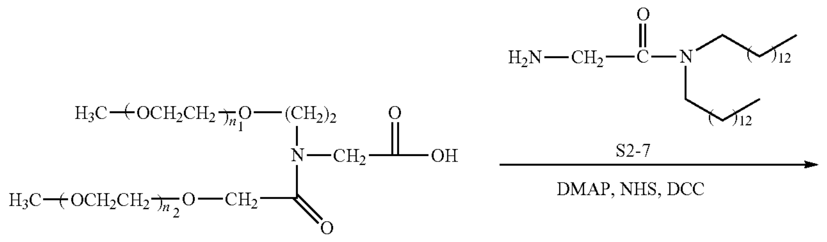

S2-1

E2-7

Example 3: Nitrogen-Branched PEGylated Lipids with Ester Bonds in $L_x$

Example 3.1: Nitrogen-Branched PEGylated Lipid E3-1 with Ester Bonds in $L_x$

E3-1

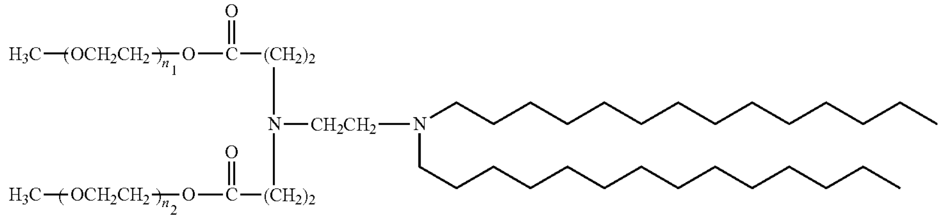

E3-1 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is —$CH_2CH_2$—, both $L_x$ are —C(═O)$CH_2CH_2$—, and T is a methyl group. The molecular weight of each PEG chain is approximately 1 kDa, corresponding to $n_1 \approx n_2 \approx 22$.

The preparation method is as follows:

Referring to the reaction conditions and feeding ratios in the Steps c-d of Example 1.1, S1-3 (3.26 g, 7.2 mmol) underwent two alkylation reactions with the linear polyethylene glycol-methyl sulfonate derivative S3-1 containing an ester bond ($M_n \approx 1.2$ kDa, $n_1 \approx 22$, PDI=1.01, 1.2 mmol for the first alkylation, 0.8 mmol for the second alkylation). After purification with column chromatography, the nitrogen-branched PEGylated lipid E3-1 (0.55 g) was obtained. $^1H$ NMR (400 MHz, $CDCl_3$) δ: 4.26-4.05 (m, 4H, —$OCH_2CH_2OC$(═O)—), 3.75-3.42 (m, PEG; 4H, —$OCH_2CH_2OC$(═O)—), 3.36 (s, 6H, —$OCH_3$), 2.78-2.35 (m, 8H, —OC(═O)$CH_2CH_2$N< 4H, >N$(CH_2)_2$N<; 4H, —N[$CH_2(CH_2)_2$-]$_2$), 1.49-1.01 (m, 44H, —$CH_2CH_2CH_2$—; 4H, —$CH_2CH_3$), 0.85 (t, 6H, —$CH_2CH_3$). The molecular weight determined by GPC was approximately 2.6 kDa, PDI=1.02.

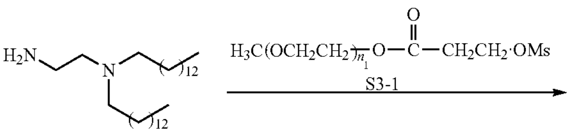

S1-3

E3-1

Example 3.2: Nitrogen-Branched PEGylated Lipid E3-2 with Ester Bonds in $L_x$

E3-2

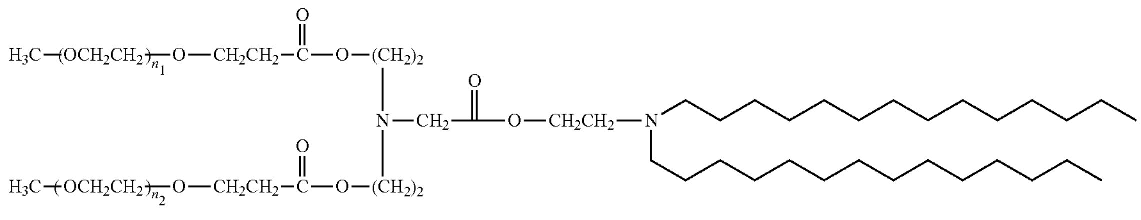

E3-2 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is —$CH_2CH_2C$(═O)$OCH_2CH_2$—, both $L_x$ are —$CH_2CH_2C$(═O)$OCH_2CH_2$—, and T is a methyl group. The molecular weight of each PEG chain is approximately 1 kDa, corresponding to $n_1 \approx n_2 \approx 22$.

The preparation method is as follows:

Step a: Under argon atmosphere, the N,N-dihydroxyethylglycine derivative containing two TBS-protected hydroxyl groups (S3-3, 0.78 g, 2.0 mmol), the lipid compound containing a free hydroxyl group S2-3 (1.09 g, 2.4 mmol), and DMAP (61 mg, 0.5 mmol) were successively dissolved in dichloromethane (12 mL), and then DCC (0.62 g, 3.0 mmol) was added. The reaction proceeded at room temperature for 16 h. After the reaction was over, the precipitates were removed by filtration. The filtrate was concentrated, and then added with 8 mL tetrahydrofuran (THF) and further with the 1M solution of TBAF/THF (8 mL). The deprotection reaction was continued overnight to remove TBS. After the reaction was over, the reaction solution was concentrated and extracted. The organic phases were combined, dried over anhydrous sodium sulfate, filtered, concentrated, and purified by column chromatography to obtain the lipid compound S3-4 containing two free hydroxyl groups (0.83 g).

Step b: Under argon atmosphere, S3-5 (5.50 g, 5.0 mmol, $M_n$≈1.1 kDa, $n_1$≈22, PDI=1.01), S3-4 (0.60 g, 1.0 mmol), and DMAP (0.15 g, 1.3 mmol) were successively dissolved in dichloromethane (30 mL), and then DCC (1.55 g, 7.5 mmol) was added. The reaction proceeded at room temperature for 16 h. After the reaction was over, the precipitates were removed by filtration. The filtrate was concentrated and purified by column chromatography to obtain the nitrogen-branched PEGylated lipid E3-2 (0.59 g). $^1H$ NMR (400 MHz, $CDCl_3$) δ: 4.25-4.09 (m, 4H, $—OCH_2CH_2C(═O)O—$), 4.07 (t, 2H, $—C(═O)OCH_2CH_2N<$), 3.76-3.40 (m, PEG; 4H, $—OCH_2CH_2C(═O)O—$), 3.36 (s, 6H, $—OCH_3$), 3.32 (s, 2H, $>NCH_2C(═O)O—$), 3.22-2.36 (m, 4H, $—OCH_2CH_2C(═O)N<$; 2H, $—C(═O)OCH_2CH_2N<$; 4H, $—OCH_2CH_2C(═O)O—$; 4H, $—N[CH_2(CH_2)_2\text{-}]_2$), 1.49-1.03 (m, 44H, $—CH_2CH_2CH_2—$; 4H, $—CH_2CH_3$), 0.88 (t, 6H, $—CH_2CH_3$).

The molecular weight determined by GPC was approximately 2.7 kDa, PDI=1.02.

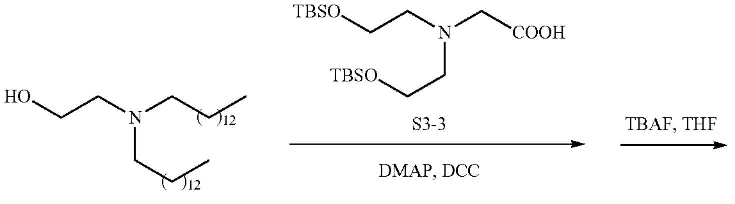

S2-3

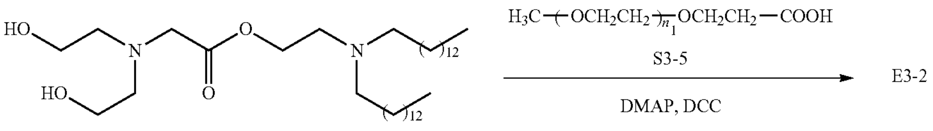

Example 4: Nitrogen-Branched PEGylated Lipid Containing a 1,4,7-Triazacyclononane Branching Core (E4-1)

E4-1

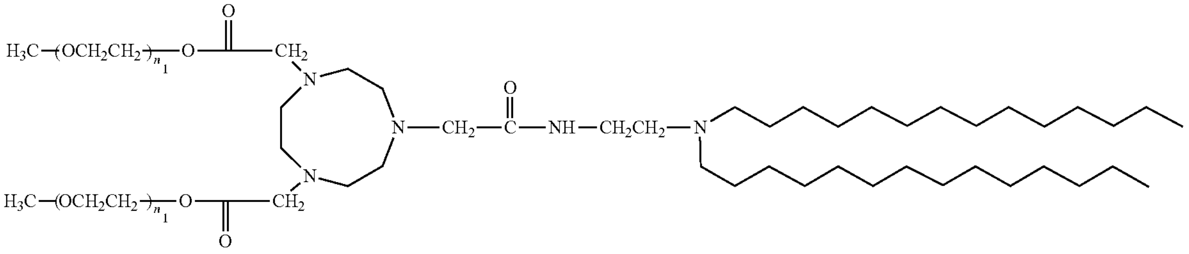

E4-1 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is $—CH_2C(=O)NHCH_2CH_2—$, $N_{core}$ is

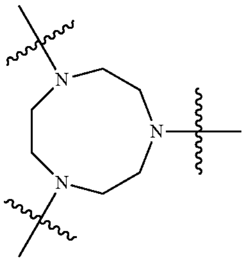

, both L, are $—C(=O)CH_2—$, and T is a methyl group. The molecular weight of each PEG chain is approximately 1 kDa, corresponding to $n_1≈n_2≈22$.

The preparation method is as follows:

Step a: In 15 mL anhydrous dichloromethane was dissolved NOTA-bis(t-Bu ester) (S4-1, 0.83 g, 2.0 mmol), and then NHS (0.35 g, 3.0 mmol) and DCC (0.62 g, 3.0 mmol) were successively added. Into the solution of S1-3 (1.09 g, 2.4 mmol) in 15 mL dichloromethane was added DMAP (49 mg, 0.4 mmol). The aforementioned two solutions were mixed and reacted for 24 hours at room temperature while stirring. After the reaction was over, the precipitates were removed by filtration. The filtrate was concentrated, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain S4-2 (1.26 g).

Step b: Under argon atmosphere, S4-2 (0.74 g, 1.0 mmol), methoxypolyethylene glycol S4-3 (3.00 g, 3.0 mmol, $M_n≈1.0$ kDa, $n_1≈22$, PDI=1.01), and DMAP (61 mg, 0.5 mmol) were successively dissolved in dichloromethane (20 mL), and then DCC (0.62 g, 3.0 mmol) was added. The reaction proceeded at room temperature for 16 h. After the reaction was over, the precipitates were removed by filtration. The filtrate was concentrated and purified by column chromatography to obtain the nitrogen-branched PEGylated lipid E4-1 (0.74 g). $^1H$ NMR (400 MHz, $CDCl_3$) δ: 4.18-4.08 (m, 4H, $—OCH_2CH_2OC(=O)—$), 3.74-3.31 (m, PEG; 4H, $—OCH_2CH_2OC(=O)—$; 6H, $—OCH_3$), 3.26-2.69 (m, 2H, $—C(=O)NHCH_2CH_2N<$; 4H, $—OC(=O)CH_2N<$; 2H, $>NCH_2C(=O)NH—$; 4H, $—N[CH_2(CH_2)_2-]_2$; 12H, $>N(CH_2)_2N<$), 1.46-1.01 (m, 44H, $—CH_2CH_2CH_2—$; 4H, $—CH_2CH_3$), 0.85 (t, 6H, $—CH_2CH_3$). The molecular weight determined by GPC was approximately 2.7 kDa, PDI=1.01,

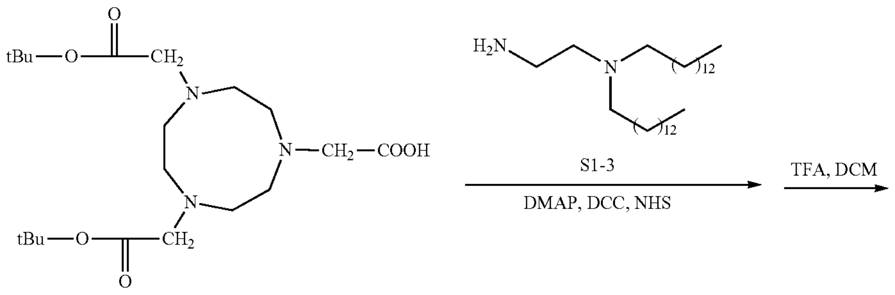

S4-1

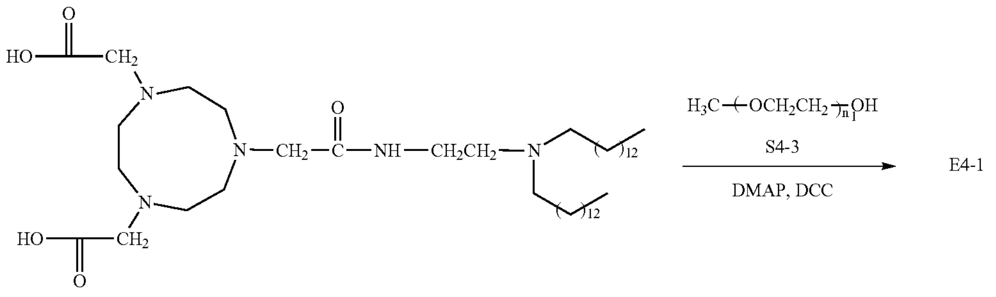

S4-2

Example 5: Nitrogen-Branched PEGylated Lipid Containing a Carbazole Branching

E5-1

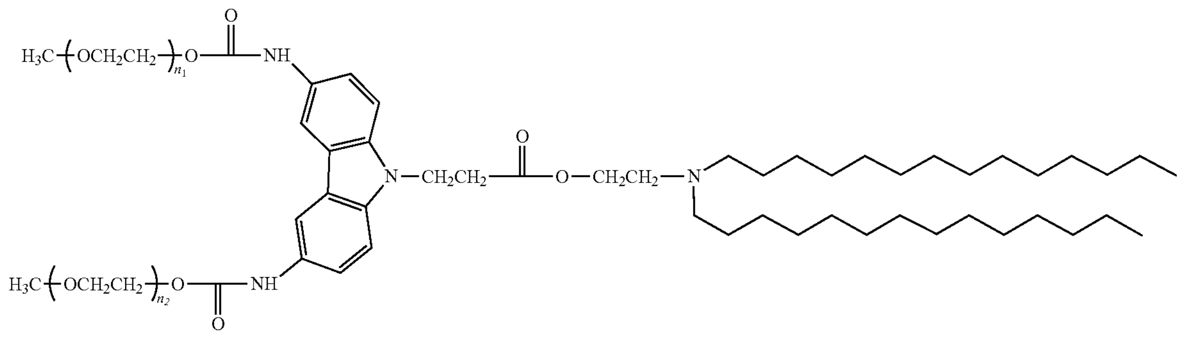

E5-1 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is $-CH_2CH_2C(=O)OCH_2CH_2-$, $N_{core}$ is

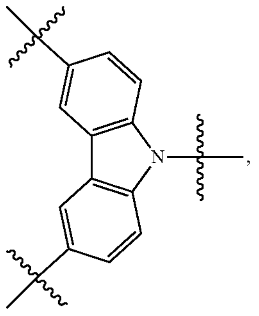

both $L_x$ are $-C(=O)NH-$, and T is a methyl group. The molecular weight of each PEG chain is approximately 1 kDa, corresponding to $n_1 \approx n_2 \approx 22$.

The preparation method is as follows:

Step a: The carbazole derivative containing two Cbz-protected amino groups S5-2 (1.86 g, 4.0 mmol) was dissolved with dried THE (30 mL), slowly added with NaH (60%, 1.60 g, 40.0 mmol) in an ice bath, and reacted for 1 h in an ice bath. After the reaction was over, S5-1 (1.08 g, 4.8 mmol, wherein S5-1 was a sulfonate compound obtained via the reaction of 3-hydroxypropionic acid and methanesulfonyl chloride) was added, and the reaction was continued for 1 h while stirring in an ice bath, after which the reaction solution was slowly returned to room temperature and the reaction was continued overnight. After the reaction was over, the reaction was placed in an ice bath, and then 0.5 mL water was added slowly to quench the reaction. After stirring for 30 minutes, the solvent was removed via rotary evaporation, and water (30 mL) was added and mixed while stirring. Then, extraction was performed twice using dichloromethane (15 mL*2). The dichloromethane organic phases were combined and washed with a saturated solution of sodium chloride (15 mL*2). The organic phase was concentrated under reduced pressure, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain S5-3 (1.67 g).

Step b: Under argon atmosphere, S5-3 (1.08 g, 2.0 mmol), S2-3 (1.09 g, 2.4 mmol), and DMAP (61 mg, 0.5 mmol) were successively dissolved in dichloromethane (15 mL), and then DCC (0.62 g, 3.0 mmol) was added. The reaction proceeded at room temperature for 16 h. After the reaction was over, the precipitates were removed by filtration. The filtrate was concentrated, redissolved with methanol, added with 10% Pd/C catalyst, and reacted for 14 h at room temperature while stirring and bubbling hydrogen gas. After the reaction was over, the catalyst was removed by filtration through celite. The reaction solution was concentrated and purified by column chromatography to obtain the lipid compound S5-4 (1.20 g).

Step c: The methoxypolyethylene glycol-succinimide carbonate mPEG-SC (S13-4, 3.30 g, 3.0 mmol, $M_n \approx 1.1$ kDa, $n_1 \approx 22$, PDI=1.01) was dissolved with 50 mL anhydrous dichloromethane, added with DMAP (61 mg, 0.5 mmol), stirred and mixed, and then slowly added with the solution of S5-4 (0.71 g, 1.0 mmol) in anhydrous dichloromethane in an ice bath, mixed, and reacted for 16 h at 25° C. while stirring. After the reaction was over, the reaction solution was washed with sodium bicarbonate solution, 3M sodium hydroxide solution and saturated brine. The organic phase was concentrated and purified by column chromatography to obtain the nitrogen-branched PEGylated lipid E5-1 (1.21 g). $^1H$ NMR (400 MHz, $CDCl_3$) δ: 8.22 (s, 2H, carbazolyl), 7.49-7.41 (m, 4H, carbazolyl), 4.61 (t, 2H, $>NCH_2CH_2C(=O)O-$), 4.24-4.20 (m, 4H, $-OCH_2CH_2OC(=O)NH-$), 4.08 (t, 2H, $-C(=O)OCH_2CH_2N<$), 3.77-3.40 (m, PEG; 4H, $-OCH_2CH_2OC(=O)NH-$), 3.37 (s, 6H, $-OCH_3$), 3.19-2.96 (m, 2H, $-C(=O)OCH_2CH_2N<$; 4H, $-N[CH_2(CH_2)_2\text{-}]_2$), 2.83 (t, 2H, $>NCH_2CH_2C(=O)O-$), 1.49-1.06 (m, 44H, $-CH_2CH_2CH_2-$; 4H, $-CH_2CH_3$), 0.84 (t, 6H, $-CH_2CH_3$). The molecular weight determined by GPC was approximately 2.8 kDa, PDI=1.01.

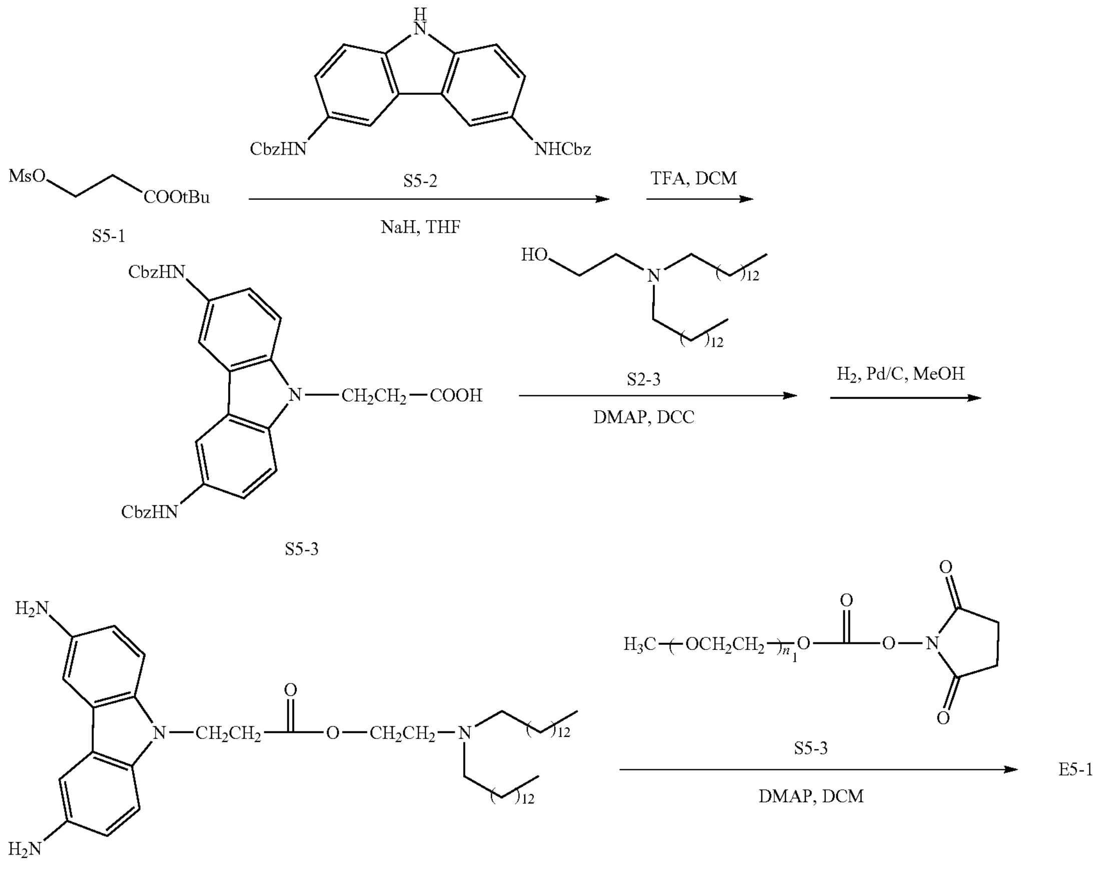

Example 6: Nitrogen-Branched PEGylated Lipids with Peptide Bonds in $L_d$

Example 6.1: Nitrogen-Branched PEGylated Lipid E6-1 with a Glycine-Glycine Peptide Bond in $L_d$ The preparation method is as follows:

Step a: Under argon atmosphere, the glycine dipeptide derivative containing a Boc-protected amino group (S6-1, 1.39 g, 6.0 mmol), the lipid compound S2-3 containing a

E6-1

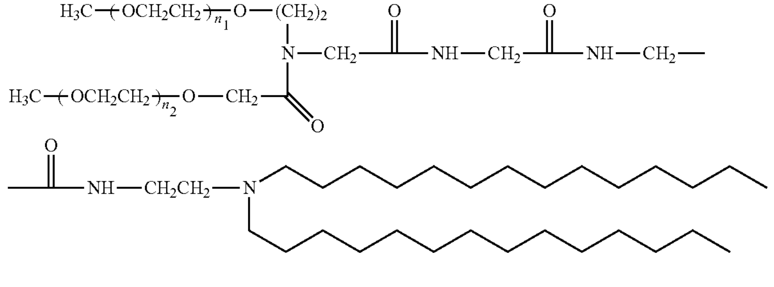

E6-1 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is $—CH_2C(=O)$-Gly-Gly-$OCH_2CH_2—$, wherein Gly is the glycine residue $—NHCH_2C(=O)—$, $N_{core}$ is a trivalent nitrogen atomic core, two $L_x$ are respectively $—CH_2CH_2—$ and $—CH_2C(=O)—$, and T is a methyl group. The molecular weight of each PEG chain is approximately 1 kDa, corresponding to $n_1 \approx n_2 \approx 22$.

free hydroxyl group (2.18 g, 4.8 mmol), and DMAP (0.18 g, 1.5 mmol) were successively dissolved in dichloromethane (30 mL), and then DCC (1.85 g, 9.0 mmol) was added. The reaction proceeded at room temperature for 16 h. After the reaction was over, the precipitates were removed by filtration. The filtrate was concentrated, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain the lipid compound S6-2 containing a free amino group (2.37 g).

Step b: Under argon atmosphere, S2-1 (2.10 g, 1.0 mmol, $M_n$≈2.1 kDa, $n_1$≈$n_2$≈22, PDI=1.01), S6-2 (1.70 g, 3.0 mmol), and DMAP (31 mg, 0.3 mmol) were successively dissolved in dichloromethane (30 mL), and then DCC (0.31 g, 1.5 mmol) was added. The reaction proceeded at room temperature for 16 h. After the reaction was over, the precipitates were removed by filtration. The filtrate was concentrated and purified by column chromatography to obtain the nitrogen-branched PEGylated lipid E6-1 (1.32 g). $^1H$ NMR (400 MHz, $CDCl_3$) δ: 4.16 (s, 1H, —$OCH_aH_bC$(═O)N<), 4.11 (s, 1H, —$OCH_aH_bC$(═O)N<), 4.06 (t, 2H, —C(═O)$OCH_2CH_2N$<), 3.97 (s, 2H, —C(═O)$NHCH_2C$(═O)O—), 3.74-3.29 (m, PEG; 4H, —$OCH_2CH_2N$<; 6H, —$OCH_3$; 2H, >$NCH_2C$(═O)NH—; 2H, —C(═O)$NHCH_2C$(═O)NH—), 3.19-2.86 (m, 2H, —C(═O)$OCH_2CH_2N$<; 4H, —N[$CH_2(CH_2)_2$-]$_2$), 1.49-0.99 (m, 44H, —$CH_2CH_2CH_2$—; 4H, —$CH_2CH_3$), 0.84 (t, 6H, —$CH_2CH_3$). The molecular weight determined by GPC was approximately 2.7 kDa, PDI=1.01.

E6-2 corresponds to the general formula (2); wherein, $B_1$ is a pentylene group, $B_2$ is a heptylene group, $L_1$ and $L_2$ are both ester groups —C(═O)O—, $R_1$ is an undecyl group, $R_2$ is

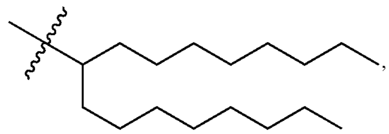

$L_d$ is —$CH_2C$(═O)-Phe-Gly-$OCH_2CH_2$—, wherein Phe is the phenylalanine residue and Gly is the glycine residue, $N_{core}$ is a trivalent nitrogen atomic core, two $L_x$ are respectively —$CH_2CH_2$— and —$CH_2C$(═O)—, and T is a methyl group. The molecular weight of each PEG chain is approximately 1 kDa, corresponding to $n_1$≈$n_2$≈22.

The preparation method is as follows:

Step a: Under argon atmosphere, the phenylalanine-glycine dipeptide derivative containing a Boc-protected amino group (S6-3, 1.93 g, 6.0 mmol), the lipid compound S6-4 (3.41 g, 4.8 mmol, synthesized using S2-2, S1-14 and S1-12 as starting materials, referring to the preparation method in Example 1.3), and DMAP (0.18 g, 1.5 mmol) were successively dissolved in dichloromethane (50 mL), and then DCC (1.85 g, 9.0 mmol) was added. The reaction proceeded at

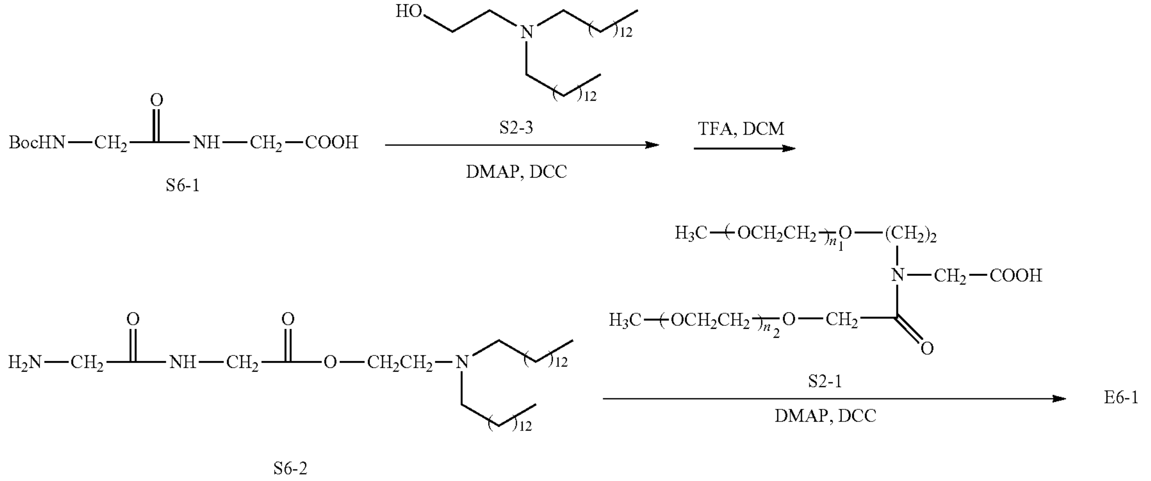

Example 6.2: Nitrogen-Branched PEGylated Lipid E6-2 with a Phenylalanine-Glycine Peptide Bond in $L_d$ room temperature for 16 h. After the reaction was over, the precipitates were removed by filtration. The filtrate was

E6-2

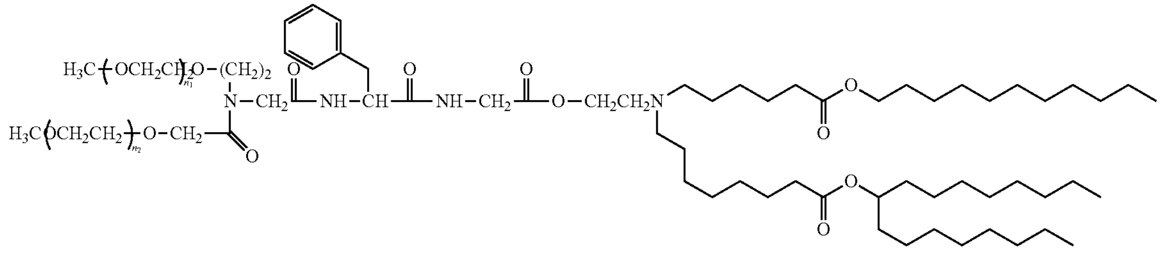

concentrated, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain the lipid compound S6-5 containing a free amino group (3.70 g).

Step b: Under argon atmosphere, S2-1 (2.10 g, 1.0 mmol, $M_n$≈2.1 kDa, $n_1$≈$n_2$≈22, PDI=1.01), S6-5 (2.74 g, 3.0 mmol), and DMAP (31 mg, 0.3 mmol) were successively dissolved in dichloromethane (50 mL), and then DCC (0.31 g, 1.5 mmol) was added. The reaction proceeded at room temperature for 16 h. After the reaction was over, the precipitates were removed by filtration. The filtrate was concentrated and purified by column chromatography to obtain the nitrogen-branched PEGylated lipid E6-2 (1.27 g). $^1$H NMR (400 MHz, $CDCl_3$) δ: 7.30-7.19 (m, 5H, Ar); 4.50-4.44 (m, 1H, Phe-α-CH<), 4.17 (s, 1H, —$OCH_aH_b$—C(═O)N<), 4.13 (s, 1H, —$OCH_aH_b$C(═O)N<), 4.09 (t, 4H, —$(CH_2)_2CH_2OC$(═O)—), 4.05 (t, 2H, —C(═O)$OCH_2CH_2N$<), 3.97 (s, 2H, —C(═O)$NHCH_2C$(═O)O—), 3.76-3.28 (m, PEG; 4H, —$OCH_2CH_2N$<; 6H, —$OCH_3$; 2H, >$NCH_2C$(═O)NH—), 3.19-2.83 (m, 2H, Phe-$CH_2$—; 2H, —C(═O)$OCH_2CH_2N$<; 4H, —[$NCH_2(CH_2)_2$-]$_2$), 2.38-2.22 (m, 1H, —OC(═O)CH<; 2H, —$(CH_2)_2CH_2C$(═O)O—), 1.73-1.16 (m, 56H, —$CH_2CH_2CH_2$—; 6H, —$CH_2CH_3$), 0.88 (t, 9H, —$CH_2CH_3$). The molecular weight determined by GPC was approximately 3.0 kDa, PDI=1.01.

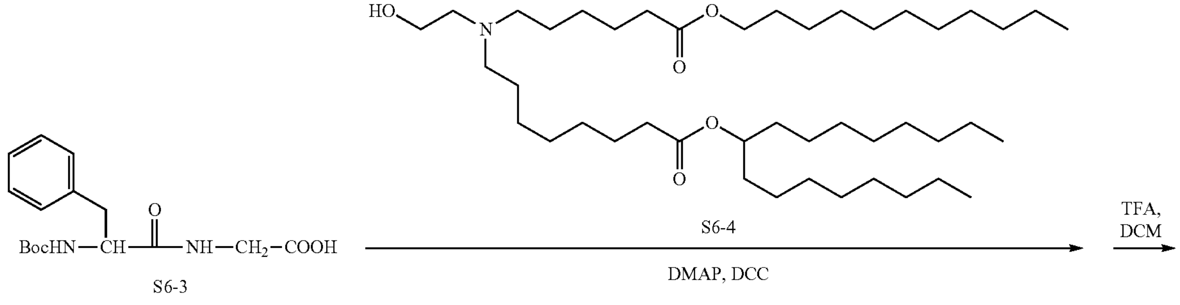

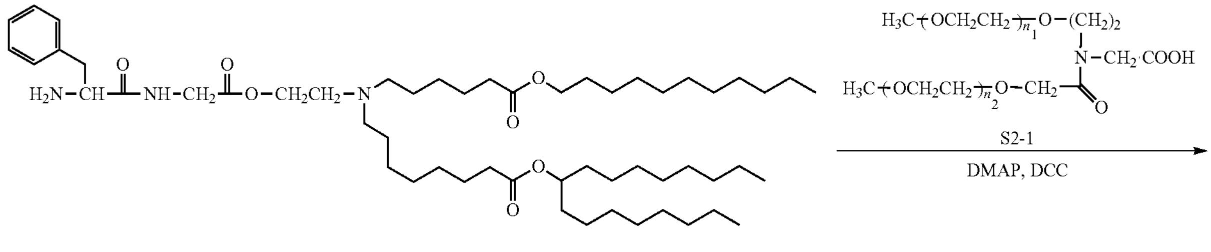

E6-2

Example 7: Nitrogen-Branched PEGylated Lipid with Ester Bonds in $L_x$, $L_1$ and $L_2$

E7-1

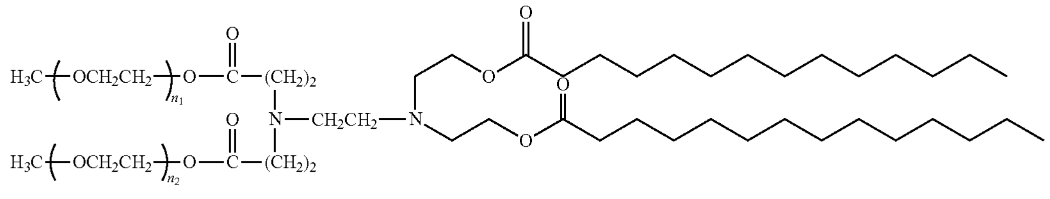

E7-1 corresponds to the general formula (2); wherein, $B_1$ and $B_2$ are both ethylene groups, $L_1$ and $L_2$ are both ester groups —OC(═O)—, $R_1$ and $R_2$ are both tridecyl groups, $L_d$ is —$CH_2CH_2$—, both $L_x$ are —C(═O)$CH_2CH_2$—, and T is a methyl group. The molecular weight of each PEG chain is approximately 1 kDa, corresponding to $n_1 \approx n_2 \approx 22$.

The preparation method is as follows:

Step a: Under argon atmosphere, S1-16 (3.42 g, 15.0 mmol), the N,N-bis(2-hydroxyethyl)ethylenediamine derivative containing a Boc-protected amino group (S7-1, 1.49 g, 6.0 mmol), and DMAP (0.46 g, 3.8 mmol) were successively dissolved in dichloromethane (60 mL), and then DCC (4.64 g, 22.5 mmol) was added. The reaction proceeded at room temperature for 16 h. After the reaction was over, the precipitates were removed by filtration. The filtrate was concentrated, deprotected with the TFA/DCM mixed solution (1:1 v/v) to remove Boc, washed with purified water, and then extracted with dichloromethane. The organic phases were combined, dried over anhydrous sodium sulfate, filtered, concentrated, and purified by column chromatography to obtain S7-2 (2.33 g).

Step b: Referring to the reaction conditions and feeding ratios in the Steps c-d of Example 1.1, S7-2 (2.05 g, 3.6 mmol) underwent two alkylation reactions with S3-1 ($M_n \approx 1.2$ kDa, $n_1 \approx 22$, PDI=1.01, 0.6 mmol for the first alkylation, 0.4 mmol for the second alkylation). After purification with column chromatography, the nitrogen-branched PEGylated lipid E7-1 (0.35 g) was obtained. $^1$H NMR (400 MHz, $CDCl_3$) δ: 4.45-4.30 (m, 4H, >$NCH_2CH_2OC$(═O)—), 4.19-4.08 (m, 4H, —$OCH_2CH_2OC$(═O)—), 3.72-3.42 (m, PEG; 4H, —$OCH_2CH_2OC$(═O)—; 4H, >$NCH_2CH_2OC$(═O)—); 3.34 (s, 6H, —$OCH_3$), 2.76-2.43 (m, 8H, —OC(═O)$(CH_2)_2$N<; 4H, >N$(CH_2)_2$N<), 2.30 (t, 4H, —OC(═O)$CH_2(CH_2)_2$—); 1.73-1.02 (m, 40H, —$CH_2CH_2CH_2$—; 4H, —$CH_2CH_3$), 0.85 (t, 6H, —$CH_2CH_3$). The molecular weight determined by GPC was approximately 2.7 kDa, PDI=1.02.

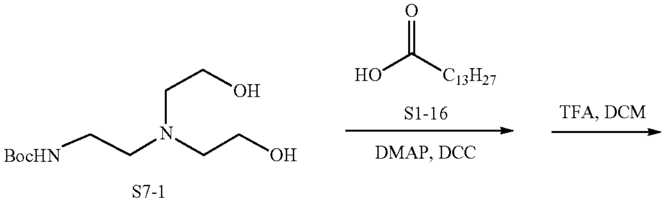

S7-1

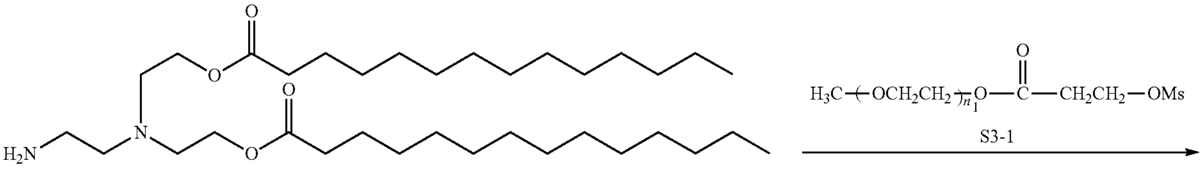

S7-2

E7-1

Example 8: Nitrogen-Branched PEGylated Lipid Coupled with Folic Acid (E8-1)

E8-1

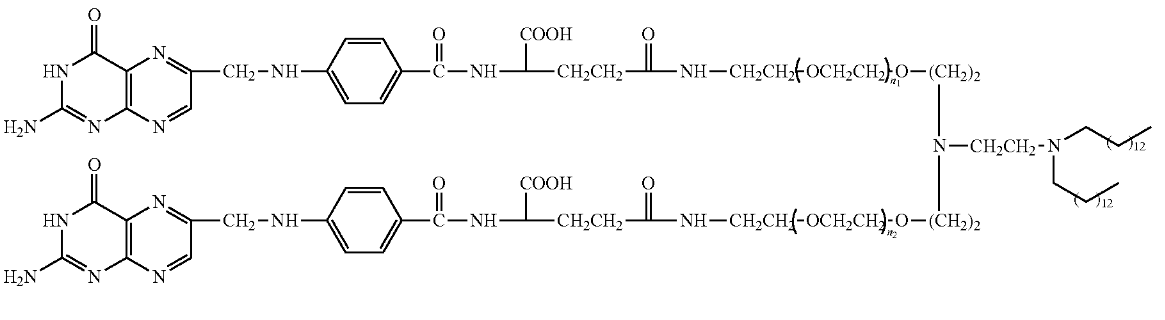

E8-1 corresponds to the general formula (2); wherein, $B_1$ and $B_2$ are both linking bonds, $L_1$ and $L_2$ are both linking bonds, $R_1$ and $R_2$ are both tetradecyl groups, $L_d$ is —$CH_2CH_2$—, both $L_x$ are —$CH_2CH_2$—, T is $R_{01}$-$L_{01}$-, $R_{01}$ is the folic acid residue, and $L_{01}$ is —$NHCH_2CH_2$—. The molecular weight of each PEG chain is approximately 1 kDa, corresponding to $n_1 \approx n_2 \approx 22$.

The preparation method is as follows:

Step a: Referring to the reaction conditions and feeding ratios in the Steps c-d of Example 1.1, S1-3 (6.52 g, 14.4 mmol) underwent two alkylation reactions with the linear bifunctional polyethylene glycol derivative S8-1 ($M_n \approx 1.3$ kDa, $n_1 \approx 22$, PDI=1.02, 2.4 mmol for the first alkylation, 1.6 mmol for the second alkylation). The TFA/DCM mixed solution (1:1 v/v) was used to remove the Boc protecting group. After purification with column chromatography, the nitrogen-branched PEGylated lipid E8-1 (1.44 g) was obtained.

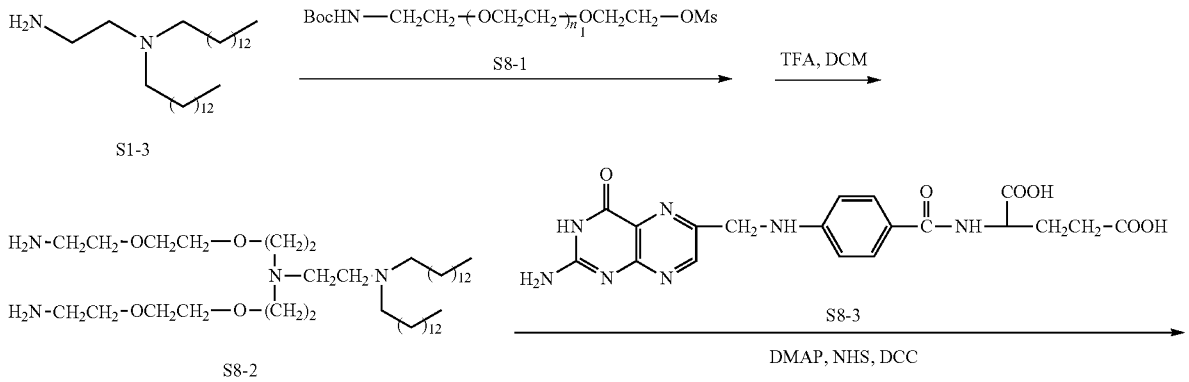

S1-3, S8-1, S8-2, S8-3, E8-1

Step b: In 15 mL anhydrous dichloromethane was dissolved folic acid (S8-3, 0.88 g, 2.0 mmol), added with NHS (0.35 g, 3.0 mmol), and then added with DCC (0.62 g, 3.0 mmol). Into the solution of S8-2 (1.04 g, 0.4 mmol, $M_n \approx 2.6$ kDa, $n_1 \approx n_2 \approx 22$, PDI=1.02) in 15 mL dichloromethane was added DMAP (49 mg, 0.4 mmol). The aforementioned two solutions were mixed and reacted for 24 hours at room temperature while stirring. After the reaction was over, the precipitates were removed by filtration. The filtrate was concentrated and purified by column chromatography to obtain E8-1 (0.41 g). $^1$H NMR (400 MHz, $CDCl_3$) δ: 8.69 (s, 2H, pterinC7), 7.65-7.62 (d, 4H, Ph), 6.65 (d, 4H, Ph), 4.48-4.45 (d, 4H, pterinC6-$CH_2$NH—), 4.33-4.21 (m, 2H, —CH(COOH)—), 3.75-3.33 (m, PEG; 4H, —$OCH_2CH_2$N<; 8H, —C(═O)NH$(CH_2)_2$O—), 2.86-2.68 (m, 4H, —$OCH_2CH_2$N<), 2.52-2.35 (m, 4H, >$NCH_2(CH_2)_2$—), 2.34-1.93 (m, 4H, —CH(COOH)$(CH_2)_2$C(═O)NH—), 1.48-1.05 (m, 44H, —$CH_2CH_2CH_2$—; 4H, —$CH_2CH_3$), 0.86 (t, 6H, —$CH_2CH_3$). The molecular weight determined by GPC was approximately 3.4 kDa, PDI=1.02.

2.2. Lipid Pharmaceutical Compositions

Example 9: Preparation of LNP-mRNA Pharmaceutical Compositions

In this embodiment, LNP-mRNA pharmaceutical compositions containing Fluc-mRNA (LNP/Fluc-mRNA) were prepared; wherein, the phospholipids contained were all DSPC, the steroid lipids contained were all cholesterol, the cationic lipids contained were all CL-1, but the PEGylated lipids contained were different; CL-1 was obtained by referring to the preparation method disclosed by CN113402405A, and its structure is as follows:

CL-1

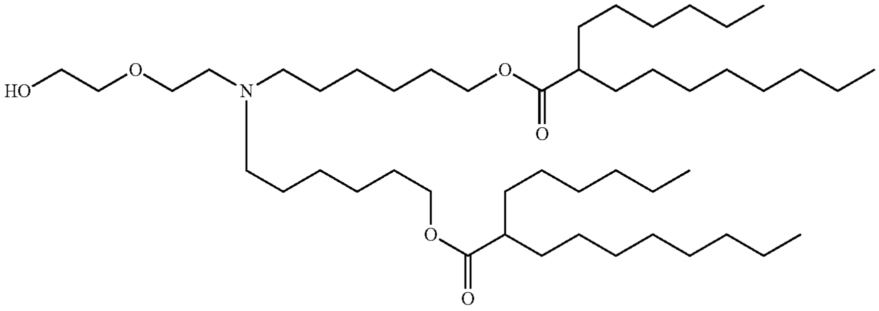

The preparation method of LNP/Fluc-mRNA is as follows:

A certain amount of stock solutions of CL-1, DSPC, cholesterol and PEGylated lipid were pipetted to be dissolved in ethanol, wherein the molar ratio of CL-1, DSPC, cholesterol and PEGylated lipid was 50:10:38:1.5, and the ethanol phase solution was obtained (specific lipid formulation of each group is illustrated in Table 1 of Example 10; the PEGylated lipid of the control group L-0 is PEG2k-DMG (abbreviated as DMG); the PEGylated lipids of the experimental groups are the non-linear PEGylated lipids of the present invention). The Fluc-mRNA was added into a 10-50 mM citrate buffer (pH=4) to obtain the aqueous phase solution. The ethanol phase solution and the aqueous phase solution were mixed (1:3 v/v) to prepare the cationic lipid nanoparticle LNP/Fluc-mRNA. The DPBS ultrafiltration was performed multiple times to wash and remove ethanol and free molecules. Finally, the solution was passed through a 0.2 m sterile filter for further use.

Following the above steps, the molar ratio of lipids was adjusted to CL-1:DSPC:cholesterol:PEGylated lipid=50:10:38:0.75, with the PEGylated lipid being E1-1. All other conditions remained unchanged to prepare the cationic lipid nanoparticle LNP/Fluc-mRNA (experimental group L1-1-half).

Following the above steps, the molar ratio of lipids was adjusted to CL-1:DSPC:cholesterol:PEGylated lipid=48:9:42:1.5, with the PEGylated lipid being E1-1. All other conditions remained unchanged to prepare the cationic lipid nanoparticle LNP/Fluc-mRNA (experimental group L1-1-d).

Example 10: Biological Assays for Lipid Pharmaceutical Compositions (1) Determination of Nanoparticle Size and Nucleic Acid Complexation Ability Determination of nucleic acid complexation ability: The gel electrophoresis experiment was carried out to examine the nucleic acid complexation ability of LNP/Fluc-mRNA. 0.8 g agarose was weighed and dissolved in 40 mL solution of TAE. The solution was heated in a microwave until the granules of agarose were completely dissolved, and then cooled. 5 μL nucleic acid dye (GelGreen) was added in the cooled agarose gel, and then the gel was added into the gel slot and dried with natural air. The mixed solution of LNP/Fluc-mRNA and 2 μL loading buffer was added into the agarose gel well, and the electrophoresis voltage was set to 90 V The electrophoresis was carried out at room temperature for 10 min. The result showed that free Fluc-mRNA hardly existed in both the experimental groups and the control group, indicating that the lipid composition containing the nitrogen-branched PEGylated lipid of the present invention has a good ability to complex with nucleic acids.

Determination of encapsulation efficiency: The LNP/Fluc-mRNA was ultracentrifuged (4° C., 60000 rpm, 1 h) with an ultracentrifuge. The concentration of unencapsulated Fluc-mRNA in the supernatant was determined by a nucleic acid quantifier. The encapsulation efficiency of LNP for Fluc-mRNA was calculated. The results are summarized in Table 1, showing that the cationic lipid nanoparticles of the present invention have higher encapsulation efficiency for nucleic acid drugs; wherein, the encapsulation efficiency of the experimental groups containing nitrogen-branched PEGylated lipids with a molecular weight of approximately 1 kDa or 2 kDa per arm are all above 87%, and meanwhile the encapsulation efficiency of the experimental group containing the nitrogen-branched PEGylated lipid with a molecular weight of approximately 0.5 kDa per arm (L1-1-500) reaches 83%. Particularly, the experimental group L1-1-half contains the nitrogen-branched PEGylated lipid E1-1 with a molecular weight of approximately 1 kDa per arm, the control group L-0 contains the linear PEGylated lipid PEG2k-DMG with a molecular weight of approximately 2 kDa, and the molar content of the PEGylated lipid E1-1 in L1-1-half is only half of that of the PEG2k-DMG in L-0; however, the encapsulation efficiency of L1-1-half is even slightly higher than that of L-0, wherein the former is 93.3% and the latter is 92.3%, indicating that even in a circumstance where the nitrogen-branched PEGylated lipid of the present invention is used in a smaller amount, the encapsulation efficiency of LNP for Fluc-mRNA is not significantly affected.

Determination of particle size: According to the literature (Hassett et al., *J. Controlled Release* 2021, 335, 237-246), an LNP formulation loaded with nucleic acid drugs can exhibit better pharmaceutical efficacy when its particle size is in the range of 60~150 nm. In this embodiment, the particle size of LNP/Fluc-mRNA was determined by dynamic light scattering (DLS). The measured sizes of LNP/Fluc-mRNA were relatively uniform, and the PDJ values were all smaller than 0.3. The results showed that the particle sizes of LNP/Fluc-mRNA prepared with the nitrogen-branched PEGylated lipids of the present invention were ranging from approximately 65 nm to approximately 112 nm, which were all within the range of the particle size that can achieve better pharmaceutical efficacy.

TABLE 1

Determination of Particle Size and Encapsulation Efficiency

| LNP | L-0 | L1-1 | L1-1-2k | L1-1-500 |
|---|---|---|---|---|
| PEGylated Lipid | PEG2k-DMG | E1-1 | E1-1-2k | E1-1-500 |
| Encapsulation Efficiency/% | 92.3 | 96.7 | 95.2 | 83.1 |
| Particle Size/nm | 97 | 87 | 112 | 65 |

| LNP | L1-2 | L1-3 | L1-4 | L1-5 |
|---|---|---|---|---|
| PEGylated Lipid | E1-2 | E1-3 | E1-4 | E1-5 |
| Encapsulation Efficiency/% | 93.4 | 91.8 | 87.8 | 88.8 |
| Particle Size/nm | 99 | 92 | 75 | 79 |

| LNP | L2-1 | L2-2 | L2-3 | L2-4 |
|---|---|---|---|---|
| PEGylated Lipid | E2-1 | E2-2 | E2-3 | E2-4 |
| Encapsulation Efficiency/% | 96.9 | 87.3 | 92.9 | 90.5 |
| Particle Size/nm | 101 | 86 | 93 | 84 |

| LNP | L2-5 | L2-6 | L2-7 | L3-1 |
|---|---|---|---|---|
| PEGylated Lipid | E2-5 | E2-6 | E2-7 | E3-1 |
| Encapsulation Efficiency/% | 94.7 | 97.3 | 92.3 | 96.2 |
| Particle Size/nm | 95 | 90 | 99 | 75 |

| LNP | L3-2 | L4-1 | L5-1 | L6-1 |
|---|---|---|---|---|
| PEGylated Lipid | E3-2 | E4-1 | E5-1 | E6-1 |
| Encapsulation Efficiency/% | 89.1 | 87.7 | 95.1 | 93.6 |
| Particle Size/nm | 94 | 91 | 85 | 84 |

| LNP | L6-2 | L7-1 | L8-1 | L1-1-half |
|---|---|---|---|---|
| PEGylated Lipid | E6-2 | E7-1 | E8-1 | E1-1 |
| Encapsulation Efficiency/% | 98.2 | 99.1 | 93.5 | 93.3 |
| Particle Size/nm | 88 | 88 | 82 | 80 |

| LNP | L1-1-d |
|---|---|
| PEGylated Lipid | E1-1 |
| Encapsulation Efficiency/% | 94.9 |
| Particle Size/nm | 85 |

(2) Evaluation of Stability in Serum

Cationic lipids play an important role in the LNP for delivering nucleic acid drugs. During the delivery process in the systemic circulation, there exist amounts of negatively charged serum proteins that are easily adsorbed to positively charged cationic lipid nanoparticles to form large-sized aggregates which can be cleared by the mononuclear phagocytic system, therefore causing a lower genetic transfection efficiency of LNP. The nitrogen-branched PEGylated lipid of the present invention can bring the "stealth effect" to LNP.

The aforementioned LNP/Fluc-mRNA (1 control group L-0 and 24 experimental groups L1-1~L1-1-d) were respectively added to the culture media containing 10% fetal bovine serum (FBS), stirred at 37° C., and sampled at a regular interval to determine the change of particle size of LNP/Fluc-mRNA to analyze the stability of nucleic acid pharmaceutical formulation in serum. The results showed that, in 7 days, the experimental group L1-1-500 had a relatively large change (9%) in particle size, wherein the molecular weight of the polyethylene glycol component was approximately 0.5 kDa for each arm; all the rest experimental groups and the control group had the changes in particle size smaller than 6%; particularly, the change of particle size of L1-1-half was approximately 5% which was not significantly different from those of L-0 and L1-1 (approximately 4% and 2%, respectively), while the amount of PEGylated lipid used in L1-1-half was only half of that of L-0 or L1-1. These results indicate that the LNP-nucleic acid pharmaceutical compositions prepared with the nitrogen-branched PEGylated lipids of the present invention, with a molecular weight of approximately 1 kDa per arm of polyethylene glycol, have good stability in serum; when the molecular weight of PEGylated lipid is close to one another, e.g., both the linear PEGylated lipid DMG in L-0 and the non-linear nitrogen-branched PEGylated lipid E1-1 in L1-1 have the molecular weight of PEG component of approximately 2 kDa, the non-linear structure E1-1 can achieve better stability of lipid pharmaceutical composition in serum; even when used in a smaller amount, the non-linear PEGylated lipids can still achieve relatively good stability of lipid pharmaceutical composition in serum.

(3) Evaluation of Cytotoxicity

The cells used were HeLa cells, and the method used was to measure cell viability by CCK-8 kit.

The commercial transfection reagent Lipofectamine 2000 (L2K) was used to prepare the L2K/Fluc-mRNA complex according to the method in Example 9.

HeLa cells were inoculated onto a 96-well plate at 6,000 cells/well, 100 μL per well, and then divided into the control group (blank control group), the L2K/Fluc-mRNA group (positive control group) and the LNP/Fluc-mRNA groups (experimental groups L1-1-L7-1), and then incubated at 37° C., 5% $CO_2$. After 24 hours of cell incubation, into the blank control group was added 10 μL PBS solution, into the positive control group and the experimental groups were added 3.3 g/mL L2K/Fluc-mRNA (10 μL) and 3.3 g/mL LNP/Fluc-mRNA (10 μL), respectively, and the incubation was continued at 37° C., 5% $CO_2$. After another 24 hours of incubation, the 96-well plate was retrieved while protected from light. The culture medium was aspirated, and then a diluted solution of CCK-8 was added 120 μL per well. Then, the incubation was continued for 1-4 hours at 37° C., 5% $CO_2$.

The 96-well plate was retrieved, and a microplate reader was used to measure the absorbance of each well at a wavelength of 450 nm.

The results of three repeated assays were averaged, and showed that the cell viability of the positive control group L2K/Fluc-mRNA was 92%, those of the experimental groups were all above 88%, and particularly, those of L1-1, L1-4, L1-5, L2-1, L2-4, L2-7, 7-1 were 97% or higher.

These results indicate that, compared with the L2K/Fluc-mRNA which contains the commercial transfection reagent Lipofectamine 2000, the LNP/Fluc-mRNA of the present invention also has no obvious cytotoxicity toward HeLa cells.

TABLE 2

Results of Cell Transfection Assays

| No. | Relative Value of Fluorescence Intensity | No. | Relative Value of Fluorescence Intensity | No. | Relative Value of Fluorescence Intensity |
|---|---|---|---|---|---|
| Blank | 1 | L1-1 | 7.3 | L2-1 | 7.5 |
| L-0 | 8.0 | L1-2 | 9.3 | L2-2 | 9.0 |
| | | L1-3 | 8.8 | L2-3 | 9.8 |
| | | L1-4 | 7.8 | L2-4 | 7.0 |
| | | L1-5 | 8.3 | L2-5 | 9.8 |
| | | L3-1 | 8.8 | L2-6 | 9.5 |
| | | L3-2 | 9.5 | L2-7 | 7.3 |
| | | L4-1 | 7.8 | L6-1 | 11.0 |
| | | L5-1 | 8.5 | L6-2 | 10.3 |
| | | | | L7-1 | 10.8 |

(4) Evaluation of Transfection Efficiency

In order to examine the transfection efficiency of mRNA at cell level for each group of LNP/Fluc-mRNA composition prepared in Example 9, assays were performed on the basis of luciferase bioluminescence. The formulation of LNP/Fluc-mRNA composition was dissolved in the culture medium to the required dose, and HeLa cells, as a cell model, were inoculated at a density of 6,000 cells/well. The cell suspension was inoculated at 100 μL/well onto a 96-well black frame plate with clear wells. After the inoculation, the cells were incubated for 24 h in a cell culture incubator. Then, a dose of 0.2 ug mRNA per well was given, while the blank control group was added with free Fluc-mRNA of the corresponding dose. After 24 hours of transfection, the old culture medium was removed and replaced with a new medium containing the D-fluorescein sodium substrate (1.5 mg/mL). After 5 minutes of incubation, bioluminescence was detected using a microplate reader. Stronger fluorescence meant more Fluc-mRNA were transported into the cytoplasm and translated into the corresponding fluorescent protein. The results are shown in Table 2, wherein, the relative value of fluorescence intensity is the ratio of the fluorescence intensity of each group to that of the blank control group. The results indicate that the LNP/Fluc-mRNA compositions prepared in the present invention all have excellent transfection efficiency in vitro, i.e., the LNPs of the control group and the experimental groups are all effective carriers for delivery, and most of the experimental groups featuring a degradable linking group in the PEGylated lipid have higher transfection efficiency than the control group. Particularly, L6-1 and L6-2 featuring an oligopeptide residue in the linking group located in between the PEGylated component and the lipid component as well as L7-1 featuring ester groups in all of $L_x$, $L_1$ and $L_2$ all have significantly higher transfection efficiency than L-0 which employs DMG as the PEGylated lipid.

The results show that the LNP containing the nitrogen-branched PEGylated lipid of the present invention enables an effective delivery of Fluc-mRNA to cells as well as the transfection afterwards. The nitrogen-branched PEGylated lipid of the present invention having a group degradable in cells is more helpful for the lipid-nucleic acid pharmaceutical composition to exhibit better efficacy after the cellular uptake.

(5) Evaluation of Targeting Ability

This embodiment examines the targeting ability of the LNP containing E8-1 which is modified by folic acid at the ends of polyethylene glycol, and compares it with E1-1, a structure most similar in structure except for the ends of PEG I. Preparation of the formulation of nitrogen-branched PEGylated lipid nanoparticle/oxaliplatin composition:

Step a: DSPC (4 g) and cholesterol (667 mg) were dissolved in 60 mL dichloromethane, added with 20 mL aqueous solution of 80 mg oxaliplatin, stirred for 30 min, and ultrasonicated for 20 min. The organic solvent was removed by rotary evaporation at 40° C. After the gel was collapsed, components including E1-1 (0.50 g, 0.2 mmol) and 50 mL aqueous solution of poloxamer F68 (400 mg) were added respectively. The evaporation was continued for 30 min, followed by high-pressure homogenization at 400 bar for 5 min. The volume was adjusted to 100 mL with water, and then the tangential flow ultrafiltration was used to isolate oxaliplatin. A tangential-flow membrane pack with a molecular weight cut-off of 10 kDa was used for the ultrafiltration. The ultrafiltration was performed repeatedly for 3 times, using water as the displacement liquid. The ultrafiltration centrifuge tube was used to measure the encapsulation efficiency, and the high performance liquid chromatography was used to measure the final concentration of drug. The encapsulation efficiency was 95.33%. The particle size was 124 nm. The concentration of drug in the LNP suspension was adjusted to 500 g/mL with water, therefore obtaining the formulation of nitrogen-branched PEGylated lipid nanoparticle/oxaliplatin composition, LP-1.

Step b: Using the same preparation method as that of the abovementioned experimental group, E8-1 (0.68 g, 0.2 mmol) was used to replace E1-1 in the preparation to obtain the formulation of folic acid-coupled nitrogen-branched PEGylated lipid nanoparticle/oxaliplatin composition, LP-2.

II. The HCT-116 human colon cancer cell line was recovered and cultured, and the HCT-116 human colon cancer tumor-bearing nude mouse model was established. The nude mice were inoculated and grew naturally, and the tumor volume was measured with a vernier caliper. After the tumor grew to 50-75 $mm^3$, the mice were randomly divided into 4 groups on the basis of the tumor volume:

(1) Blank control group: 6 mice; the tumor tissue was retrieved after one administration via the tail vein with 5% dextrose injection;
(2) Control group 1: one administration with 10 mg/kg oxaliplatin injection; 12 mice;
(3) Control group 2: one administration with 10 mg/kg LP-1 formulation; 12 mice;
(4) Experimental group: one administration with 10 mg/kg LP-2 formulation; 12 mice;

wherein, the control group 1, the control group 2 and the experimental group were administered via the tail vein and sacrificed at different time points of 0.05, 0.5, 1, 1.5, 2, 2.5, 3, 3.5, 4, 6, 8, and 48 h. The tumor masses of nude mice were placed in a freezer for storage at −20° C., and then the HPLC was used to detect the concentration of drug. The results showed that, compared with the oxaliplatin injection, LP-1 did not exhibit a higher targeting ability; the targeting ability of LP-2 was significantly enhanced, and the corresponding peak concentration in plasma was significantly increased (by approximately 102%), indicating that the functional modification with targeting groups at the polyethylene glycol ends of a nitrogen-branched PEGylated lipid in the present invention can improve the targeting efficiency of lipid nanoparticles.

Those described above are only embodiments of the present invention, not limiting the patent scope of the present invention. Any transformation of equivalent structure or equivalent route based on the specification content of the present invention, directly or indirectly applied in other related arts, should be included in the protected patent scope of the present invention in the same way.

For those skilled in the art, without departing from the purpose and the scope of the present invention, and without unnecessary experimentation, the present invention can be implemented in a wider range with equivalent parameters, concentrations, and conditions. While the present invention has given particular examples, it should be understood that the present invention can be further modified. In conclusion, in accordance with the principles of the present invention, the present application is intended to cover any alterations, uses, or improvements of the present invention, including changes departing from the scope disclosed in this application but made using conventional techniques known in the art.

The invention claimed is:

1. A nitrogen-branched PEGylated lipid selected from the group consisting of the following structures:

E1-1

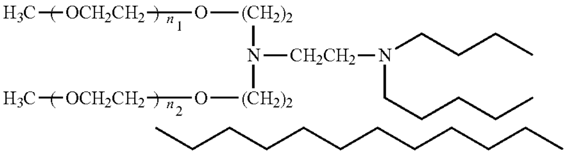

,

E1-2

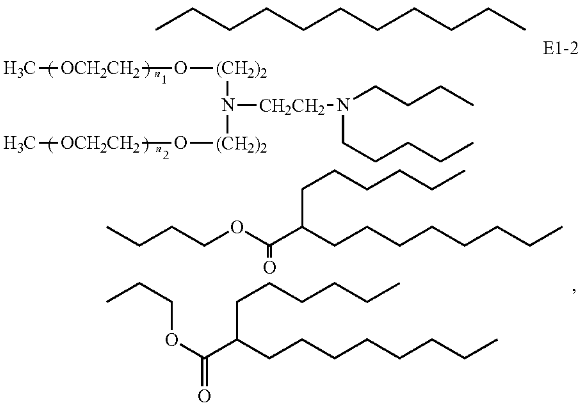

,

E1-3

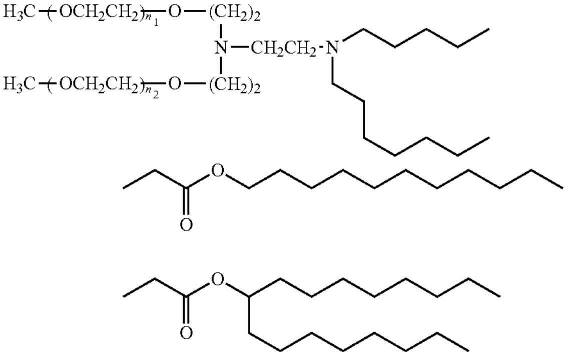

,

-continued
E1-4
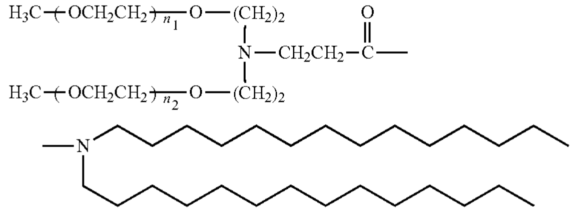
,
E1-5
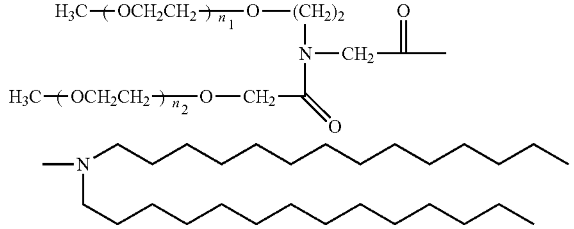
,
E2-1
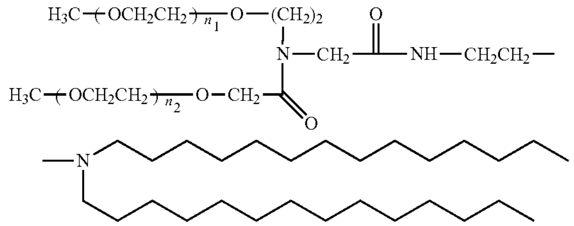
,
E2-2
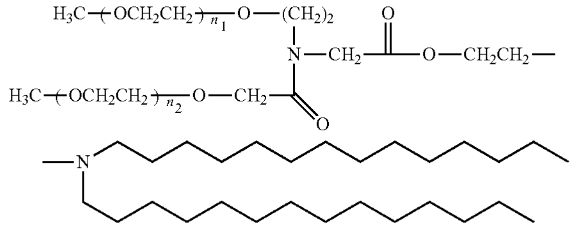
,
E2-3
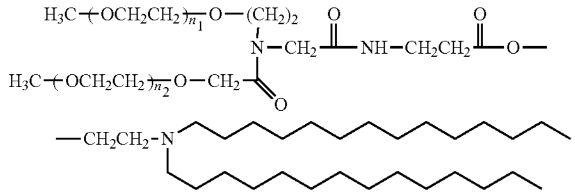
,
E2-4
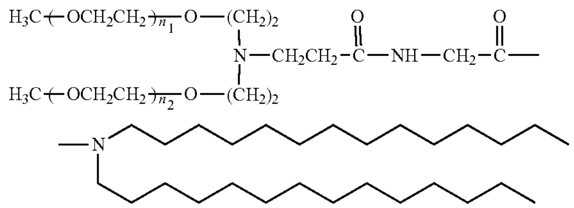
,
E2-5
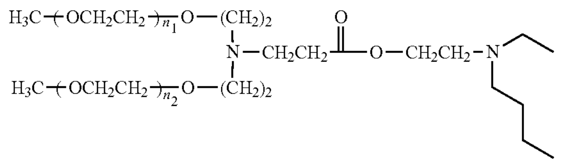
-continued
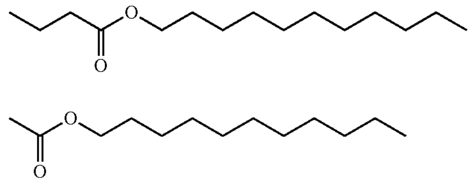
,
E2-6
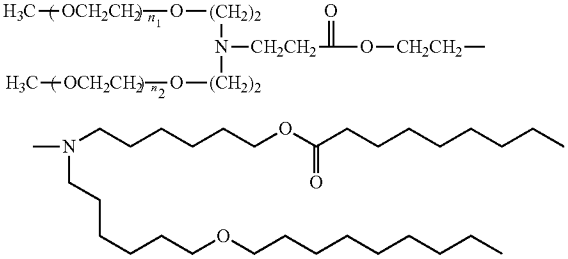
,
E2-7
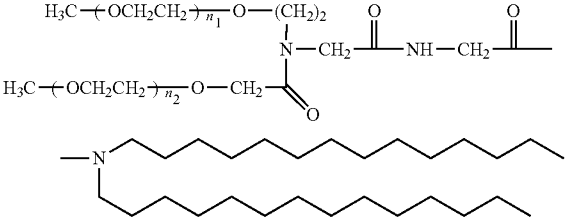
,
E3-1
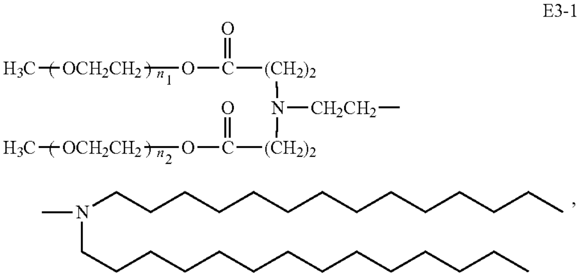
,
E3-2
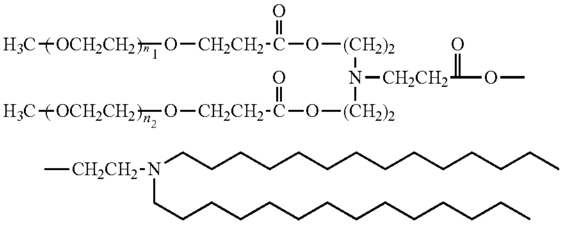
,
E4-1
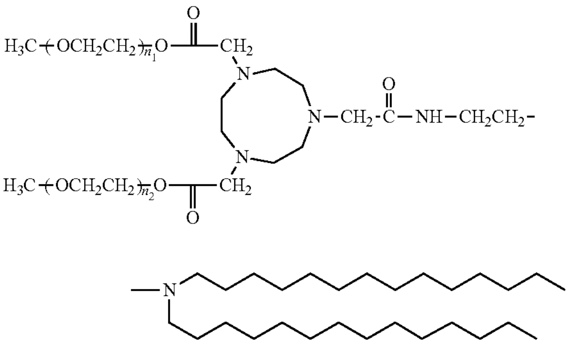
, -continued

E5-1

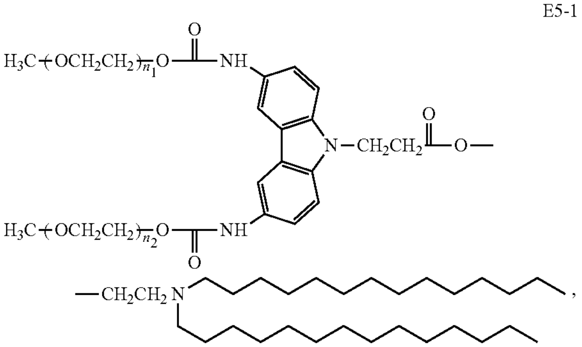

E6-1

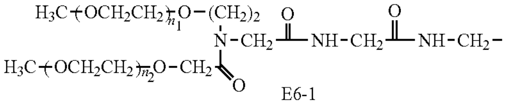

E6-1

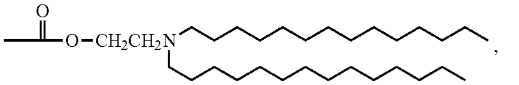

E6-2

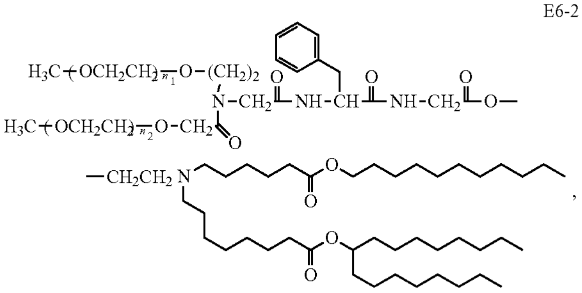

E7-1

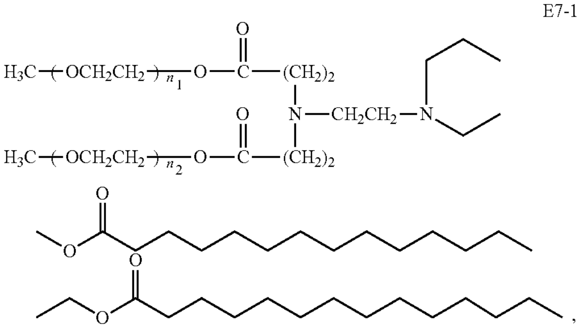

E8-1

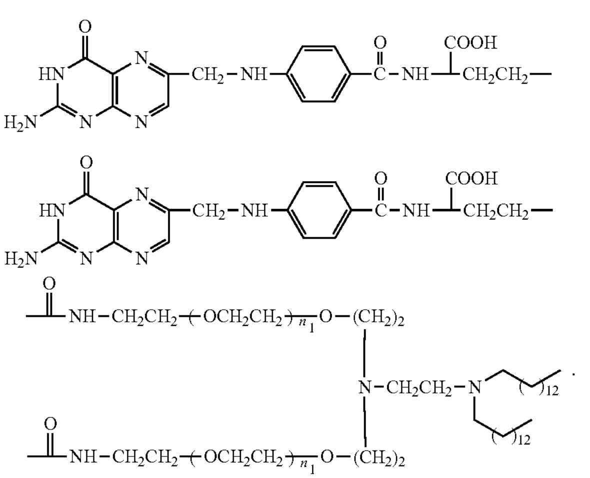

wherein $n_1$ and $n_2$ are each independently selected from integers of 4 to 100.

2. A lipid composition containing a nitrogen-branched PEGylated lipid of claim 1.

3. The lipid composition of claim 2, which contains another one or more types of lipids selected from the group consisting of phospholipid, steroid lipid, and cationic lipid, and belongs to any of the following cases:

Case (1): the lipid composition also contains a phospholipid;

Case (2): the lipid composition also contains a steroid lipid;

Case (3): the lipid composition also contains a cationic lipid;

Case (4): the lipid composition also contains a phospholipid and a steroid lipid;

Case (5): the lipid composition also contains a phospholipid and a cationic lipid;

Case (6): the lipid composition also contains a steroid lipid and a cationic lipid;

Case (7): the lipid composition also contains a phospholipid, a steroid lipid, and a cationic lipid.

4. The lipid composition of claim 3, wherein the phospholipid is selected from the group consisting of 1,2-dilinoleoyl-sn-glycero-3-phosphocholine, 1,2-dimyristoyl-sn-glycero-phosphocholine, 1,2-dioleoyl-sn-glycero-3-phosphocholine, 1,2-dipalmitoyl-sn-glycero-3-phosphocholine, 1,2-distearoyl-sn-glycero-3-phosphocholine, 1,2-diundecanoyl-sn-glycero-phosphocholine, 1-palmitoyl-2-oleoyl-sn-glycero-3-phosphocholine, 1,2-di-O-octadecenyl-sn-glycero-3-phosphocholine, 1-oleoyl-2-cholesterylhemisuccinoyl-sn-glycero-3-phosphocholine, 1-hexadecyl-sn-glycero-3-phosphocholine, 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine, 1,2-diphytanoyl-sn-glycero-3-phosphoethanolamine, 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt, dioleoylphosphatidylserine, dipalmitoylphosphatidylglycerol, palmitoyloleoylphosphatidylethanolamine, distearoylphosphatidylethanolamine, dipalmitoylphosphatidylethanolamine, dimyristoylphosphoethanolamine, 1-stearoyl-2-oleoyl-phosphatidyethanolamine, 1-stearoyl-2-oleoyl-phosphatidylcholine, sphingomyelin, phosphatidylcholine, phosphatidylethanolamine, phosphatidylserine, phosphatidylinositol, phosphatidic acid, palmitoyloleoylphosphatidylcholine, lysophosphatidylcholine, lysophosphatidylethanolamine, and compositions thereof.

5. The lipid composition of claim 3, wherein the steroid lipid is selected from the group consisting of cholesterol, coprostanol, sitosterol, ergosterol, campesterol, stigmasterol, brassicasterol tomatidine, ursolic acid, a-tocopherol, and compositions thereof.

6. The lipid composition of claim 3, wherein the cationic lipid is selected from the group consisting of N,N-dioleyl-N,N-dimethylammonium chloride, N,N-distearyl-N,N-dimethylammonium bromide, N-[1-(2,3-dioleoyloxy)propyl]-N,N,N-trimethylammonium chloride, N-[1-(2,3-dioleyloxy)propyl]-N,N,N-trimethylammonium chloride, N,N- dimethyl-2,3-dioleyloxy-1-(dimethylamino)propane, 3-(didodecylamino)-N1,N1,4-tridodecyl-1-piperazineethanamine, N1-[2-(didodecylamino)ethyl]-N1,N4,N4-tridodecyl-1,4-piperazinediethanamine, 14,25-ditridecyl-15,18,21,24-tetraaza-octatriacontane, 1,2-dilinoleyloxy-N,N-dimethylaminopropane, 2,2-dilinoleyl-4-dimethylaminomethyl-[1,3]-dioxolane, heptatriaconta-6,9,28,31-tetraen-19-yl 4-(dimethylamino)butanoate, 2,2-dilinoleyl-4-(2-dimethylaminoethyl)-[1,3]-dioxolane, ((4-hydroxybutyl)azanediyl)bis(hexane-6,1-diyl)bis(2-hexyldecanoate), heptadecan-9-yl 8-((2-hydroxyethyl)(6-oxo-6-(undecyloxy)hexyl)amino)octanoate,

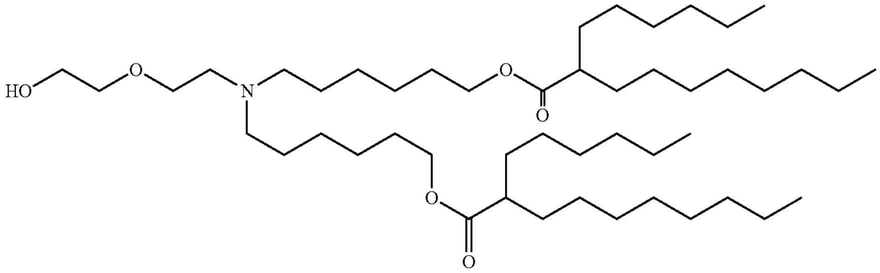

,

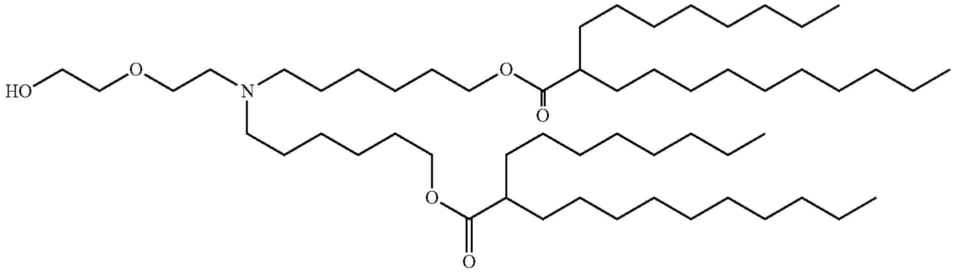

,

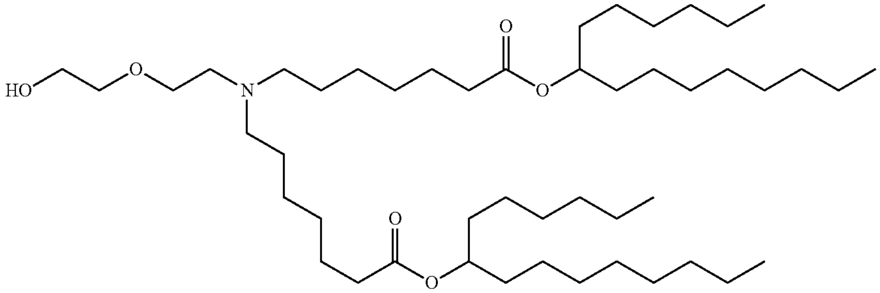

,

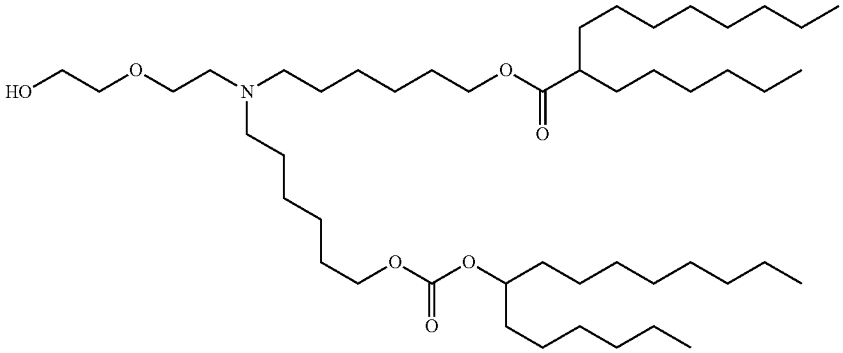

,

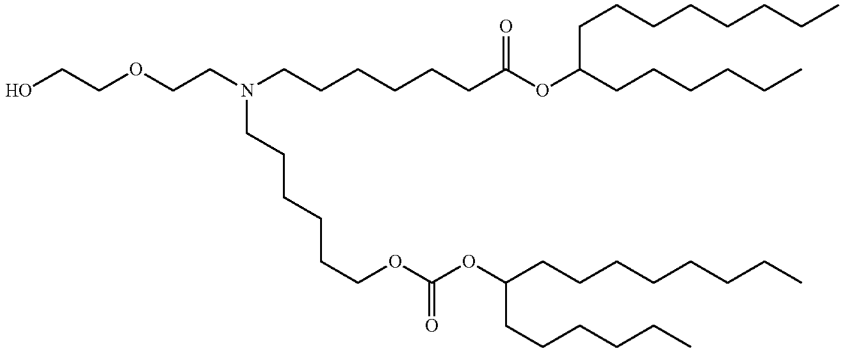

,

-continued
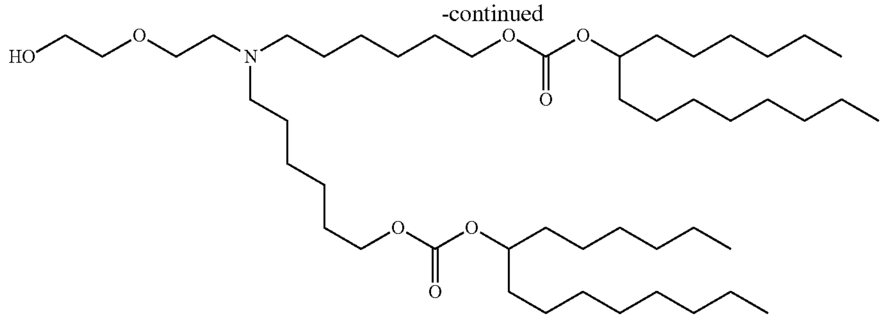
,
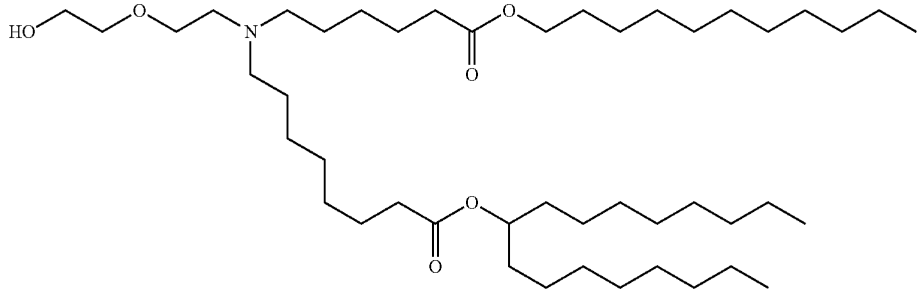
,
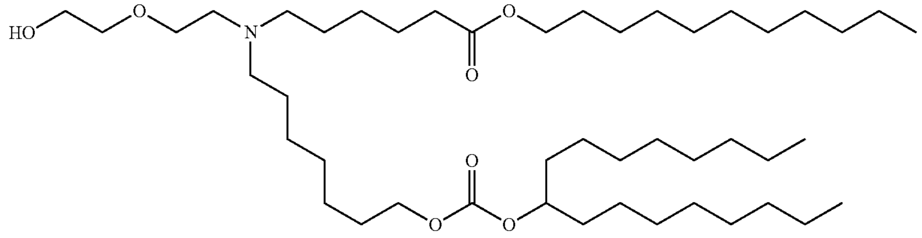
,
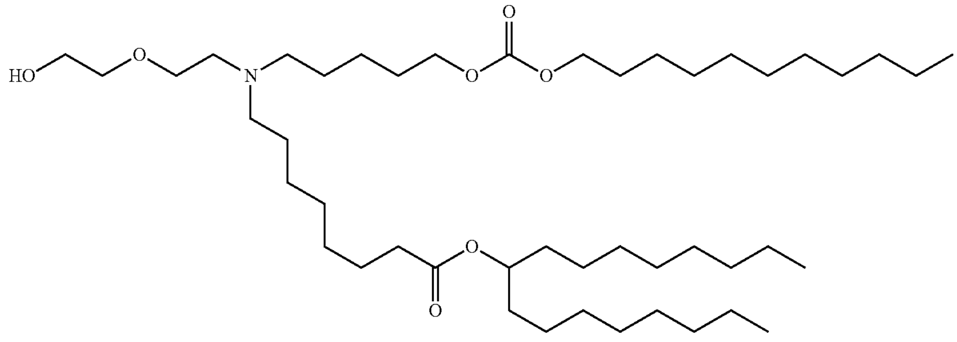
,
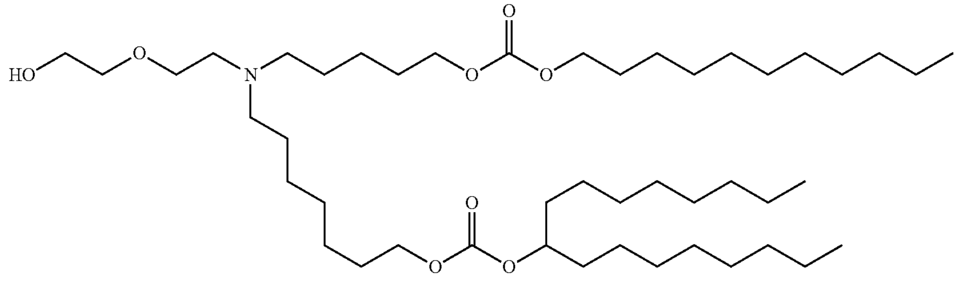
, -continued

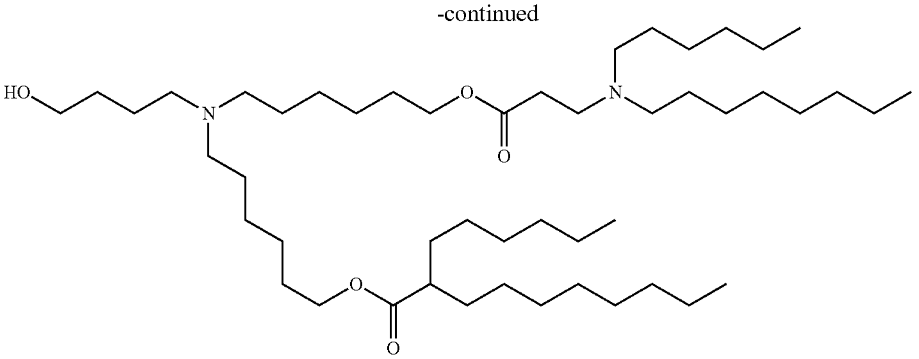

,

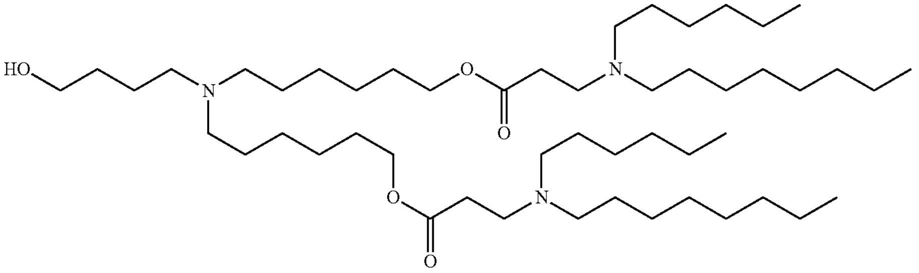

,

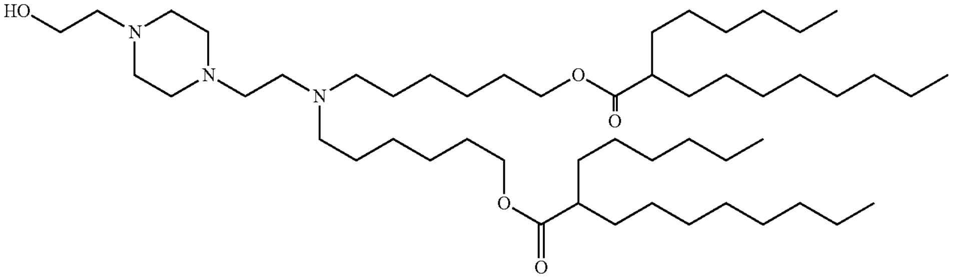

,

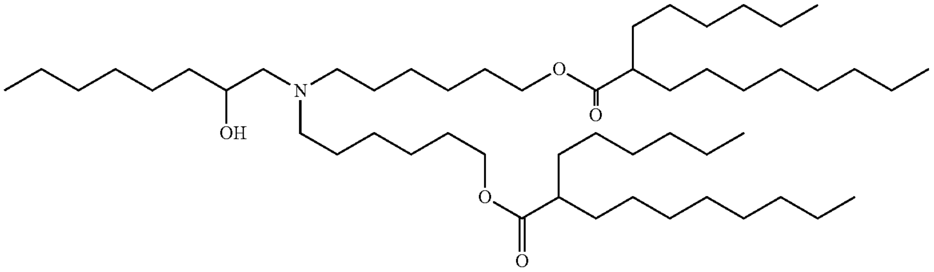

, and compositions thereof.

7. The lipid composition of claim 3, wherein, the molar percentage of PEGylated lipid in total lipids is 0.5 to 5%;

the molar percentage of cationic lipid in total lipids is 30 to 65%;

the molar percentage of phospholipid in total lipids is 7.5 to 13%;

the molar percentage of steroid lipid in total lipids is 35 to 50%.

8. A lipid pharmaceutical composition containing a lipid composition of claim 2 and a drug selected from the group consisting of nucleic acid drug, genetic vaccine, anti-neoplastic drug, small molecule drug, peptide drug, and protein drug.

9. The lipid pharmaceutical composition of claim 8, wherein the drug is a nucleic acid drug selected from the group consisting of DNA, RNA, antisense nucleic acid, plasmid, interfering nucleic acid, aptamer, antagomir, and ribozyme, wherein the RNA is selected from the group consisting of mRNA, saRNA, circRNA, miRNA, and siRNA.

10. The lipid pharmaceutical composition of claim 8, which is used as a medicine selected from the group consisting of drugs for treating cancer, anti-infective agents, antibiotic agents, antiviral agents, antifungal agents, and vaccines.

11. The lipid pharmaceutical composition of claim 8, which is an LNP-pharmaceutical composition, an LPP-pharmaceutical composition, or a PNP-pharmaceutical composition.

* * * * *